United States Patent
Xiong et al.

(10) Patent No.: US 10,053,695 B2
(45) Date of Patent: Aug. 21, 2018

(54) MODULATION OF CCR10 SIGNALS FOR TREATMENT OF SKIN AND INTESTINAL INFLAMMATORY DISEASES AND INFECTION

(71) Applicant: The Penn State Research Foundation, University Park, PA (US)

(72) Inventors: Na Xiong, State College, PA (US); Mingcan Xia, Brookline, MA (US)

(73) Assignee: THE PENN STATE RESEARCH FOUNDATION, University Park, PA (US)

( * ) Notice: Subject to any disclaimer, the term of this patent is extended or adjusted under 35 U.S.C. 154(b) by 94 days.

(21) Appl. No.: 14/669,663

(22) Filed: Mar. 26, 2015

(65) Prior Publication Data

US 2015/0273054 A1 Oct. 1, 2015

Related U.S. Application Data

(60) Provisional application No. 61/970,451, filed on Mar. 26, 2014.

(51) Int. Cl.
| | |
|---|---|
| *A61K 45/00* | (2006.01) |
| *C07K 14/00* | (2006.01) |
| *A61K 38/00* | (2006.01) |
| *A61P 17/06* | (2006.01) |
| *C12N 15/113* | (2010.01) |
| *C07K 14/52* | (2006.01) |
| *C07K 14/715* | (2006.01) |
| *A61K 45/06* | (2006.01) |
| *A61K 38/19* | (2006.01) |

(52) U.S. Cl.
CPC ........ *C12N 15/1138* (2013.01); *A61K 38/195* (2013.01); *A61K 45/06* (2013.01); *C07K 14/523* (2013.01); *C07K 14/7158* (2013.01); *C12N 15/113* (2013.01); *C12N 2310/14* (2013.01)

(58) Field of Classification Search
None
See application file for complete search history.

(56) References Cited

U.S. PATENT DOCUMENTS

| | | | | |
|---|---|---|---|---|
| 6,824,781 B2 * | 11/2004 | Wang | ................ | C07K 16/2866 424/130.1 |
| 2003/0077247 A1 * | 4/2003 | Caux | ..................... | A61K 39/39 424/85.1 |
| 2004/0005326 A1 * | 1/2004 | Mottram | .............. | A61K 39/008 424/184.1 |

OTHER PUBLICATIONS

English et al. Inflammation of the respiratory tract is associated with CCL28 and CCR10 expression in a murine model of allergic asthma. Immunology Letters, 2006; 103:92-100.*
Faaij et al. A possible role for CCL27/CTACK-CCR10 interaction in recruiting CD4+ T cells to skin in human graft-versus-host disease. British Journal of Haematology. 2006; 133(5):538-549.*
Homey et al. CCL27-CCR10 interactions regulate T cell-mediated skin inflammation. Nature Medicine, 2002; 8:157-165.*
Xiong et al. CCR10 And Its Ligands In Regulation Of Epithelial Immunity And Diseases. Protein Cell, 2012; 3(8):571-580.*
Ma. Animal Models of Disease. Modern Drug Discovery 2004, 7(6): 30-36).*
Sobirk et al. HUman chemokines as antimicrobial peptides with direct parasiticidal effect on Leishmania mexicana in vitro. PLoS One, 2013; 8(3):e58129.*
Brown et al. Tolerance to single, but not multiple, amino acid replacements in antibody VH CDR2. Journal of Immunology May 1996; 156(9):3285-91.*
Vajdos et al. Comprehensive functional maps of the antigen-binding site of an anti-ErbB2 antibody obtained with shotgun scanning mutagenesis.Journal of Molecular Biology, Jul. 5, 2002;320(2):415-28.*
Warzocha et al. Antisence strategy:biological utility and prospects in the treatment of hemtalogical malignancies. Leukemia and Lymphoma, Val. 24. pp. 267-281.*
McKeague et al. CHaleenges and opportunities for small molecule aptamer development. Journal of Nucleic Acids, 2012; 748913.*
Aagaard et al. RNAi therapeutics: principles, prospects and challenges. Advanced Drug Delivery Reviews 59 (2007) 75-86.*
Lazar et al. Transforming Growth Factor alpha: Mutation of Aspartic Acid 47 and Leucine 48 Results in Different Biological Activities. Molecular Cellular Biology, 8:1247-1252, 1988.*
Burgess et al. Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue. Journal of Cell Biology; 111:2129-2138, 1990.*
Bowie et al. Deciphering the Message in Protein Sequences: Tolerance to Amino Acid Substitutions. Science, 1990, 247:1306-1310.*
Xiong et al. CCR10 and its ligand in resulation of epithelial immunity and diseases. Protein Cell, 2012; 3(8):571-580.*
Homey et al. CCL27-CCR10 interactios regulate T-cell mediated skin inflammation. Nature Medicine, 2002; 8:157-165.*
Ma. Modern Drug Discovery 2004, 7(6): 30-36.*
Homey et al. CCL27-CCR10 interactions regulate T-cell mediated skin inflammation. Nature Medicine, 2002; 8:157-165 (Year: 2002).*
Xiong et al. CCR10 and its ligand in regulation of epithelial immunity and diseases. Protein Cell, 2012; 3(8):571-580 (Year: 2012).*
Bowie et al. Deciphering the Message in Protein Sequences: Tolerance to Amino Acid Substitutions. Science, 1990, 247:1306-1310 (Year: 1990).*
Burgess et al. Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue. Journal of Cell Biology; 111: 2129-2138, 1990 (Year: 1990).*
Lazar et al. Transforming Growth Factor alpha: Mutation of Aspartic Acid 47 and Leucine 48 Results in Different Biological Activities . Molecular Cellular Biology, 8:1247-1252, 1988 (Year: 1988).*

(Continued)

*Primary Examiner* — Vanessa L. Ford
*Assistant Examiner* — Sandra E Dillahunt
(74) *Attorney, Agent, or Firm* — Riverside Law LLP

(57) ABSTRACT

The invention provides compositions and methods for targeting CCR10 and/or the CCR10/ligand axis to modulate the immune response in a subject.

1 Claim, 25 Drawing Sheets

(56) References Cited

OTHER PUBLICATIONS

Aagaard et al. RNAi therapeutics: principles, prospects and challenges. Advanced Drug Delivery Reviews 59 (2007) 75-86 (Year: 2007).*
Warzocha et al. Antisence strategy:biological utility and prospects in the treatment of hematological malignancies. Leukemia and Lymphoma, 1997; 24:267-281 (Year: 1997).*
McKeague et al. Challenges and opportunities for small molecule aptamer development. Journal of Nucleic Acids, 2012;748913 (Year: 2012).*
Vajdos et al. Comprehensive functional maps of the antigen-binding site of an anti-ErbB2 antibody obtained with shotgun scanning mutagenesis.Journal of Molecular Biology, Jul. 5, 2002;320(2):415-28 (Year: 2002).*
Brown et al. Tolerance to single, but not multiple, amino acid replacements in antibody VH CDR2. Journal of Immunology May 1996 ; 156(9):3285-91. (Year: 1996).*
Ma. Modern Drug Discovery 2004, 7(6): 30-36 (Year: 2004).*
Pantelyushin, S., et al., Rort+ innate lymphocytes and T cells initiate psoriasiform plaque formation in mice 2012, J Clin Invest 122:2252-2256.
Reiss, Y., et al., CC Chemokine Receptor (CCR)4 and the CCR10 Ligand Cutaneous T Cell-attracting Chemokine (CTACK) in Lymphocyte Trafficking to Inflamed Skin 2001, *J Exp Med* 194:1541-1547.
Roediger, B., et al. Cutaneous immune-surveillance and regulation of inflammation by group 2 innate lymphoid cells , 2013, Nat Immunol 14:564-573.
Rosenblum, M.D., et al., Response to self antigen imprints regulatory memory in tissues 2012, *Nature* 480:538-542.
Salimi, M., et al. A role for IL-25 and IL-33-driven type-2 innate lymphoid cells in atopic dermatitis, 2013, J Exp Med 210:2939-50.
Sather, B.D., et al. Altering the distribution of Foxp3+ regulatory T cells results in tissue-specific inflammatory disease , 2007, *J Exp Med* 204:1335-1347.
Sharma, R., et al. IL-2 Regulates CD103 Expression on CD4 T cells in Scurfy Mice That Display Both CD103-Dependent and Independent Inflammation, 2009, *J Immunol* 183:1065-1073.
Soler, D., et al. CCR4 versus CCR10 in cutaneous T lymphocyte trafficking, 2003, *Blood* 101:1677-1682.
Tubo, N.J., et al. Short Communication: Chemokine Receptor Requirements for Epidermal T-Cell Trafficking, 2011, *Am J Pathol* 178:2496-2503.
Wang, W., et al, Identification of a Novel Chemokine (CCL28), which Binds CCR10 (GPR2) 2000, J Biol Chem 275:22313-22323.
Withers, D. R., et al Lymphoid tissue inducer cells maintain memory CD4 T cells within secondary lymphoid tissue. 2012. J Immunol 189:2094-2098.
Zlotnik, A., et al. The Chemokine Superfamily Revisited, 2012, *Immunity* 36:705-716.
Hong, K., et al. IL-12 Independently of IFN , Plays a Crucial Role in the pathogenesis of Murine Psoriasis-Like Skin Disorder, 1999, *J Immunol* 162:7480-7491.
Hu, S., et al, Critical roles of chemokine receptor CCR10 in regulating memory IgA responses in intestines 2011, Proc Natl Acad Sci U S A 108:E1035-1044.
Imai, Y., et al, Skin-specific expression of IL-33 activates group 2 innate lymphoid cells and elicits atopic dermatitis-like inflammation in mice 2013, Proc Natl Acad Sci U S A 110:13921-13926.

Jarmin, D.I. Cutting Edge: Identification of the Orphan Receptor G-Protein-Coupled Receptor 2 as CCR10 a Specific Receptor for the Chemokine ESkine, et al., 2000 *J Immunol* 164:3460-3464.
Jiang, X., et al. Skin infection generates non-migratory memory CD8+ T cells providing global skin immunity, 2012, *Nature* 483:227-231.
Jin et al., CCR10 is important for the development of skin-specific cells by regulating their migration and location 2010, J Immunol 185:5723-31.
Kim, B. S., et al, TSLP elicits IL-33-independent innate lymphoid cell responses to promote skin inflammation 2013, Sci Transl Med 5:170ra116.
Krummel, M.F., et al. , CD28 and CTLA-4 Have Opposing Effects on the Response of T Cells to Stimulation 1995, *J. Exp. Med.* 182:459-465.
Kunkel, E. J., et al, CCR10 expression is a common feature of circulating and mucosal epithelial tissue IgA Ab-secreting cells 2003, J Clin Invest 111:1001-1010.
Ma, H.L. et al., IL-22 is required for Th17 cell-mediated pathology in a mouse model of psoriasis-like skin inflammation 2008, *J Clin Invest* 118:597-607.
Mackay, L.K., et al., Long-lived epithelial immunity by tissue-resident memory T cells in the absence of persisting local antigen presentation 2012, *Proc Natl Acad Sci U S A* 109:7037-7042.
McCully, M.L., et al., Epidermis skin homing receptor expression in human T cells 2012, *Blood* 120:4591-4598.
Morales, J., et al., CTACK, a skin-associated chemokine that preferentially attracts skin-homing memory T cells 1999, *Proc Natl Acad Sci U S A* 96:14470-14475.
Morteau, O., et al, An Indispensable Role for the Chemokine Receptor CCR10 in IgA Antibody Secreting Cell Accumulation 2008, J Immunol 181:6309-6315.
Pan, J., et al, Cutting Edge: A Novel Chemokine Ligand for CCR10 And CCR3 Expressed by Epithelial Cells in Mucosal Tissues 2000, J Immunol 165:2943-2949.
Campbell, J.J. , et al., Cutting Edge: Chemokine Receptor CCR4 Is Necessary for Antigen-Driven Cutaneous Accumulation of CD4 T Cells under Physiological Conditions2007, *J Immunol* 178:3358-3362.
Chen, L. et al, CCL27 is a critical factor for the development of atopic dermatitis in the keratin-14 IL-4 transgenic mouse model 2006, *Int Immunol* 18:1233-1242.
Clark, R.A. Skin resident T cells: the ups and downs of on site immunity , 2010, *J Invest Dermatol* 130:362-370.
Dudakov, J. A et al,. Interleukin-22 drives endogenous thymic regeneration in mice, 2012, Science 336:91-95.
Dudda, , et al., J.C.Foxp3+ regulatory T cells maintain immune homeostasis in the skin 2008, *J Exp Med* 205:1559-1565.
Feng, N. , et al Redundant Role of Chemokines CCL25/TECK and CCL28/MEC in IgA+ Plasmablast Recruitment to the Intestinal Lamina Propria After Rotavirus Infection, 2006, J Immunol 176:5749-5759.
Francisco, L.M., et al.PD-L1 regulates the development maintenance and function of induced regulatory T cells, 2009, *J Exp Med* 206:3015-3029.
Girardi, M., et al., Resident Skin-specific T Cells Provide Local Non redundant Regulation of Cutaneous Inflammation 2002, *J Exp Med* 195:855-867.
Hanash, A. M., et al, Interleukin-22 protects intestinal stem cells from immune-mediated tissue damage and regulates sensitivity to graft vs. host disease 2012, Immunity 37:339-350.

* cited by examiner

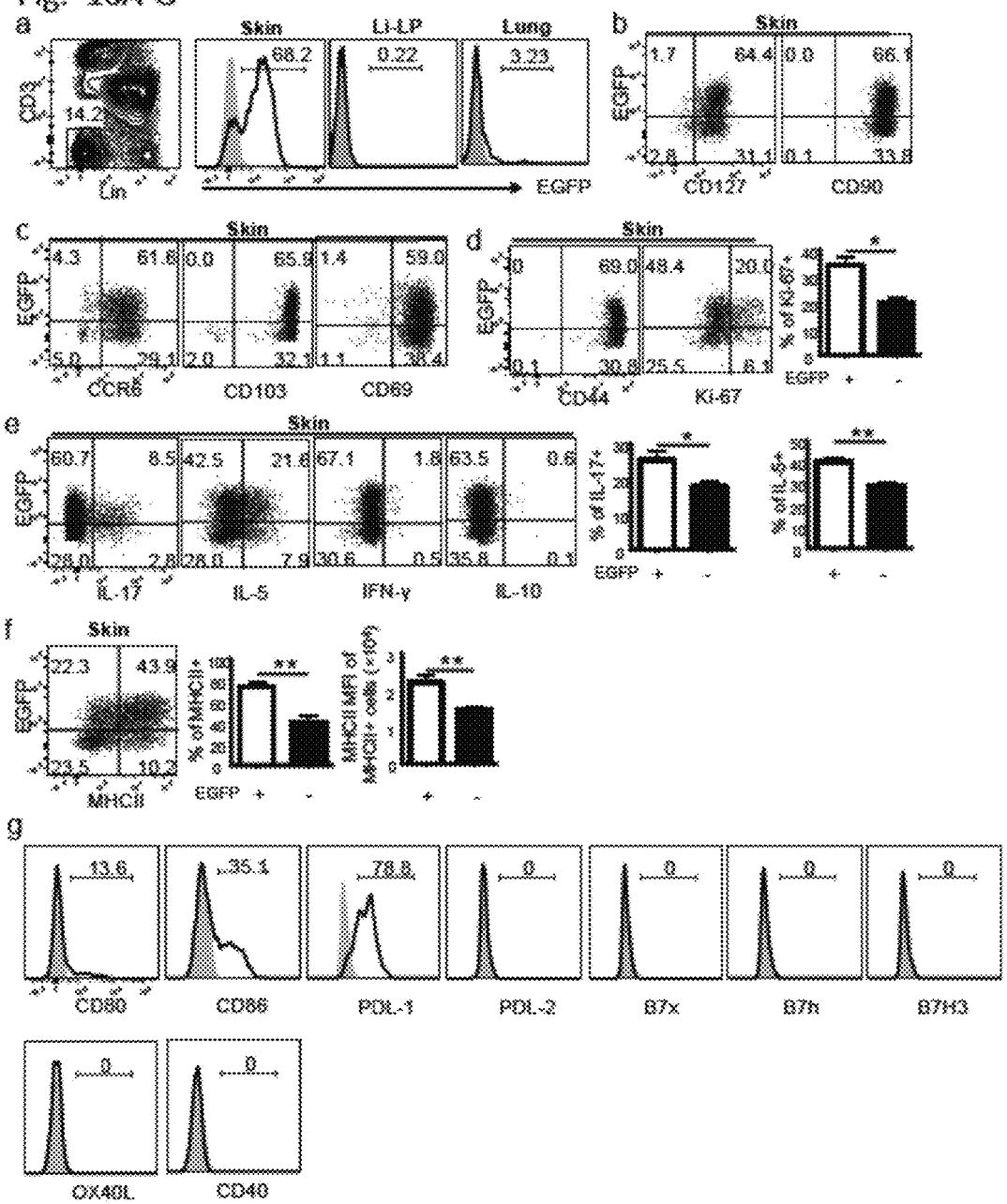

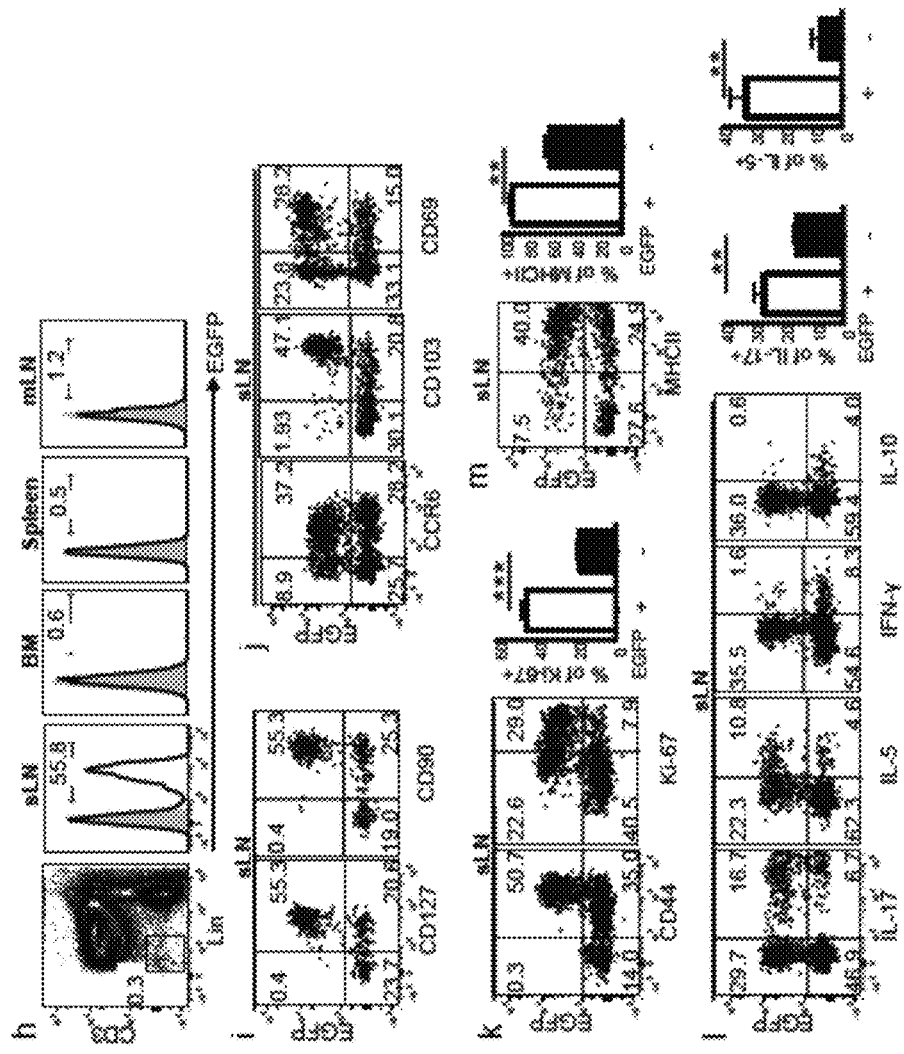
Fig. 16H-M

SEQUENCE LISTING

```
<160> NUMBER OF SEQ ID NOS: 10

<210> SEQ ID NO 1
<211> LENGTH: 23
<212> TYPE: DNA
<213> ORGANISM: Artificial
<220> FEATURE:
<223> OTHER INFORMATION: Chemically synthesized

<400> SEQUENCE: 1
cctattttac accaaccccc agt                                            23

<210> SEQ ID NO 2
<211> LENGTH: 21
<212> TYPE: DNA
<213> ORGANISM: Artificial
<220> FEATURE:
<223> OTHER INFORMATION: Chemically synthesized
```

```
<400> SEQUENCE: 2
gggtaggggc gttctgcgaa a                                              21

<210> SEQ ID NO 3
<211> LENGTH: 17
<212> TYPE: DNA
<213> ORGANISM: Artificial
<220> FEATURE:
<223> OTHER INFORMATION: Chemically synthesized

<400> SEQUENCE: 3
ttctatggcc cagaccc                                                   17

<210> SEQ ID NO 4
<211> LENGTH: 20
<212> TYPE: DNA
<213> ORGANISM: Artificial
<220> FEATURE:
<223> OTHER INFORMATION: Chemically synthesized

<400> SEQUENCE: 4
ggcaccacta gttggttgtc                                                20

<210> SEQ ID NO 5
<211> LENGTH: 18
<212> TYPE: DNA
<213> ORGANISM: Artificial
<220> FEATURE:
<223> OTHER INFORMATION: Chemically synthesized

<400> SEQUENCE: 5
tctcgcagca gcacatca                                                  18

<210> SEQ ID NO 6
<211> LENGTH: 22
<212> TYPE: DNA
<213> ORGANISM: Artificial
<220> FEATURE:
<223> OTHER INFORMATION: Chemically synthesized

<400> SEQUENCE: 6
cacaccagca ggttatcatc at                                             22

<210> SEQ ID NO 7
<211> LENGTH: 20
<212> TYPE: DNA
<213> ORGANISM: Artificial
<220> FEATURE:
<223> OTHER INFORMATION: Chemically synthesized

<400> SEQUENCE: 7
accaaagcca caaagcagcc                                                20

<210> SEQ ID NO 8
<211> LENGTH: 19
<212> TYPE: DNA
<213> ORGANISM: Artificial
<220> FEATURE:
<223> OTHER INFORMATION: Chemically synthesized

<400> SEQUENCE: 8
ccgactggga agtgggtgc                                                 19

<210> SEQ ID NO 9
```

```
<211> LENGTH: 18
<212> TYPE: DNA
<213> ORGANISM: Artificial
<220> FEATURE:
<223> OTHER INFORMATION: Chemically synthesized

<400> SEQUENCE: 9
cccatctacg agggctat                                               18

<210> SEQ ID NO 10
<211> LENGTH: 17
<212> TYPE: DNA
<213> ORGANISM: Artificial
<220> FEATURE:
<223> OTHER INFORMATION: Chemically synthesized

<400> SEQUENCE: 10
tgtcacgcac gatttcc                                                17
```

MODULATION OF CCR10 SIGNALS FOR TREATMENT OF SKIN AND INTESTINAL INFLAMMATORY DISEASES AND INFECTION

CROSS-REFERENCE TO RELATED APPLICATIONS

This application claims priority to U.S. Provisional Application Ser. No. 61/970,451, filed Mar. 26, 2014, the content which is incorporated by reference herein in its entirety.

STATEMENT REGARDING FEDERALLY SPONSORED RESEARCH OR DEVELOPMENT

This invention was made with government support under Grant Nos. AI071043 and AR064831, awarded by the National Institutes of Health and under Hatch Act Project No. PEN04446, awarded by the United States Department of Agriculture/NIFA. The Government has certain rights in the invention.

BACKGROUND OF THE INVENTION

As the external surface of a body, skin is under frequent assaults from environmental agents. To maintain its integrity and function, immune cells in the skin are tightly regulated to tolerate harmless antigens but respond to dangerous assaults. Skin-resident T cells are unique populations of immune cells with memory cell-like properties (Clark, R. A., 2010, *J Invest Dermatol* 130:362-370). Among them, the resident $CD4^+$ regulatory T (Treg) cells are critical to maintain the immune homeostasis of healthy skin (Sather, B. D., et al., 2007, *J Exp Med* 204:1335-1347 and Dudda, J. C., et al., 2008, *J Exp Med* 205:1559-1565), while the resident memory effector T (Teff) cells could provide faster immune responses to infection in the skin than those of the circulation (Gebhardt, T., et al., 2009, *Nat Immunol* 10:524-530, Jiang, X., et al., 2012, *Nature* 483:227-231 and Mackay, L. K., et al., 2012, *Proc Natl Acad Sci USA* 109:7037-7042). The antigen encounter in the skin might also induce memory Treg cells to counterbalance the Teff response (Rosenblum, M. D., et al., 2012, *Nature* 480:538-542). Dysregulation of Treg and Teff cells in the skin is associated with allergy and other skin inflammatory diseases.

CCR10 and its ligand CCL27 is the most skin-specific chemokine/receptor pair (Zlotnik, A., et al., 2012, *Immunity* 36:705-716). With CCL27 constitutively expressed in healthy skin and further upregulated in inflamed skin in patients of psoriasis and dermatitis and animal models, CCR10/CCL27 have been implicated in migration of skin T cells under both healthy and disease conditions (Morales, J., et al., 1999, *Proc Natl Acad Sci USA* 96:14470-14475, Homey, B., et al., 2000, *J Immunol* 164:3465-3470, Jarmin, D. I., et al., 2000 *J Immunol* 164:3460-3464 and Homey, B., et al., 2002, *Nat Med* 8:157-165). In humans, all blood $CCR10^+$ T cells display memory cell markers, co-express the skin-homing molecule *cutaneous* lymphocyte antigen (CLA) and respond to chemoattraction of CCL27, suggesting a role of CCR10/CCL27 in recruitment of memory T cells into the skin (Morales, J., et al., 1999, *Proc Natl Acad Sci USA* 96:14470-14475, Homey, B., et al., 2002, *Nat Med* 8:157-165 and Soler, D., et al., 2003, *Blood* 101:1677-1682). However, immunohistochemical staining in one early study found only scattered $CCR10^+$ cells in healthy skin of humans (Homey, B., et al., 2002, *Nat Med* 8:157-165). Instead, most T cells of inflamed skin of psoriatic and dermatitic patients express CCR10. Since CCL27 was also upregulated in the inflamed skin, it was suggested that CCR10/CCL27 are involved in migration of T cells during the skin inflammation and inhibiting CCR10/CCL27-derived signals could be used to treat skin inflammatory diseases (Homey, B., et al., 2002, *Nat Med* 8:157-165). But the flow cytometric analysis of T cells isolated from the allergen and bacterial chancroid-induced inflamed human skin in another study found only a small percentage of $CCR10^+$ cells, suggesting that CCR10 is unlikely critical for migration of most T cells during the skin inflammation (Soler, D., et al., 2003, *Blood* 101:1677-1682). A recent study reported that CCR10 is co-expressed on half of human blood $CCR8^+$ T cells, a population with the skin-homing potential, but T cells migrating out of the healthy human skin do not express CCR10 although non-migrating skin-resident T cells were not assessed (McCully, M. L., et al., 2012, *Blood* 120:4591-4598). $CCR10^+$ $CD4^+$ T cells of human blood are also enriched with IL-22-producing cells that also preferentially express CCR6, another chemokine receptor associated with skin localization (Duhen, T., et al., 2009, *Nat Immunol* 10:857-863 and Trifari, S., et al., 2009, *Nat Immunol* 10:864-871). Up to now, the role of CCR10/CCL27 as homeostatic or inflammatory regulators of skin T cells remains unclear.

CCR10 was also expressed on skin-resident innate lymphoid cells (ILC) (Salimi, M., et al., 2013, *J Exp Med* 210:2939-50). ILC cells are a family of innate lymphocytes preferentially enriched in barrier tissues such as the intestine and skin and involved in the local tissue homeostasis and inflammation (Spits, H., et al., 2012 Annu Rev Immunol 30:647-675). ILCs do not express cell-surface markers associated with other immune cell lineages (lineage marker negative or LIN−) but express the common hematopoietic lineage marker CD45 and surface molecules commonly associated with lymphocytes such as CD90 and CD127 (Spits, H., et al., 2012 Annu Rev Immunol 30:647-675). Based on their developmental pathways and functional potentials in analog to the different T helper cell (Th) subsets, ILCs were divided into three major groups (ILC1-3) (Spits, H., et al., 2013, Nat Rev Immunol 13:145-149). ILC1 comprises natural killer (NK) cells and other ILCs that produce IFN-γ. ILC2 cells predominantly express Th2-type cytokines such as IL-5 and IL-15, and ILC3 cells produce Th-17/22 type cytokines such as IL-17 and IL-22. Through the production of unique cytokines and direct cell-cell interaction, ILCs have been reported to act on various other subsets of immune cells, such as T cells, mast cells, eosinophils and macrophages, and epithelial cells to regulate homeostasis as well as inflammation in barrier tissues (Withers, D. R., et al. 2012. J Immunol 189:2094-2098; Hanash, A. M., et al, 2012, Immunity 37:339-350; Dudakov, J. A., et al, 2012, Science 336:91-95; Pantelyushin, S., et al., 2012, J Clin Invest 122:2252-2256; Roediger, B., et al., 2013, Nat Immunol 14:564-573; Kim, B. S., et al, 2013, Sci Transl Med 5:170ra116; Imai, Y., et al, 2013, Proc Natl Acad Sci USA 110:13921-13926). However, roles of CCR10 in regulating localization and function of ILCs are not clear.

Animal studies also provide complex and sometimes seemingly contradicting results on functions of CCR10/CCL27. In a mouse model of the allergen DNFB (2,4-dinitro-1-fluorobenzene)-induced contact hypersensitive response (CHS), one study found that the antibody neutralization of CCL27 reduced the skin T cell recruitment and inflammation, suggesting a pivotal role of the CCL27/CCR10 axis in T cell-mediated skin inflammation (Homey, B., et al., 2002, *Nat Med* 8:157-165). Similarly, in the keratin-14 promoter-driven IL-4 transgenic mouse model of atopic dermatitis, subcutaneous injection of anti-CCL27 antibodies reduced inflammation (Chen, L., et al., 2006, *Int Immunol* 18:1233-1242). However, the anti-CCL27 antibody treatment did not affect recruitment of transferred CD4$^+$ T cells into the DNFB-inflamed skin or allergens-induced CHS responses in other studies (Reiss, Y., et al., 2001, *J Exp Med* 194:1541-1547 and Mirshahpanah, P., et al., 2008, *Exp Dermatol* 17:30-34). Recently, it was reported that CCR10-sufficient and -knockout CD4$^+$ T cells migrate similarly to the cognate-antigen-stimulated skin, demonstrating directly that CCR10 is not critical for the T cell infiltration into inflamed skin (Tubo, N. J., et al., 2011, *Am J Pathol* 178:2496-2503). Up to now, the role of CCR10 in regulation of skin immune homeostasis and responses in vivo remains unknown.

CCR10 could be also potentially involved in regulation of immune homeostasis and response in intestines. In both large and small intestines, the mucosa-specific ligand for CCR10, CCL28, is highly expressed by intestinal epithelial cells (Pan, J., et al, 2000, J Immunol 165:2943-2949; Wang, W., et al, 2000, J Biol Chem 275:22313-22323). CCR10 was previously found to express on all IgA-antibody secreting cells (IgA-ASC) and suggested to regulate their intestinal migration (Kunkel, E. J., et al, 2003, J Clin Invest 111:1001-1010). However, anti-CCL28 antibody blockage or CCR10-knockout had little effects on IgA responses to infections or homeostatic productions of IgA antibodies in intestines (Feng, N., et al, 2006, J Immunol 176:5749-5759; Morteau, O., et al, 2008, J Immunol 181:6309-6315; Hu, S., et al, 2011, Proc Natl Acad Sci USA 108:E1035-1044). We found recently that CCR10 is critical in the IgA memory responses against infections in intestines (Hu, S., et al, 2011, Proc Natl Acad Sci USA 108:E1035-1044), suggesting potentially important roles of CCR10 in intestinal immune responses. Related with this, expression of the ligand CCL28 was upregulated in inflamed intestines (35)(25). However, up to now, functional importance of CCR10 in intestinal homeostatic regulation and diseases is unknown.

There is a need in the art to better understand the role of CCR10 in the immune system. In addition, there is a need in the art for the development of successful therapeutics for the treatment of skin and intestinal diseases. The present invention satisfies the need in the art for development of new approaches for efficient means to induce an immune response to treat skin and intestinal diseases.

SUMMARY OF THE INVENTION

The invention provides a composition for modulating an immune response in a mammal. In one embodiment, the composition comprises a modulator of one or more of CCR10, a ligand of CCR10, and a down-stream effector protein in the CCR10/ligand axis.

In one embodiment, the modulator is an inhibitor of one or more of CCR10, a ligand of CCR10, and a down-stream effector protein in the CCR10/ligand axis, wherein the inhibitor enhances the immune response in the mammal.

In one embodiment, the inhibitor is selected from the group consisting of a small interfering RNA (siRNA), a microRNA, an antisense nucleic acid, a ribozyme, an expression vector encoding a transdominant negative mutant, an antibody, a peptide and a small molecule.

In one embodiment, the modulator is an activator of one or more of CCR10, a ligand of CCR10, and a down-stream effector protein in the CCR10/ligand axis, wherein the activator inhibits the immune response in the mammal.

In one embodiment, the activator is selected from the group consisting of a nucleic acid, a protein, a peptide, a peptidomemetic, a chemical compound and a small molecule.

In one embodiment, the composition further comprises a pharmaceutically acceptable carrier.

In one embodiment, the composition further comprises an agent selected from the group consisting of an immunostimulatory agent, an antigen, an anti-viral agent, an anti-bacterial agent, an anti-tumor agent, and any combination thereof.

The invention also provides a method of modulating an immune response in a mammal. In one embodiment, the method comprises administering to the mammal in need thereof an effective amount of a composition comprising a modulator of one or more of CCR10, a ligand of CCR10, and a down-stream effector protein in the CCR10/ligand axis.

In one embodiment, the mammal is suffering from a skin disease.

In one embodiment, the skin disease is associated with an infection.

In one embodiment, the skin disease is associated with an inappropriate level of immune response that is unable to alleviate the skin disease.

In one embodiment, the mammal is suffering from an autoimmune disease.

In one embodiment, the mammal is suffering psoriasis.

In one embodiment, the mammal is suffering intestinal inflammation.

In one embodiment, the composition is administered in combination with a therapeutic agent to the mammal in need thereof.

In one embodiment, the therapeutic agent is selected from the group consisting of an anti-tumor agent, a chemotherapeutic agent, an anti-cell proliferation agent, an anti-tumor vaccine and any combination thereof.

In one embodiment, the therapeutic agent is administered simultaneously, prior to, or after administration of the modulator.

In one embodiment, the mammal is a human.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1, comprising (FIG. 1A) Ear thickness changes ($\Delta$T) of CCR10$^{-/-}$ and CCR10$^{+/-}$ mice in a DNFB-induced CHS assay. N≥6 mice of each genotype in at least two independent experiments (applied in other analyses in experiments disclosed herein). (FIG. 1B) Ear thickness changes of CCR10$^{-/-}$ and CCR10$^{+/-}$ mice after the one-time topical application of DNFB on the ear. N≥10. *P<0.05; P<0.005; *P<0.001 and NS: no significant difference (applied to all figures). (FIG. 1C) qRT-PCR analysis of RNA isolated from treated ears 3 days after the one-time DNFB application for TNF-$\alpha$, IL-1$\beta$ and IL-10. N=5 each. "No" indicates untreated skin samples (n=3). The values are relative levels normalized on $\beta$-actin. (FIG. 1D) Ear thickness changes of CCR10$^{-/-}$ and CCR10$^{+/-}$ mice after the one-time topical application of FITC (0.5%). N=21 for CCR10$^{+/-}$ mice and N=19 for CCR10$^{-/-}$ mice. (FIG. 1E)

qRT-PCR analysis of RNA isolated from the treated skin 3 days after the one-time FITC-application for TNF-α, IL-1β and IL-10 as in (FIG. 1C). N=4 each. (FIG. 1F) Ear thickness changes of CCR10$^{-/-}$ and CCR10$^{+/-}$ mice after the one-time topical application of TPA. N≥10 for each genotype.

FIG. 2, comprising (FIG. 2A) Flow cytometric (FACS) analysis of skin lymphocyte preparations of CCR10$^{-/-}$ and CCR10$^{+/-}$ mice for EGFP$^+$ total CD3$^+$ T cells (top) and γδT cells (bottom). The number next to each gate is the percentage (%) of the gated cells of total events in the histogram. The CD3$^{high}$CCR10$^{low}$ cells are Vγ3$^+$ γδT cells. (FIG. 2B) FACS analysis of gated skin EGFP$^+$CD3$^+$ T cells of CCR10$^{-/-}$ and CCR10$^{+/-}$ mice for CD4$^+$ and CD8$^+$ subsets. (FIG. 2C) Average percentages of EGFP$^+$ CD8$^+$ and CD4$^+$ cells of skin lymphocyte preparations in CCR10$^{+/-}$ and CCR10$^{-/-}$ mice, calculated by multiplying % of total EGFP$^+$ T cells (FIG. 2A) and % of CD4$^+$ and CD8$^+$ cells of the total EGFP$^+$ T cells (FIG. 2B). (FIG. 2D) FACS analysis of gated skin EGFP$^+$CD4$^+$ T cells of CCR10$^{-/-}$ and CCR10$^{+/-}$ mice for Foxp3$^+$ Treg cells. (FIG. 2E) Average percentages of Foxp3$^+$CD25$^+$ Treg cells of skin CD4$^+$ T cells in CCR10$^{+/-}$ and CCR10$^{-/-}$ mice, calculated from the FACS analysis in (FIG. 2D). N≥10. (FIG. 2F) Average numbers of EGFP$^+$ CD4$^+$Foxp3$^+$, CD4$^+$ and CD4$^-$(CD8$^+$) T cells isolated from skin of CCR10$^{+/-}$ vs. CCR10$^{-/-}$ mice. N≥10. (FIG. 2G) FACS analysis of skin CD4$^+$ T cells of CCR10$^{-/-}$ and CCR10$^{+/-}$ mice for the IL-10$^+$ subset. Average percentages of IL-10$^+$ cells of the EGFP$^+$ or EGFP$^-$ CD4$^+$ cells were shown on the left. N=4 each. (FIG. 2H) FACS analysis of skin CD4$^+$ T cells of CCR10$^{-/-}$ and CCR10$^{+/-}$ mice for the IL-17A$^+$ subset. The bar graphs show average percentages of IL-17A$^+$ cells of EGFP$^+$ or EGFP$^-$ CD4$^+$ cells (middle) and their MFI for the IL-17A staining (right). N=6 each. (FIG. 2I) Levels of IL-17A production by purified CCR10$^{+/-}$ or CCR10$^{-/-}$ skin EGFP$^+$CD4$^+$CD25$^-$ T cells stimulated with IL-2 and coated anti-CD28/anti-TCRβ antibodies in culture. N=4-5. (FIG. 2J) Relative contribution of transferred CCR10$^{-/-}$ vs. CCR10$^{+/-}$ BM cells to the indicated skin T cell subsets in irradiated WT recipient mice. N=5 each. (FIG. 2K) FACS analysis of skin CD4$^+$ T cells of CCR10$^{-/-}$ vs. CCR10$^{+/-}$ BM donor origins in recipient mice for the IL-17A$^+$ cells, presented as in (FIG. 2H). N=5 each.

FIG. 3, comprising (FIG. 3A) FACS analysis of T cells of untreated or inflamed skin of CCR10$^{+/-}$ mice for CCR10 (EGFP) expression. The inflamed skin was of mice 1 day after DNFB-induced CHS response. The gray lines are of WT cells as negative controls for EGFP. Repeated twice. (FIGS. 3B-3D) FACS analysis for EGFP on skin T cells in Rag1$^{-/-}$ mice transferred with CCR10$^{+/-}$ or CCR10$^{-/-}$ EGFP$^-$ splenic T cells 1 day (FIG. 3B) or 1 month (FIG. 3C, 3D) after the DNFB-induced CHS. Average percentages of EGFP$^+$ skin T cells of CCR10$^{+/-}$ vs. CCR10$^{-/-}$ donors 1 month after the CHS induction are shown in (FIG. 3D). N=10 each. (FIG. 3E) Representative FACS analysis for molecules associated with memory on skin EGFP$^+$ vs. EGFP$^-$ T cells of the CCR10+/− donor T cell origins in Rag1$^{-/-}$ mice 1 day after DNFB-induced CHS. N=4. (FIG. 3F) FACS analysis of EGFP expression on Teff (top) and Treg (bottom) cells of the skin of Rag1$^{-/-}$ mice 7-8 weeks after they were transferred with EGFP$^-$ naïve splenic CD4$^+$ Teff cells only (right) or a mixture of EGFP$^-$ naïve splenic CD4$^+$ Teff and Treg cells (left). N=4. (FIG. 3G) FACS analysis for EGFP on skin T cells of one-month old CCR10$^{+/-}$ Scurfy and control mice. N=5.

FIG. 4, comprising FIGS. 4A and 4C, is a series of images demonstrating that CCR10 is critical in localization of CCR10$^+$ T cells into the homeostatic skin. (FIG. 4A-4B) Flow cytometry of gated CD3$^+$CD8$^+$ T cells isolated from Ova-treated inflamed ear skin (FIG. 4A) and untreated torso skin (FIG. 4B) for the donor-derived OT-I T cells (CD45.1$^-$CD45.2$^+$) (top) and expression of EGFP of the donor OT-I T cells (bottom). (FIG. 4C) Average numbers of EGFP$^+$ CCR10$^{+/-}$ and CCR10$^{-/-}$ OT-1 T cells isolated from the inflamed ear skin and un-affected torso skin based on the analyses of panel B. N=5-6.

FIG. 5, comprising (FIG. 5A) Ear thickness changes of CCR10$^{-/-}$ and CCR10$^{+/-}$ mice in a DNFB-induced memory CHS assay. N≥6. (FIG. 5B) Representative H&E staining of ear sections 3 days after the DNFB-induced memory CHS response (×400). N=4. (FIG. 5C) qRT-PCR analysis of TNF-α, IL-1β and IL-10 transcripts in the treated skin 3 days after the DNFB-induced memory CHS. N=4. (FIG. 5D) Ear thickness changes of Rag1$^{-/-}$ mice transferred with EGFP$^-$ CCR10$^{-/-}$ and CCR10$^{+/-}$ splenic T cells in the DNFB-induced memory CHS. N≥6.

FIG. 6, comprising (FIG. 6A) Levels of Leishmania-specific 16S rDNA in the skin of CCR10$^{-/-}$ and CCR10$^{+/-}$ mice at different time-points after infection, determined by qPCR and normalized on mouse β-actin. N=11, 10 and 4 of each genotype for 3 days, 1 and 2 months post the infection respectively. (FIG. 6B) qRT-PCR analysis of TNF-α, IL-1β and IL-10 transcripts in the infected ears of CCR10$^{-/-}$ vs. CCR10$^{+/-}$ on Day 3 post the L. major infection. N=5 each. (FIG. 6C) Representative ear lesions at infection sites in CCR10$^{-/-}$ and CCR10$^{+/-}$ mice 1 month after the L. major injection. (FIG. 6D) Numbers of total, EGFP$^+$ and EGFP$^-$ T cells in infected ears of CCR10$^{-/-}$ and CCR10$^{+/-}$ mice 1 month post the Leishmania infection. N=3 each.

FIG. 7, comprising (FIGS. 7A and 7B) Flow cytometric analysis of gated CD3$^+$CD4$^+$ T cells isolated from the healthy skin (FIG. 7A) and blood (FIG. 7B) of humans for the CCR10 expression. The number in each gate is the average percentage of cells in the gate of total events, expressed as means±standard errors. N=3 individual samples for each analysis. The isotype control staining for the CCR10 staining was shown in the left panels.

FIG. 12, comprising (FIG. 12A) Representative flow cytometric analysis of gated skin T cell populations (indicated in the figure) for their CCR10$^{-/-}$ vs. CCR10$^{+/-}$ bone marrow origins in irradiated wild type recipients two months after the BM transfer. CD45.1 and CD45.2 polymorphism was used to distinguish T cells of different donor and host origins. Total splenic T cells were analyzed for their CCR10$^{-/-}$ vs. CCR10$^{+/-}$ bone marrow origins and used as the normalized reference to corresponding skin T cell populations. (FIG. 12B) Relative contribution of transferred CCR10$^{-/-}$ vs. CCR10$^{+/-}$ BM cells to the indicated EGFP$^-$ skin T cell subsets in irradiated WT recipient mice. N=5 each.

FIG. 13, comprising (FIG. 13A-13B) Flow cytometry of gated CD3+CD4+ OT-II cells isolated from Ova-treated inflamed ear skin (FIG. 13A) and untreated torso skin (FIG. 13B) for their expression of EGFP. (FIG. 13C) Average percentages of CCR10+/− and CCR10−/− OT-II T cells of the inflamed ear skin and un-inflamed torso skin that express EGFP (CCR10). N=3 each.

FIG. 16, comprising FIGS. 16A through 16M is a series of imaged demonstrating the identification and characterization of CCR10+ sILCs. FIG. 16A: Flow cytometric analysis of CCR10 (EGFP) expression on ILCs from the skin, lamina propria of large intestines (Li-LP) and lungs of CCR10$^{+/EGFP}$ mice. The contour plot on the left, which is gated on skin CD45+ cells, shows the gating strategy for skin_ILCs. Histograms on the right show the CCR10 (EGFP) expression on ILCs of indicated tissues. Gray areas in histograms are of WT cells as negative controls for EGFP. Skin_ILCs are gated as CD45+CD3−Lin− cells. Intestinal and lung ILCs are gated as CD45+CD3−Lin−IgA−IgM−CD138−CD19− cells. Representative of >50 experiments for the skin, 7 for lungs and 4 for intestines. FIG. 16B&C: Representative flow cytometric analysis of expression of CD127 and CD90 (B), and CCR6, CD103 and CD69 (C), on EGFP+ and EGFP− skin_ILCs of CCR10$^{+/EGFP}$ mice. N=3. FIG. 16D: Analysis of expression of CD44 and Ki-67 on EGFP+ and EGFP− skin_ILCs of CCR10$^{+/EGFP}$ mice. The bar graph on the right compares average percentages of Ki-67+ cells among EGFP+ and EGFP− skin_ILCs. N=3. FIG. 16E: Flow cytometry analysis of expression of cytokines IL-17, IL-5, IFN-γ and IL-10 on EGFP+ and EGFP− skin_ILCs of CCR10$^{+/EGFP}$ mice. Bar graphs on the right show percentages of IL-17+ (N=6) and IL-5+ (N=4) cells among EGFP+ and EGFP− skin_ILCs. N=2 for IFN-γ and IL-10. FIG. 16F: Expression of MHCII on EGFP+ and EGFP− skin_ILCs of CCR10$^{+/EGFP}$ mice. N=5. Bar graphs show average percentages of MHCII+ cells of EGFP+ and EGFP− skin_ILCs (left) and median fluorescence intensity (MFI) of their MHCII staining (right). FIG. 16G: Histograms show the expression of different co-stimulatory or co-inhibitory molecules on gated EGFP+ skin ILCs of CCR10$^{+/EGFP}$ mice. Gray histograms are of the staining with isotype control antibodies. FIG. 16H: Representative flow cytometric analysis of CCR10 (EGFP) expression on ILCs of skin lymph nodes (sLN), bone marrow (BM), spleen and mesenteric lymph nodes (mLN) of CCR10$^{+/EGFP}$ mice. Gate and analysis strategies are similar to those in the FIG. 16A. N>30 for sLN and >10 for spleens, 2 for BM and mLN. FIG. 16I&J: Flow cytometric analysis of expression of CD127 and CD90 (i), CCR6, CD103 and CD69 (j) on EGFP+ and EGFP− sLN_ILCs of CCR10$^{+/EGFP}$ mice. N=3. FIG. 16k: Flow cytometric analysis of expression of CD44 and Ki-67 on EGFP+ and EGFP− sLN_ILCs of CCR10$^{+/EGFP}$ mice. N=5. Bar graph on the right shows percentages of Ki-67+ cells among EGFP+ and EGFP− sLN_ILCs. FIG. 16L: Flow cytometric analysis of expression of IL-17, IL-5, IFN-γ and IL-10 on EGFP+ and EGFP− sLN_ILCs of CCR10$^{+/EGFP}$ mice. Bar graphs on the right show percentages of IL-17+ (N=7) and IL-5+ (N=4) cells among sLN EGFP+ and EGFP− ILCs. N=2 for IFN-γ and IL-10. FIG. 16M: Flow cytometric analysis of MHCII expression on EGFP+ and EGFP− sLN_ILCs of CCR10$^{+/EGFP}$ mice. Bar graph shows percentages of MHCII+ cells in EGFP+ and EGFP− sLN_ILCs. N=4.

FIG. 17, comprising

FIG. 18, comprising FIG. 18A&B: Flow cytometric analysis of expression of CCR10 (EGFP) and MHCII on ILCs from the skin (A) and sLN (B) of CCR10$^{+/EGFP}$Rag1$^{-/-}$ mice. Plots in the left, gated on CD3−Lin− cells, identify CD3−Lin− ILCs. Plots in the right are gated on CD45+CD3−Lin− ILCs. N=3. FIG. 18C: Flow cytometric analysis of expression of Ki-67 and CD44 on sLN_ILCs of Rag1$^{-/-}$CCR10$^{+/EGFP}$ mice. N=3. FIG. 18D: Comparison of MFI of Ki67 and CD44 expressed on EGFP− sLN_ILCs of CCR10$^{+/EGFP}$ (WT) and Rag1$^{-/-}$ CCR10$^{+/EGFP}$ (Rag1$^{-/-}$) mice. N=3. FIG. 18E: Comparison of percentages of EGFP+ (left) and EGFP+MHCII+ (right) cells in skin_ILCs of CCR10$^{+/EGFP}$ (WT), Rag1$^{-/-}$ CCR10$^{+/EGFP}$ (Rag1$^{-/-}$) mice and Rag1$^{-/-}$CCR10$^{+/EGFP}$ mice transferred with total CD4+ cells (+total CD4) or Treg-depleted CD4+ cells (+Foxp3− CD4). For the transfer, equal numbers of total or Treg-depleted CD4+ T cells (CD3+CD4+EGFP− or CD3+CD4+Foxp3− RFP−CD62L+ EGFP−) were sorted from spleens of CCR10$^{+/EGFP}$ (CD45.1+CD45.2+) mice and injected into Rag1$^{-/-}$ CCR10$^{+/EGFP}$ (CD45.2+) mice. Host skin_ILCs were analyzed 6 weeks after transfer. N=6 for CCR10$^{+/EGFP}$ mice, 4 for Rag1$^{-/-}$CCR10$^{+/EGFP}$ mice, 5 each for Rag1$^{-/-}$ CCR10$^{+/EGFP}$ mice transferred with total or Treg-depleted CD4+ cells. FIG. 18F: Flow cytometric analysis of expression of CCR10 (EGFP) and MHCII on ILCs of sLN and the skin of Foxp3$^{-/-}$CCR10$^{+/EGFP}$ (Foxp3$^{-/-}$) mice. FIG. 18G: comparison of percentages of EGFP+sLN and skin ILCs between CCR10$^{+/EGFP}$ (WT) and Foxp3$^{-/-}$ CCR10$^{+/EGFP}$ (Foxp3$^{-/-}$) mice. N=4. FIG. 18H: Comparison of percentages of EGFP (CCR10)$^+$ cells among ILCs of sLN and the skin of untreated (ctrl, N=6) versus calcipotriol-treated CCR10$^{+/EGFP}$ mice (treated, N=7).

FIG. 19, comprising FIGS. 19A through 19C, is a series of images demonstrating that CCR10+ sILCs regulate homeostasis of CD4+ cells in the skin. FIG. 19A: Analysis of donor CD4$^+$ T cells for Foxp3$^+$ and EGFP$^+$ subsets in Rag1$^{-/-}$ and CCR10$^{EGFP/EGFP}$Rag1$^{-/-}$ recipient mice. CD3$^+$CD4$^+$EGFP$^-$ T cells sorted from spleens of CCR10$^{+/EGFP}$ (CD45.1$^+$CD45.2$^+$) mice were injected into Rag1$^{-/-}$ or CCR10$^{EGFP/EGFP}$Rag1$^{-/-}$ (CD45.2$^+$) mice. Donor CD4$^+$ T cells in the skin of recipients were analyzed by flow cytometry 6 weeks after transfer. Bar graphs show percentages of Foxp3$^+$ and EGFP$^+$ subpopulations among donor CD4$^+$ T cells in the skin of Rag1$^{-/-}$ (N=8) and CCR10$^{EGFP/EGFP}$Rag1$^{-/-}$ (N=9) recipients. FIG. 19B&C: Analysis of transferred CD4+ T cells in Rag1$^{-/-}$ and IL2Rγ$^{-/-}$Rag2$^{-/-}$ recipient mice. The transfer and analysis procedures of the donor CD4+ T cells in the FIG. 19B are similar as in the FIG. 19A. In addition, percentages of IL-17$^+$ subpopulation of donor Foxp3$^-$ CD4$^+$ T cells in the skin of recipients are determined in the FIG. 19C. N=5 each.

FIG. 20, comprising FIG. 20A: Flow cytometric analysis of skin immune cells of CCR10$^{+/-}$ and CCR10$^{-/-}$ mice for their ability to express IL-22 and IL-17. Gated on CD45+ cells. A representative of more than 5 experiments is shown. FIG. 20B: Flow cytometric analysis of skin immune cells of aged CCR10$^{+/-}$ and CCR10$^{-/-}$ mice (2 year-old) for their ability to express IL-17 and IFN-γ. Gated on CD45+CD3+ T cells. Note that all IL-17-producing T cells are lineage (Lin)-negative (γδ) T cells while most IFN-γ producing T cells are Lin+ (αβ) T cells. Representative of three experiments. FIG. 20C: Enlarged spleens of aged (2 year-old) CCR10$^{-/-}$ mice compared to those of CCR10$^{+/-}$ mice. Four spleens of CCR10$^{-/-}$ mice (right) and three of CCR10$^{+/-}$ mice (left) are shown. FIG. 20D: More severe psoriasis-like skin inflammatory symptoms on the skin of CCR10$^{-/-}$ mice compared to the CCR10$^{+/-}$ control 3-6 days after treatment of the skin with Imiquimod. Representative of three experiments.

FIG. 21, comprising FIG. 21A: Length of colons of CCR10$^{-/-}$ and CCR10$^{+/-}$ mice at ages of 2-3 and 9 months. One dot represents one mouse. Pictures of colons of CCR10$^{+/-}$ and CCR10$^{-/-}$ mice are shown at the right. FIG. 21B: Ratios of expression levels of different cytokine transcripts (determined by qRT-PCR) in colons of 9 month-old CCR10$^{-/-}$ over those of CCR10$^{+/-}$ mice (1 indicating no difference). N=8. FIG. 21C: Percentages of CCR10$^{+/-}$ and CCR10$^{-/-}$ mice with detectable fecal occult bleeding 3 days after starting DSS treatment. N=11 for CCR10$^{+/-}$ and N=13 for CCR10$^{-/-}$ mice. FIG. 21D: Survival rates of CCR10$^{+/-}$ and CCR10$^{-/-}$ mice after starting the DSS treatment. N=10 for CCR10$^{+/-}$ and N=9 for CCR10$^{-/-}$ mice. FIG. 21E: Ratios of expression levels of indicated cytokine transcripts in colons of CCR10$^{-/-}$ over those of CCR10$^{+/-}$ mice 7 days after starting DSS treatment. N=5.

FIG. 22, comprising FIG. 22A: Analysis of IL-17A, IFNγ, and IL-10 expression on total CD4$^+$ Li_LP T cells of CCR10$^{+/-}$ and CCR10$^{-/-}$ mice. N≥9 for IL-17A, N=4 for IFNγ, and N=15 for IL-10 analyses. FIG. 22B: Flow cytometric analysis of total Li_LP CD4$^+$ T cells of CCR10$^{+/-}$ and CCR10$^{-/-}$ mice for EGFP and Foxp3. Gated on CD4+ T cells. Average percentages of total and EGFP$^+$ Foxp3$^+$CD4$^+$ Treg cells, and EGFP$^+$ Foxp3$^-$CD4$^+$ Teff cells of CCR10$^{-/-}$ and CCR10$^{+/-}$ mice are shown in three bar graphs on the right. N≥7. FIG. 22C: Percentages of Foxp3$^+$ and Foxp3$^-$ Li_LP CD4$^+$ T cell subsets that express CCR10 (EGFP). N≥7. FIG. 22D: Flow cytometric analysis of Li_LP CCR10 (EGFP)+ CD3+CD4+ cells for the surface IgA signals. For this, the gated EGFP+CD3+ population (of the upper right histogram) is analyzed for CD4 and IgA signals (in the lower left histogram). The expression of IgA on the CD3− EGFP+ (mostly IgA+ cells, upper left histogram) and CD3+ EGFP− (lower right histogram) populations is also analyzed as controls. FIG. 22E: FlowSight image analysis of cell interaction of intestinal EGFP+ IgA+ cells and EGFP−CD3+ T cells. Cellular events that are positive for both EGFP and CD3 are analyzed using an Amnis FlowSight image cytometer. Note that EGFP+CD3+ cellular events are composed of two interacting cells (bright field images on the left). In addition, EGFP signals come from IgA+ cells but not from CD3+ cells of the 2-cell conjugates. Two representatives of more than 30 analyses.

DETAILED DESCRIPTION OF THE INVENTION

Figures 1A, 1B, 1C, 1D, 1E, 1F:
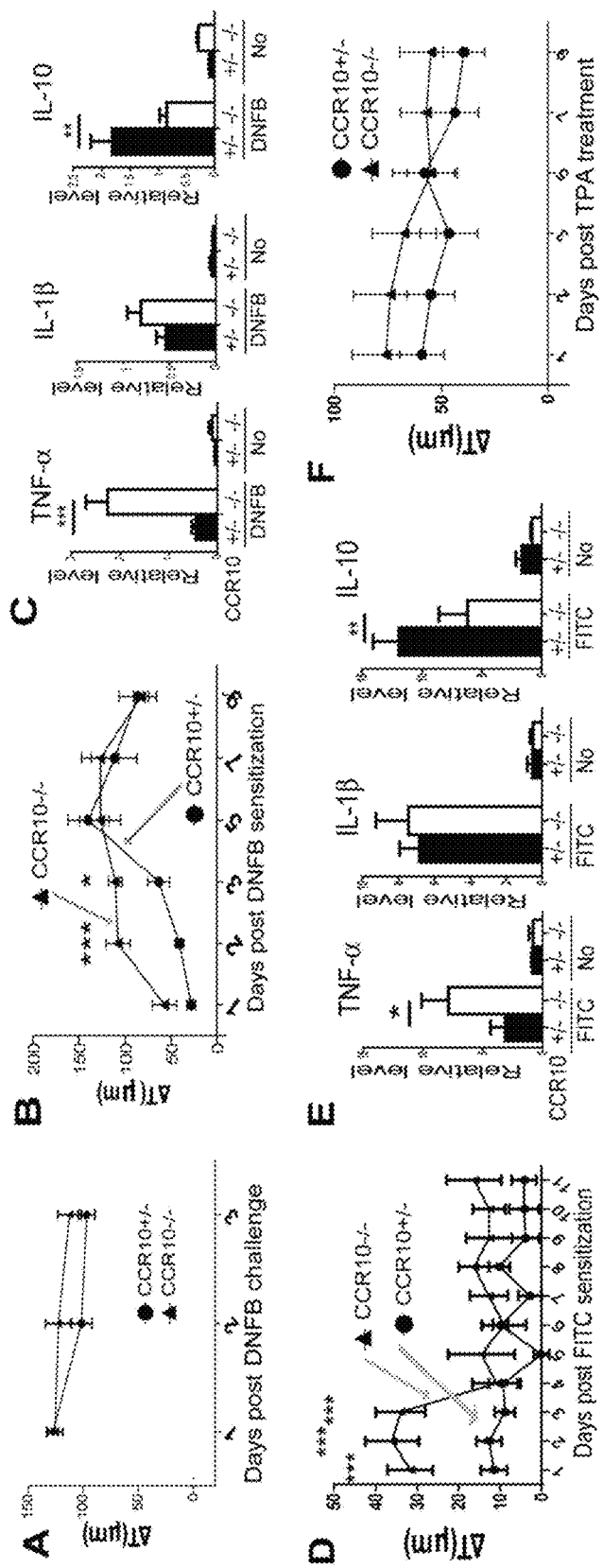
FIGS. 1A through 1F, is a series of images demonstrating over-reactive innate response to stimulation in skin of CCR10$^{-/-}$ mice.

The invention provides for compositions and methods for regulating skin and intestinal diseases by modulating CCR10-associated signals or cells. The invention is based on the discovery that targeting CCR10 and/or the CCR10/ligand axis is linked to modulating the immune response in a subject.

Accordingly, the invention provides compositions and methods for targeting one or more of CCR10, CCR10/ligand axis, and their functional equivalents for modulating an immune response in a subject. That is, the invention is based on the novel discovery that CCR10 plays a role in regulating function of the skin and intestinal T and/or ILC cells to maintain immune homeostasis and prevent overactive immune responses in local tissues of skin and intestines. Therefore, by inhibiting one or more of CCR10, CCR10/ligand axis, and their functional equivalents, an immune response can be enhanced in a subject to treat, for example, diseases and disorders where the immune response is suppressed, including but not limited to skin-specific infections by parasites and cancers. Alternatively, by activating one or more of CCR10, CCR10/ligand axis, and their functional equivalents, an immune response can be diminished in a subject to treat, for example, diseases and disorders associated with hyperactive or otherwise undesirable immune response, including but not limited to autoimmune diseases.

In one embodiment, the invention provides compositions and methods for modulating one or more of the level, production, and activity of one or more of CCR10, CCR10/ligand axis, and their functional equivalents. In the context of treating a disease where the immune response is suppressed, the invention provides compositions and methods for inhibiting one or more of the level, production, and activity of one or more of CCR10, CCR10/ligand axis, and their functional equivalents thereby enhancing the immune response. In the context of treating a disease associated with an undesirable immune response, the invention provides compositions and methods for increasing one or more of the level, production, and activity of one or more of CCR10, CCR10/ligand axis, and their functional equivalents or CCR10+ T and/or ILC cells thereby diminishing the immune response.

Accordingly, the invention provides activators (e.g., agonists) and inhibitors (e.g., antagonists) of one or more of CCR10, CCR10/ligand axis, and their functional equivalents. In one embodiment, the activator of the invention includes but is not limited to a small molecule, a chemical compound, a protein, a peptide, a peptidomemetic, a nucleic acid, and the like. In one embodiment, the inhibitor of the invention includes but is not limited to an antibody or a fragment thereof, a peptide, a nucleic acid, small molecule, a chemical compound, and the like.

In one embodiment, the present invention comprises a method for increasing one or more of the level, production, and activity of one or more of CCR10, CCR10/ligand axis, and their functional equivalents comprising administering to a subject an effective amount of a composition comprising an activator of one or more of CCR10, CCR10/ligand axis, and their functional equivalents. In an embodiment of the present invention, the composition increases the transcription of one or more of CCR10, CCR10/ligand axis, and their functional equivalents or translation of one or more of CCR10, CCR10/ligand axis, and their functional equivalents. In another embodiment of the present invention, the composition increases the activity of one or more of CCR10, CCR10/ligand axis, and their functional equivalents.

An aspect of the present invention comprises a method for decreasing one or more of the level, production, and activity of one or more of CCR10, CCR10/ligand axis, and their functional equivalents comprising administering to a subject an effective amount of a composition comprising an inhibitor of one or more of CCR10, CCR10/ligand axis, and their functional equivalents. In an embodiment of the present invention, the composition decreases the transcription of one or more of CCR10, CCR10/ligand axis, and their functional equivalents or translation of one or more of CCR10, CCR10/ligand axis, and their functional equivalents. In another embodiment of the present invention, the composition inhibits the activity of one or more of CCR10, CCR10/ligand axis, and their functional equivalents.

Another aspect of the present invention comprises a pharmaceutical composition comprising a modulator (e.g., activator or inhibitor) of one or more of CCR10, CCR10/ligand axis, and their functional equivalents. In one embodiment, the composition of the invention can be used in combination with another therapeutic agent.

In one embodiment, the invention provides compositions and methods for treating skin diseases associated with an ineffective immune response. In another embodiment, treatment of the skin disease is accomplished by inducing an enhanced immune response.

In one embodiment, the present invention provides compositions and methods for enhancing an immune response in a subject by modulating one or more of CCR10, CCR10/ligand axis, and their functional equivalents. The present invention includes the use of the compounds of the invention in combination with vaccines and other therapies in which it is desirable to enhance the immune response by inhibiting one or more of CCR10, CCR10/ligand axis, and their functional equivalents.

In addition, the present invention also provides compositions and methods for breaking self-tolerance in tumor vaccination. Therefore the present invention includes a therapeutic benefit of enhancing the immune response in a subject by interfering with one or more of CCR10, CCR10/ligand axis, and their functional equivalents.

In one embodiment, the invention provides compositions and methods for treating an autoimmune disease. In one embodiment, the autoimmune disease is psoriasis. In another embodiment, the autoimmune disease is autoimmune intestinal inflammation. Therefore the present invention includes a therapeutic benefit of inhibiting the immune response in a subject by activating one or more of CCR10, CCR10/ligand axis, and their functional equivalents.

Definitions

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 2001, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, scFv antibodies, and multispecific antibodies formed from antibody fragments.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. κ and λ light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

"Antisense" refers particularly to the nucleic acid sequence of the non-coding strand of a double stranded DNA molecule encoding a polypeptide, or to a sequence which is substantially homologous to the non-coding strand. As defined herein, an antisense sequence is complementary to the sequence of a double stranded DNA molecule encoding a polypeptide. It is not necessary that the antisense sequence be complementary solely to the coding portion of the coding strand of the DNA molecule. The antisense sequence may be complementary to regulatory sequences specified on the coding strand of a DNA molecule encoding a polypeptide, which regulatory sequences control expression of the coding sequences.

As used herein, the term "autologous" is meant to refer to any material derived from the same individual to which it is later to be re-introduced into the individual.

"Allogeneic" refers to a graft derived from a different animal of the same species.

The term "B-cell" as used herein is defined as a cell derived from the bone marrow and/or spleen. B cells can develop into plasma cells which produce antibodies.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

The term "CCR10-mediated disorder" refers to disease states and/or symptoms associated with CCR10-mediated infections, cancers or tumors. In general, the term "CCR10-mediated disorder" refers to any disorder, the onset, progression or the persistence of the symptoms of which requires the participation of CCR10. Exemplary CCR10-mediated disorders include, but are not limited to, infection and cancer.

The term "CCR10/ligand axis" refers to the signaling pathway associated with the chemokine/receptor pair of skin-associated chemokine CCL27 (also called CTACK, ALP and ESkine) and its receptor CCR10 (GPR-2).

As used herein, an "effector cell" refers to a cell which mediates an immune response against an antigen. An example of an effector cell includes, but is not limited to a T cell and a B cell.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

The term "effector cell" refers to a cell which mediates an immune response against an antigen. An example of an effector cell includes, but is not limited to, a T cell or a B cell.

As used herein, the term "exogenous" refers to any material introduced from or produced outside an organism, cell, tissue or system.

The term "expression" as used herein is defined as the transcription and/or translation of a particular nucleotide sequence driven by its promoter.

The term "expression vector" as used herein refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules, siRNA, ribozymes, and the like. Expression vectors can contain a variety of control sequences, which refer to nucleic acid sequences necessary for the transcription and possibly translation of an operatively linked coding sequence in a particular host organism. In addition to control sequences that govern transcription and translation, vectors and expression vectors may contain nucleic acid sequences that serve other functions as well.

The term "heterologous" as used herein is defined as DNA or RNA sequences or proteins that are derived from the different species.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 5'-ATTGCC-3' and 5'-TATGGC-3' share 50% homology.

As used herein, "homology" is used synonymously with "identity."

The term "immunoglobulin" or "Ig", as used herein is defined as a class of proteins, which function as antibodies. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most mammals. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

As used herein, the term "immune response" includes, but is not limited to, T cell-mediated and/or B cell-mediated immune responses that are influenced by modulation of T cell costimulation. Exemplary immune responses include B cell responses (e.g., antibody production) T cell responses (e.g., cytokine production, and cellular cytotoxicity) and activation of cytokine responsive cells, e.g., macrophages.

As used herein, the term "immune cell" is intended to include, but is not limited to, a cell that is of hematopoietic origin and that plays a role in the immune response. Immune cells include, but are not limited to, lymphocytes, such as B cells and T cells; natural killer cells; and myeloid cells, such as monocytes, macrophages, eosinophils, mast cells, basophils, and granulocytes.

An "isolated nucleic acid" refers to a nucleic acid segment or fragment which has been separated from sequences which flank it in a naturally occurring state, i.e., a DNA fragment which has been removed from the sequences which are normally adjacent to the fragment, i.e., the sequences adjacent to the fragment in a genome in which it naturally occurs. The term also applies to nucleic acids which have been substantially purified from other components which naturally accompany the nucleic acid, i.e., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (i.e., as a cDNA or a genomic or cDNA fragment produced by PCR or restriction enzyme digestion) independent of other sequences. It also includes a recombinant DNA which is part of a hybrid gene encoding additional polypeptide sequence.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

As used herein, the term "modulate" is meant to refer to any change in biological state, i.e. increasing, decreasing, and the like. For example, the term "modulate" refers to the ability to regulate positively or negatively the expression or activity of CCR10, including but not limited to transcription of CCR10 mRNA, stability of CCR10 mRNA, translation of CCR10 mRNA, stability of CCR10 polypeptide, CCR10 post-translational modifications, or any combination thereof. Further, the term modulate can be used to refer to an increase, decrease, masking, altering, overriding or restoring of activity, including but not limited to, CCR10 activity associated with immunogenicity of a cell.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

The term "polypeptide" as used herein is defined as a chain of amino acid residues, usually having a defined sequence. As used herein the term polypeptide is mutually inclusive of the terms "peptide" and "protein."

As used herein, a "peptidomimetic" is a compound containing non-peptidic structural elements that is capable of mimicking the biological action of a parent peptide. A peptidomimetic may or may not comprise peptide bonds.

"Proliferation" is used herein to refer to the reproduction or multiplication of similar forms of entities, for example proliferation of a cell. That is, proliferation encompasses production of a greater number of cells, and can be measured by, among other things, simply counting the numbers of cells, measuring incorporation of $^3$H-thymidine into the cell, and the like.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

The term "RNA" as used herein is defined as ribonucleic acid.

The term "self-antigen" as used herein is defined as an antigen that is expressed by a host cell or tissue. Self-antigens may be tumor antigens, but in certain embodiments, are expressed in both normal and tumor cells. A skilled artisan would readily understand that a self-antigen may be overexpressed in a cell.

The terms "subject," "patient," "individual," and the like are used interchangeably herein, and refer to any animal, or cells thereof whether in vitro or in situ, amenable to the methods described herein. In certain non-limiting embodiments, the patient, subject or individual is a human.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are culture in vitro. In other embodiments, the cells are not cultured in vitro.

The term "T-cell" as used herein is defined as a *thymus*-derived cell that participates in a variety of cell-mediated immune reactions.

The term "T-helper" as used herein with reference to cells indicates a sub-group of lymphocytes (a type of white blood cell or leukocyte) including different cell types identifiable by a skilled person. In particular, T-helper cell according to the present disclosure include effector $T_h$ cells (such as Th1, Th2 and Th17). These Th cells secrete cytokines, proteins or peptides that stimulate or interact with other leukocytes.

The term "regulatory T cell" or "Treg cell" refers to a naturally occurring subtype of T cell that can inhibit T-cell immune responses to an antigen. Treg cells represent a distinct T-cell lineage that has a key role in an individual's tolerance of self-antigens and the prevention of autoimmune disease and inappropriate immune responses. When activated, they are anergic and suppress the proliferation and cytokine production of conventional T cells. Like all T cells, Treg cells require T cell receptor activation and costimulation to become fully active.

"Therapeutically effective amount" is an amount of a compound of the invention, that when administered to a patient, ameliorates a symptom of the disease. The amount of a compound of the invention which constitutes a "therapeutically effective amount" will vary depending on the compound, the disease state and its severity, the age of the patient to be treated, and the like. The therapeutically effective amount can be determined routinely by one of ordinary skill in the art having regard to his own knowledge and to this disclosure.

"Patient" for the purposes of the present invention includes humans and other animals, particularly mammals, and other organisms. Thus the methods are applicable to both human therapy and veterinary applications. In a preferred embodiment the patient is a mammal, and in a most preferred embodiment the patient is human.

The terms "treat," "treating," and "treatment," refer to therapeutic or preventative measures described herein. The methods of "treatment" employ administration to a subject, in need of such treatment, a composition of the present invention, for example, a subject having a disorder mediated by CCR10 or other oncoprotein or a subject who ultimately may acquire such a disorder, in order to prevent, cure, delay, reduce the severity of, or ameliorate one or more symptoms of the disorder or recurring disorder, or in order to prolong the survival of a subject beyond that expected in the absence of such treatment.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The phrase "under transcriptional control" or "operatively linked" as used herein means that the promoter is in the correct location and orientation in relation to a polynucleotide to control the initiation of transcription by RNA polymerase and expression of the polynucleotide.

The term "vaccine" as used herein is defined as a material used to provoke an immune response after administration of the material to a mammal.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The disclosure presented herein demonstrates a new role for CCR10 in the maintenance and function of the resident regulatory T (Treg) vs. effector T (Teff) cells. For example, the invention is based on the surprising discovery that CCR10 plays a role in a positive feedback circuit of immune homeostatic regulation in the skin where CCR10 maintains balanced presence and function of resident Treg vs. Teff cells, which in turn establishes a homeostatic environment important for maintenance of the CCR10+ resident T cells. Accordingly, the invention includes compositions and methods for targeting CCR10 for drug therapy. In some instances, inhibiting CCR10 is useful in increasing the immune response and therefore allowing the immune system to respond to the target. In some instances, activating CCR10 is useful in inhibiting the immune response.

The present invention provides compounds and methods for inhibiting CCR10, such as the CCR10/ligand axis and methods of treating diseases mediated by activity of CCR10 and functionally equivalents thereof using the compounds of the invention. The invention also provides compounds and methods of inhibiting downstream targets of CCR10 and its functional equivalents. Diseases mediated by CCR10 and functionally equivalents thereof include, but are not limited to, diseases characterized in part by abnormalities in optimal immune reaction, infection, cancer, and the like.

The present invention provides compounds and methods for activating CCR10, such as the CCR10/ligand axis and methods of treating diseases mediated by activity of CCR10 and functionally equivalents thereof using the compounds of the invention. The invention also provides compounds and methods of activating downstream targets of CCR10 and its functional equivalents. Diseases mediated by CCR10 and functionally equivalents thereof include, but are not limited to, autoimmune disease and diseases associated with hyperactive immune response.

Compositions

In one embodiment, the invention provides a modulator (e.g., an inhibitor or activator) of one or more of CCR10, a ligand of CCR10, and a down-stream effector protein in the CCR10/ligand axis. In various embodiments, the present invention includes compositions for modulating the level or activity of one or more of CCR10, a ligand of CCR10, and a down-stream effector protein in the CCR10/ligand axis in a subject, a cell, a tissue, or an organ in need thereof. In various embodiments, the compositions of the invention modulates the amount of polypeptide of one or more of CCR10, a ligand of CCR10, and a down-stream effector protein in the CCR10/ligand axis, the amount of mRNA of one or more of CCR10, a ligand of CCR10, and a down-stream effector protein in the CCR10/ligand axis, the amount of activity of one or more of CCR10, a ligand of CCR10, and a down-stream effector protein in the CCR10/ligand axis, or a combination thereof.

In one embodiment, an inhibitor of the invention is useful for treating treat, for example, diseases and disorders where the immune response is suppressed, including but not limited to skin-specific infections by parasites and cancers. In one embodiment, an activator of the invention is useful for treating for example, diseases and disorders associated with hyperactive or otherwise undesirable immune response, including but not limited to autoimmune diseases.

Inhibitors

As described elsewhere herein, the invention is based on the discovery that inhibition of CCR10 enhances the immune response in a subject. This observation is the first of its kind by providing a direct link between function of CCR10 in a positive feedback circuit of immune homeostatic regulation in the skin where CCR10 maintains balanced presence and function of resident Treg vs. Teff cells, which in turn help to establish a homeostatic environment important for maintenance of the CCR10+ resident T cells. As such the invention provides compositions and methods for therapeutic inhibition of CCR10 in a subject. The results presented herein also provide for combining any immunotherapy protocols in diseases such as skin infection and cancer with inhibitors of the invention that targets CCR10.

The present invention relates to the discovery that inhibition of one or more of CCR10, CCR10/ligand axis, and their functional equivalents provides a therapeutic benefit. Thus, the invention comprises compositions and methods for inhibiting any of these components in cell or animal thereby enhancing an immune response in the animal.

Based on the disclosure herein, the present invention includes a generic concept for inhibiting CCR10 or any component of the signal transduction pathway associated with CCR10 or a functional equivalent thereof.

In one embodiment, the invention comprises a composition for enhancing an immune response. The composition comprises an inhibitor of any one or more of CCR10, CCR10/ligand axis, and their functional equivalents. In one embodiment, composition comprising an inhibitor wherein the inhibitor includes but is not limited to a small interfering RNA (siRNA), a microRNA, an antisense nucleic acid, a ribozyme, an expression vector encoding a transdominant negative mutant, an intracellular antibody, a peptide and a small molecule.

By way of a non-limiting example, siRNA is a type of molecule that can inhibit CCR10. An siRNA polynucleotide is an RNA nucleic acid molecule that interferes with RNA activity that is generally considered to occur via a post-transcriptional gene silencing mechanism. An siRNA polynucleotide preferably comprises a double-stranded RNA (dsRNA) but is not intended to be so limited and may comprise a single-stranded RNA (see, e.g., Martinez et al., 2002 Cell 110:563-74). The siRNA polynucleotide included in the invention may comprise other naturally occurring, recombinant, or synthetic single-stranded or double-stranded polymers of nucleotides (ribonucleotides or deoxyribonucleotides or a combination of both) and/or nucleotide analogues as provided herein (e.g., an oligonucleotide or polynucleotide or the like, typically in 5' to 3' phosphodiester linkage). Accordingly it will be appreciated that certain exemplary sequences disclosed herein as DNA sequences capable of directing the transcription of the siRNA polynucleotides are also intended to describe the corresponding RNA sequences and their complements, given the well-established principles of complementary nucleotide base-pairing.

Preferred siRNA polynucleotides comprise double-stranded polynucleotides of about 18-30 nucleotide base pairs, preferably about 18, about 19, about 20, about 21, about 22, about 23, about 24, about 25, about 26, or about 27 base pairs, and in other preferred embodiments about 19, about 20, about 21, about 22 or about 23 base pairs, or about 27 base pairs, whereby the use of "about" indicates that in certain embodiments and under certain conditions the processive cleavage steps that may give rise to functional siRNA polynucleotides that are capable of interfering with expression of a selected polypeptide may not be absolutely efficient. Hence, siRNA polynucleotides, may include one or more siRNA polynucleotide molecules that may differ (e.g., by nucleotide insertion or deletion) in length by one, two, three, four or more base pairs as a consequence of the variability in processing, in biosynthesis, or in artificial synthesis of the siRNA. The siRNA polynucleotide of the present invention may also comprise a polynucleotide sequence that exhibits variability by differing (e.g., by nucleotide substitution, including transition or transversion) at one, two, three or four nucleotides from a particular sequence. These differences can occur at any of the nucleotide positions of a particular siRNA polynucleotide sequence, depending on the length of the molecule, whether situated in a sense or in an antisense strand of the double-stranded polynucleotide. The nucleotide difference may be found on one strand of a double-stranded polynucleotide, where the complementary nucleotide with which the substitute nucleotide would typically form hydrogen bond base pairing, may not necessarily be correspondingly substituted.

In preferred embodiments, the siRNA polynucleotides are homogeneous with respect to a specific nucleotide sequence.

Based on the present disclosure, it should be appreciated that the siRNAs of the present invention may effect silencing of the target polypeptide expression to different degrees. The siRNAs thus must first be tested for their effectiveness. Selection of siRNAs is made therefrom based on the ability of a given siRNA to interfere with or modulate the expression of the target polypeptide. Accordingly, identification of specific siRNA polynucleotide sequences that are capable of interfering with expression of a desired target polypeptide requires production and testing of each siRNA. The methods for testing each siRNA and selection of suitable siRNAs for use in the present invention are fully set forth herein the Examples. Since not all siRNAs that interfere with protein expression will have a physiologically important effect, the present disclosure also sets forth various physiologically relevant assays for determining whether the levels of interference with target protein expression using the siRNAs of the invention have clinically relevant significance.

One skilled in the art will readily appreciate that as a result of the degeneracy of the genetic code, many different nucleotide sequences may encode the same polypeptide. That is, an amino acid may be encoded by one of several different codons, and a person skilled in the art can readily determine that while one particular nucleotide sequence may differ from another, the polynucleotides may in fact encode polypeptides with identical amino acid sequences. As such, polynucleotides that vary due to differences in codon usage are specifically contemplated by the present invention.

One skilled in the art will appreciate, based on the disclosure provided herein, that one way to decrease the mRNA and/or protein levels of one or more of CCR10, CCR10/ligand axis, and their functional equivalents is by reducing or inhibiting expression of the nucleic acid encoding CCR10 or any component of the signal transduction pathway associated with CCR10 or a functional equivalent thereof. Thus, the protein level of CCR10 or any component of the signal transduction pathway associated with CCR10 or a functional equivalent thereof in a cell can also be decreased using a molecule or compound that inhibits or reduces gene expression such as, for example, an antisense molecule or a ribozyme.

In a preferred embodiment, the modulating sequence is an antisense nucleic acid sequence which is expressed by a plasmid vector. The antisense expressing vector is used to transfect a mammalian cell or the mammal itself, thereby causing reduced endogenous expression of a desired regulator in the cell. However, the invention should not be construed to be limited to inhibiting expression of a regulator by transfection of cells with antisense molecules. Rather, the invention encompasses other methods known in the art for inhibiting expression or activity of a protein in the cell including, but not limited to, the use of a ribozyme, the expression of a non-functional regulator (i.e. transdominant negative mutant) and use of an intracellular antibody.

Antisense molecules and their use for inhibiting gene expression are well known in the art (see, e.g., Cohen, 1989, In: Oligodeoxyribonucleotides, Antisense Inhibitors of Gene Expression, CRC Press). Antisense nucleic acids are DNA or RNA molecules that are complementary, as that term is defined elsewhere herein, to at least a portion of a specific mRNA molecule (Weintraub, 1990, Scientific American 262:40). In the cell, antisense nucleic acids hybridize to the corresponding mRNA, forming a double-stranded molecule thereby inhibiting the translation of genes.

The use of antisense methods to inhibit the translation of genes is known in the art, and is described, for example, in Marcus-Sakura (1988, Anal. Biochem. 172:289). Such antisense molecules may be provided to the cell via genetic expression using DNA encoding the antisense molecule as taught by Inoue, 1993, U.S. Pat. No. 5,190,931.

Alternatively, antisense molecules of the invention may be made synthetically and then provided to the cell. Antisense oligomers of between about 10 to about 30, and more preferably about 15 nucleotides, are preferred, since they are easily synthesized and introduced into a target cell. Synthetic antisense molecules contemplated by the invention include oligonucleotide derivatives known in the art which have improved biological activity compared to unmodified oligonucleotides (see U.S. Pat. No. 5,023,243).

Ribozymes and their use for inhibiting gene expression are also well known in the art (see, e.g., Cech et al., 1992, J. Biol. Chem. 267:17479-17482; Hampel et al., 1989, Biochemistry 28:4929-4933; Eckstein et al., International Publication No. WO 92/07065; Altman et al., U.S. Pat. No. 5,168,053). Ribozymes are RNA molecules possessing the ability to specifically cleave other single-stranded RNA in a manner analogous to DNA restriction endonucleases. Through the modification of nucleotide sequences encoding these RNAs, molecules can be engineered to recognize specific nucleotide sequences in an RNA molecule and cleave it (Cech, 1988, J. Amer. Med. Assn. 260:3030). A major advantage of this approach is the fact that ribozymes are sequence-specific.

There are two basic types of ribozymes, namely, tetrahymena-type (Hasselhoff, 1988, Nature 334:585) and hammerhead-type. Tetrahymena-type ribozymes recognize sequences which are four bases in length, while hammerhead-type ribozymes recognize base sequences 11-18 bases in length. The longer the sequence, the greater the likelihood that the sequence will occur exclusively in the target mRNA species. Consequently, hammerhead-type ribozymes are preferable to tetrahymena-type ribozymes for inactivating specific mRNA species, and 18-base recognition sequences are preferable to shorter recognition sequences which may occur randomly within various unrelated mRNA molecules.

Ribozymes useful for inhibiting the expression of a regulator may be designed by incorporating target sequences into the basic ribozyme structure which are complementary to the mRNA sequence of the desired regulator of the present invention, including but are not limited to, CCR10 or any component of the signal transduction pathway associated with CCR10 or a functional equivalent thereof. Ribozymes targeting the desired regulator may be synthesized using commercially available reagents (Applied Biosystems, Inc., Foster City, Calif.) or they may be genetically expressed from DNA encoding them.

In another aspect of the invention, the regulator can be inhibited by way of inactivating and/or sequestering the regulator. As such, inhibiting the effects of a regulator can be accomplished by using a transdominant negative mutant. Alternatively an antibody specific for the desired regulator, otherwise known as an antagonist to the regulator may be used. In one embodiment, the antagonist is a protein and/or compound having the desirable property of interacting with a binding partner of the regulator and thereby competing with the corresponding wild-type regulator. In another embodiment, the antagonist is a protein and/or compound having the desirable property of interacting with the regulator and thereby sequestering the regulator.

Antibodies

As will be understood by one skilled in the art, any antibody that can recognize and bind to an antigen of interest is useful in the present invention. That is, the antibody can inhibit CCR10 or its ligand CCL27 or any component of the signal transduction pathway associated with CCR10 or a functional equivalent thereof to provide a beneficial effect.

Methods of making and using antibodies are well known in the art. For example, polyclonal antibodies useful in the present invention are generated by immunizing rabbits according to standard immunological techniques well-known in the art (see, e.g., Harlow et al., 1988, In: Antibodies, A Laboratory Manual, Cold Spring Harbor, N.Y.). Such techniques include immunizing an animal with a chimeric protein comprising a portion of another protein such as a maltose binding protein or glutathione (GSH) tag polypeptide portion, and/or a moiety such that the antigenic protein of interest is rendered immunogenic (e.g., an antigen of interest conjugated with keyhole limpet hemocyanin, KLH) and a portion comprising the respective antigenic protein amino acid residues. The chimeric proteins are produced by cloning the appropriate nucleic acids encoding the marker protein into a plasmid vector suitable for this purpose, such as but not limited to, pMAL-2 or pCMX.

However, the invention should not be construed as being limited solely to methods and compositions including these antibodies or to these portions of the antigens. Rather, the invention should be construed to include other antibodies, as that term is defined elsewhere herein, to antigens, or portions thereof. Further, the present invention should be construed to encompass antibodies, inter alia, bind to the specific antigens of interest, and they are able to bind the antigen present on Western blots, in solution in enzyme linked immunoassays, in fluorescence activated cells sorting (FACS) assays, in magenetic-actived cell sorting (MACS) assays, and in immunofluorescence microscopy of a cell transiently transfected with a nucleic acid encoding at least a portion of the antigenic protein, for example.

One skilled in the art would appreciate, based upon the disclosure provided herein, that the antibody can specifically bind with any portion of the antigen and the full-length protein can be used to generate antibodies specific therefor. However, the present invention is not limited to using the full-length protein as an immunogen. Rather, the present invention includes using an immunogenic portion of the protein to produce an antibody that specifically binds with a specific antigen. That is, the invention includes immunizing an animal using an immunogenic portion, or antigenic determinant, of the antigen.

Once armed with the sequence of a specific antigen of interest and the detailed analysis localizing the various conserved and non-conserved domains of the protein, the skilled artisan would understand, based upon the disclosure provided herein, how to obtain antibodies specific for the various portions of the antigen using methods well-known in the art or to be developed.

The skilled artisan would appreciate, based upon the disclosure provided herein, that that present invention includes use of a single antibody recognizing a single antigenic epitope but that the invention is not limited to use of a single antibody. Instead, the invention encompasses use of at least one antibody where the antibodies can be directed to the same or different antigenic protein epitopes.

The generation of polyclonal antibodies is accomplished by inoculating the desired animal with the antigen and isolating antibodies which specifically bind the antigen therefrom using standard antibody production methods such as those described in, for example, Harlow et al. (1988, In: Antibodies, A Laboratory Manual, Cold Spring Harbor, N.Y.).

Monoclonal antibodies directed against full length or peptide fragments of a protein or peptide may be prepared using any well-known monoclonal antibody preparation procedures, such as those described, for example, in Harlow et al. (1988, In: Antibodies, A Laboratory Manual, Cold Spring Harbor, N.Y.) and in Tuszynski et al. (1988, Blood, 72:109-115). Quantities of the desired peptide may also be synthesized using chemical synthesis technology. Alternatively, DNA encoding the desired peptide may be cloned and expressed from an appropriate promoter sequence in cells suitable for the generation of large quantities of peptide. Monoclonal antibodies directed against the peptide are generated from mice immunized with the peptide using standard procedures as referenced herein.

Nucleic acid encoding the monoclonal antibody obtained using the procedures described herein may be cloned and sequenced using technology which is available in the art, and is described, for example, in Wright et al. (1992, Critical Rev. Immunol. 12:125-168), and the references cited therein. Further, the antibody of the invention may be "humanized" using the technology described in, for example, Wright et al., and in the references cited therein, and in Gu et al. (1997, Thrombosis and Hematocyst 77:755-759), and other methods of humanizing antibodies well-known in the art or to be developed.

The present invention also includes the use of humanized antibodies specifically reactive with epitopes of an antigen of interest. The humanized antibodies of the invention have a human framework and have one or more complementarity determining regions (CDRs) from an antibody, typically a mouse antibody, specifically reactive with an antigen of interest. When the antibody used in the invention is humanized, the antibody may be generated as described in Queen, et al. (U.S. Pat. No. 6,180,370), Wright et al., (supra) and in the references cited therein, or in Gu et al. (1997, Thrombosis and Hematocyst 77(4):755-759). The method disclosed in Queen et al. is directed in part toward designing humanized immunoglobulins that are produced by expressing recombinant DNA segments encoding the heavy and light chain complementarity determining regions (CDRs) from a donor immunoglobulin capable of binding to a desired antigen, such as an epitope on an antigen of interest, attached to DNA segments encoding acceptor human framework regions. Generally speaking, the invention in the Queen patent has applicability toward the design of substantially any humanized immunoglobulin. Queen explains that the DNA segments will typically include an expression control DNA sequence operably linked to the humanized immunoglobulin coding sequences, including naturally-associated or heterologous promoter regions. The expression control sequences can be eukaryotic promoter systems in vectors capable of transforming or transfecting eukaryotic host cells or the expression control sequences can be prokaryotic promoter systems in vectors capable of transforming or transfecting prokaryotic host cells. Once the vector has been incorporated into the appropriate host, the host is maintained under conditions suitable for high level expression of the introduced nucleotide sequences and as desired the collection and purification of the humanized light chains, heavy chains, light/heavy chain dimers or intact antibodies, binding fragments or other immunoglobulin forms may follow (Beychok, Cells of Immunoglobulin Synthesis, Academic Press, New York, (1979), which is incorporated herein by reference).

The invention also includes functional equivalents of the antibodies described herein. Functional equivalents have binding characteristics comparable to those of the antibodies, and include, for example, hybridized and single chain antibodies, as well as fragments thereof. Methods of producing such functional equivalents are disclosed in PCT Application WO 93/21319 and PCT Application WO 89/09622.

Functional equivalents include polypeptides with amino acid sequences substantially the same as the amino acid sequence of the variable or hypervariable regions of the antibodies. "Substantially the same" amino acid sequence is defined herein as a sequence with at least 70%, preferably at least about 80%, more preferably at least about 90%, even more preferably at least about 95%, and most preferably at least 99% homology to another amino acid sequence (or any integer in between 70 and 99), as determined by the FASTA search method in accordance with Pearson and Lipman, 1988 *Proc. Nat'l. Acad. Sci.* USA 85: 2444-2448. Chimeric or other hybrid antibodies have constant regions derived substantially or exclusively from human antibody constant regions and variable regions derived substantially or exclusively from the sequence of the variable region of a monoclonal antibody from each stable hybridoma.

Single chain antibodies (scFv) or Fv fragments are polypeptides that consist of the variable region of the heavy chain of the antibody linked to the variable region of the light chain, with or without an interconnecting linker. Thus, the Fv comprises an antibody combining site.

Functional equivalents of the antibodies of the invention further include fragments of antibodies that have the same, or substantially the same, binding characteristics to those of the whole antibody. Such fragments may contain one or both Fab fragments or the $F(ab')_2$ fragment. The antibody fragments contain all six complement determining regions of the whole antibody, although fragments containing fewer than all of such regions, such as three, four or five complement determining regions, are also functional. The functional equivalents are members of the IgG immunoglobulin class and subclasses thereof, but may be or may combine with any one of the following immunoglobulin classes: IgM, IgA, IgD, or IgE, and subclasses thereof. Heavy chains of various subclasses, such as the IgG subclasses, are responsible for different effector functions and thus, by choosing the desired heavy chain constant region, hybrid antibodies with desired effector function are produced. Exemplary constant regions are gamma 1 (IgG1), gamma 2 (IgG2), gamma 3 (IgG3), and gamma 4 (IgG4). The light chain constant region can be of the kappa or lambda type.

The immunoglobulins of the present invention can be monovalent, divalent or polyvalent. Monovalent immunoglobulins are dimers (HL) formed of a hybrid heavy chain associated through disulfide bridges with a hybrid light chain. Divalent immunoglobulins are tetramers ($H_2L_2$) formed of two dimers associated through at least one disulfide bridge.

Antagonists

Inhibitors of the invention can be any agent that inhibits any component of the CCR10/ligand axis. For example, the inhibitor of the invention includes, but is not limited to, a molecule that has an affinity for binding to CCR10 and/or CCL27 and inhibiting the CCR10:CCL27 pathway (e.g., CCR10/ligand axis).

In one embodiment, the invention provides inhibitors of the CCR10/ligand axis by blocking the interaction between CCR10 and its ligand CCL27. The blockage of the interaction between CCR10 and CCL27 can be accomplished using a ligand antagonist or receptor antagonist. Such may be ligand mutein antagonists, antibody antagonists to ligand or receptor, or drugs, e.g., small molecules, which block the chemoattraction between CCR10 and CCL27.

In one embodiment, the invention provides antagonists that block the signaling and/or effector biology of the CCR10/ligand axis in order to enhance the immune response. Antagonist activity may be tested or screened for using well known methods. Tests for ability to antagonize chemokine binding or chemoattractant activity can be developed. Various ligand homologs can be created which retain receptor binding capacity, but lack signaling capability, thus serving as competitive binding molecules. Small molecules may also be screened for ability to antagonize chemokine function, e.g., chemoattraction, receptor binding, and other effects mediated by chemokine.

Other binding compositions, which will often have similar uses, include molecules that bind with specificity to the receptor (e.g., CCR10) or the chemokine (e.g., CCL27), in a binding partner-binding partner fashion, an antibody-antigen interaction, a ligand:receptor interaction with or without signaling, or in a natural physiologically relevant protein-protein interaction, either covalent or non-covalent, e.g., proteins which specifically associate with chemokine receptor protein. The molecule may be a polymer, or chemical reagent. A functional analog may be a protein with structural modifications, or may be a structurally unrelated molecule, e.g., which has a molecular shape which interacts with the appropriate binding determinants.

Drug screening can be performed to identify compounds having capacity to bind to receptor, and/or to block chemoattraction to chemokine or the natural interaction with ligand. Subsequent biological assays can then be utilized to determine if the compound has intrinsic binding or blocking activity, e.g., an antagonist. Mutein antagonists may be developed which maintain receptor binding but lack signaling.

Structural studies of the ligands will lead to design of new variants, particularly analogs exhibiting antagonist properties on the receptor. This can be combined with previously described screening methods to isolate muteins exhibiting desired spectra of activities. Or ligands may be used to target or label receptor bearing cells.

As receptor specific binding molecules are provided, also included are small molecules identified by screening procedures. In particular, it is well known in the art how to screen for small molecules which interfere, e.g., with ligand binding to the receptor, often by specific binding to the receptor and blocking of binding by natural ligand. Such molecules may compete with natural ligands, and selectively bind to the respective chemokines (e.g., CCL27) or CCR10 receptor. Similarly, assays may be developed which can screen for blockage of downstream signaling pathways of the chemokine signaling pathways.

Activators

In various embodiments, the present invention includes compositions and methods of treating an autoimmune and inflammatory disorders including, but are not limited to, arthritic diseases such as rheumatoid arthritis, osteoarthritis, gouty arthritis, spondylitis; Behcet disease; sepsis, septic shock, endotoxic shock, gram negative sepsis, gram positive sepsis, and toxic shock syndrome; multiple organ injury syndrome secondary to septicemia, trauma, or hemorrhage; ophthalmic disorders such as allergic conjunctivitis, vernal conjunctivitis, uveitis, and thyroid-associated ophthalmopathy; eosinophilic granuloma; pulmonary or respiratory disorders such as asthma, chronic bronchitis, allergic rhinitis, ARDS, chronic pulmonary inflammatory disease (e.g., chronic obstructive pulmonary disease), silicosis, pulmonary sarcoidosis, pleurisy, alveolitis, vasculitis, pneumonia, bronchiectasis, and pulmonary oxygen toxicity; reperfusion injury of the myocardium, brain, or extremities; fibrosis such as cystic fibrosis; keloid formation or scar tissue formation; atherosclerosis; autoimmune diseases such as systemic lupus erythematosus (SLE), autoimmune thyroiditis, multiple sclerosis, some forms of diabetes, and Reynaud's syndrome; connective tissue disease, autoimmune pulmonary inflammation, Guillain Bane syndrome, autoimmune thyroiditis, insulin dependent diabetes mellitus, myasthenia gravis, graft versus host disease and autoimmune inflammatory eye disease; transplant rejection disorders such as GVHD and allograft rejection, chronic glomerulonephritis; inflammatory bowel diseases such as Crohn's disease, ulcerative colitis and necrotizing enterocolitis, inflammatory dermatoses such as contact dermatitis, atopic dermatitis, psoriasis, or urticarial; autoimmune intestinal inflammation; fever and myalgias due to infection; central or peripheral nervous system inflammatory disorders such as meningitis, encephalitis, and brain or spinal cord injury due to minor trauma; Sjorgren's syndrome; diseases involving leukocyte diapedesis; alcoholic hepatitis; bacterial pneumonia; antigen-antibody complex mediated diseases; hypovolemic shock; Type diabetes mellitus; acute and delayed hypersensitivity; disease states due to leukocyte dyscrasia and metastasis; thermal injury; granulocyte transfusion associated syndromes; cytokine-induced toxicity; and allergic reactions and conditions (e.g., anaphylaxis, serum sickness, drug reactions, food allergies, insect venom allergies, mastocytosis, allergic rhinitis, hypersensitivity pneumonitis, urticaria, angioedema, eczema, atopic dermatitis, allergic contact dermatitis, erythema multiform, Stevens Johnson syndrome, allergic conjunctivitis, atopic keratoconjunctivitis, venereal keratoconjunctivitis, giant papillary conjunctivitis and contact allergies), such as asthma (particularly allergic asthma) or other respiratory problems.

It will be understood by one skilled in the art, based upon the disclosure provided herein, that an increase in the level of any one or more of CCR10, CCR10/ligand axis, and their functional equivalents encompasses the increase in expression, including transcription, translation, or both of any one or more of CCR10, CCR10/ligand axis, and their functional equivalents. The skilled artisan will also appreciate, once armed with the teachings of the present invention, that an increase in the level of any one or more of CCR10, CCR10/ligand axis, and their functional equivalents includes an increase in activity of any one or more of CCR10, CCR10/ligand axis, and their functional equivalents. Thus, increasing the level or activity of any one or more of CCR10, CCR10/ligand axis, and their functional equivalents includes, but is not limited to, increasing the amount of polypeptide, increasing transcription, translation, or both, of a nucleic acid encoding one or more of CCR10, CCR10/ligand axis, and their functional equivalents; and it also includes increasing any activity of any one or more of CCR10, CCR10/ligand axis, and their functional equivalents as well.

Thus, the present invention relates to the prevention and treatment of a desired autoimmune or inflammatory disease or disorder by administration of a polypeptide, a recombinant polypeptide, an active polypeptide fragment, or an activator of expression or activity of one or more of CCR10, CCR10/ligand axis, and their functional equivalents.

It is understood by one skilled in the art, that an increase in the level of, for example, CCR10 encompasses the increase of CCR10 protein expression. Additionally, the skilled artisan would appreciate, that an increase in the level of CCR10 includes an increase in CCR10 activity. Thus, increasing the level or activity of CCR10 includes, but is not limited to, increasing transcription, translation, or both, of a nucleic acid encoding CCR10; and it also includes increasing any activity of CCR10 as well.

Activation of CCR10 can be assessed using a wide variety of methods, including those disclosed herein, as well as methods well-known in the art or to be developed in the future. That is, the routineer would appreciate, based upon the disclosure provided herein, that increasing the level or activity of CCR10 can be readily assessed using methods that assess the level of a nucleic acid encoding CCR10 (e.g., mRNA) and/or the level of CCR10 polypeptide in a biological sample obtained from a subject.

A CCR10 activator can include, but should not be construed as being limited to, a chemical compound, a protein, a peptidomemetic, an antibody, a nucleic acid molecule. One of skill in the art would readily appreciate, based on the disclosure provided herein, that a CCR10 activator encompasses a chemical compound that increases the level, enzymatic activity, or the like of CCR10. Additionally, a CCR10 activator encompasses a chemically modified compound, and derivatives, as is well known to one of skill in the chemical arts.

It will be understood by one skilled in the art, based upon the disclosure provided herein, that an increase in the level of CCR10 encompasses the increase in CCR10 expression, including transcription, translation, or both. The skilled artisan will also appreciate, once armed with the teachings of the present invention, that an increase in the level of CCR10 includes an increase in CCR10 activity (e.g., enzymatic activity, receptor binding activity, etc.). Thus, increasing the level or activity of CCR10 includes, but is not limited to, increasing the amount of CCR10 polypeptide, increasing transcription, translation, or both, of a nucleic acid encoding CCR10; and it also includes increasing any activity of a CCR10 polypeptide as well. The CCR10 activator compositions and methods of the invention can selectively activate CCR10.

Further, one of skill in the art would, when equipped with this disclosure and the methods exemplified herein, appreciate that a CCR10 activator includes such activators as discovered in the future, as can be identified by well-known criteria in the art of pharmacology, such as the physiological results of activation of CCR10 as described in detail herein and/or as known in the art. Therefore, the present invention is not limited in any way to any particular CCR10 activator as exemplified or disclosed herein; rather, the invention encompasses those activators that would be understood by the routineer to be useful as are known in the art and as are discovered in the future.

Further methods of identifying and producing a CCR10 activator are well known to those of ordinary skill in the art, including, but not limited, obtaining an activator from a naturally occurring source. Alternatively, a CCR10 activator can be synthesized chemically. Further, the routineer would appreciate, based upon the teachings provided herein, that a CCR10 activator can be obtained from a recombinant organism. Compositions and methods for chemically synthesizing CCR10 activators and for obtaining them from natural sources are well known in the art and are described in the art.

One of skill in the art will appreciate that an activator can be administered as a small molecule chemical, a protein, a nucleic acid construct encoding a protein, or combinations thereof. Numerous vectors and other compositions and methods are well known for administering a protein or a nucleic acid construct encoding a protein to cells or tissues. Therefore, the invention includes a method of administering a protein or a nucleic acid encoding a protein that is an activator of CCR10.

One of skill in the art will realize that diminishing the amount or activity of a molecule that itself diminishes the amount or activity of CCR10 can serve to increase the amount or activity of CCR10. Any inhibitor of a regulator of CCR10 is encompassed in the invention. As a non-limiting example, antisense is described as a form of inhibiting a regulator of CCR10 in order to increase the amount or activity of CCR10. Antisense oligonucleotides are DNA or RNA molecules that are complementary to some portion of a mRNA molecule. When present in a cell, antisense oligonucleotides hybridize to an existing mRNA molecule and inhibit translation into a gene product Inhibiting the expression of a gene using an antisense oligonucleotide is well known in the art (Marcus-Sekura, 1988, Anal. Biochem. 172:289), as are methods of expressing an antisense oligonucleotide in a cell (Inoue, U.S. Pat. No. 5,190,931). The methods of the invention include the use of antisense oligonucleotide to diminish the amount of a molecule that causes a decrease in the amount or activity CCR10, thereby increasing the amount or activity of CCR10. Contemplated in the present invention are antisense oligonucleotides that are synthesized and provided to the cell by way of methods well known to those of ordinary skill in the art. As an example, an antisense oligonucleotide can be synthesized to be between about 10 and about 100, more preferably between about 15 and about 50 nucleotides long. The synthesis of nucleic acid molecules is well known in the art, as is the synthesis of modified antisense oligonucleotides to improve biological activity in comparison to unmodified antisense oligonucleotides (Tullis, 1991, U.S. Pat. No. 5,023,243).

Similarly, the expression of a gene may be inhibited by the hybridization of an antisense molecule to a promoter or other regulatory element of a gene, thereby affecting the transcription of the gene. Methods for the identification of a promoter or other regulatory element that interacts with a gene of interest are well known in the art, and include such methods as the yeast two hybrid system (Bartel and Fields, eds., In: The Yeast Two Hybrid System, Oxford University Press, Cary, N.C.).

Alternatively, inhibition of a gene expressing a protein that diminishes the level or activity of CCR10 can be accomplished through the use of a ribozyme. Using ribozymes for inhibiting gene expression is well known to those of skill in the art (see, e.g., Cech et al., 1992, J. Biol. Chem. 267:17479; Hampel et al., 1989, Biochemistry 28: 4929; Altman et al., U.S. Pat. No. 5,168,053). Ribozymes are catalytic RNA molecules with the ability to cleave other single-stranded RNA molecules. Ribozymes are known to be sequence specific, and can therefore be modified to recognize a specific nucleotide sequence (Cech, 1988, J. Amer. Med. Assn. 260:3030), allowing the selective cleavage of specific mRNA molecules. Given the nucleotide sequence of the molecule, one of ordinary skill in the art could synthesize an antisense oligonucleotide or ribozyme without undue experimentation, provided with the disclosure and references incorporated herein.

One of skill in the art will appreciate that a CCR10 polypeptide, a recombinant CCR10 polypeptide, or an active CCR10 polypeptide fragment can be administered singly or in any combination thereof. Further, a CCR10 polypeptide, a recombinant CCR10 polypeptide, or an active CCR10 polypeptide fragment can be administered singly or in any combination thereof in a temporal sense, in that they may be administered simultaneously, before, and/or after each other. One of ordinary skill in the art will appreciate, based on the disclosure provided herein, that a CCR10 polypeptide, a recombinant CCR10 polypeptide, or an active CCR10 polypeptide fragment can be used to prevent or treat a neurodegenerative disease or disorder, and that an activator can be used alone or in any combination with another CCR10 polypeptide, recombinant CCR10 polypeptide, active CCR10 polypeptide fragment, or CCR10 activator to effect a therapeutic result.

One of skill in the art, when armed with the disclosure herein, would appreciate that the treating a neurodegenerative disease or disorder encompasses administering to a subject a CCR10 polypeptide, a recombinant CCR10 polypeptide, an active CCR10 polypeptide fragment, or CCR10 activator as a preventative measure against a neurodegenerative disease or disorder. As more fully discussed elsewhere herein, methods of increasing the level or activity of a CCR10 encompass a wide plethora of techniques for increasing not only CCR10 activity, but also for increasing expression of a nucleic acid encoding CCR10. Additionally, as disclosed elsewhere herein, one skilled in the art would understand, once armed with the teaching provided herein, that the present invention encompasses a method of preventing a wide variety of diseases where increased expression and/or activity of CCR10 mediates, treats or prevents the disease. Further, the invention encompasses treatment or prevention of such diseases discovered in the future.

The invention encompasses administration of a CCR10 polypeptide, a recombinant CCR10 polypeptide, an active CCR10 polypeptide fragment, or a CCR10 activator to practice the methods of the invention; the skilled artisan would understand, based on the disclosure provided herein, how to formulate and administer the appropriate CCR10 polypeptide, recombinant CCR10 polypeptide, active CCR10 polypeptide fragment, or CCR10 activator to a subject. However, the present invention is not limited to any particular method of administration or treatment regimen. This is especially true where it would be appreciated by one skilled in the art, equipped with the disclosure provided herein, including the reduction to practice using an art-recognized model of an autoimmune disease, that methods of administering a CCR10 polypeptide, a recombinant CCR10 polypeptide, an active CCR10 polypeptide fragment, or CCR10 activator can be determined by one of skill in the pharmacological arts.

As used herein, the term "pharmaceutically-acceptable carrier" means a chemical composition with which an appropriate CCR10 polypeptide, recombinant CCR10 polypeptide, active CCR10 polypeptide fragment, or CCR10 activator, may be combined and which, following the combination, can be used to administer the appropriate CCR10 polypeptide, recombinant CCR10 polypeptide, active CCR10 polypeptide fragment, or CCR10 activator to a subject.

Modification of Nucleic Acid Molecules

Inhibition of CCR10 or any component of the signal transduction pathway associated with CCR10 or a functional equivalent thereof can be accomplished using a nucleic acid molecule. For example, the inhibitor is selected from the group consisting of a small interfering RNA (siRNA), a microRNA, an antisense nucleic acid, a ribozyme, an expression vector encoding a transdominant negative mutant, and the likes.

By way of example, modification of nucleic acid molecules is described in the context of an siRNA molecule. However, the methods of modifying nucleic acid molecules can be applied to other types of nucleic acid based modulators of the invention.

Polynucleotides of the siRNA may be prepared using any of a variety of techniques, which are useful for the preparation of specifically desired siRNA polynucleotides. For example, a polynucleotide may be amplified from a cDNA prepared from a suitable cell or tissue type. Such a polynucleotide may be amplified via polymerase chain reaction (PCR). Using this approach, sequence-specific primers are designed based on the sequences provided herein, and may be purchased or synthesized directly. An amplified portion of the primer may be used to isolate a full-length gene, or a desired portion thereof, from a suitable DNA library using well known techniques. A library (cDNA or genomic) is screened using one or more polynucleotide probes or primers suitable for amplification. Preferably, the library is size-selected to include larger polynucleotide sequences. Random primed libraries may also be preferred in order to identify 5' and other upstream regions of the genes. Genomic libraries are preferred for obtaining introns and extending 5' sequences. The siRNA polynucleotide contemplated by the present invention may also be selected from a library of siRNA polynucleotide sequences.

For hybridization techniques, a partial polynucleotide sequence may be labeled (e.g., by nick-translation or end-labeling with $^{32}P$) using well known techniques. A bacterial or bacteriophage library may then be screened by hybridization to filters containing denatured bacterial colonies (or lawns containing phage plaques) with the labeled probe (see, e.g., Sambrook et al., Molecular Cloning: A Laboratory Manual, Cold Spring Harbor Laboratories, Cold Spring Harbor, N.Y., 2001). Hybridizing colonies or plaques are selected and expanded, and the DNA is isolated for further analysis.

Alternatively, numerous amplification techniques are known in the art for obtaining a full-length coding sequence from a partial cDNA sequence. Within such techniques, amplification is generally performed via PCR. One such technique is known as "rapid amplification of cDNA ends" or RACE (see, e.g., Sambrook et al., Molecular Cloning: A Laboratory Manual, Cold Spring Harbor Laboratories, Cold Spring Harbor, N.Y., 2001).

A number of specific siRNA polynucleotide sequences useful for interfering with target polypeptide expression are presented in the Examples, the Drawings, and in the Sequence Listing included herein. siRNA polynucleotides may generally be prepared by any method known in the art, including, for example, solid phase chemical synthesis. Modifications in a polynucleotide sequence may also be introduced using standard mutagenesis techniques, such as oligonucleotide-directed site-specific mutagenesis. Further, siRNAs may be chemically modified or conjugated with other molecules to improve their stability and/or delivery properties. Included as one aspect of the invention are siRNAs as described herein, wherein one or more ribose sugars has been removed therefrom.

Alternatively, siRNA polynucleotide molecules may be generated by in vitro or in vivo transcription of suitable DNA sequences (e.g., polynucleotide sequences encoding a target polypeptide, or a desired portion thereof), provided that the DNA is incorporated into a vector with a suitable RNA polymerase promoter (such as for example, T7, U6, H1, or SP6 although other promoters may be equally useful). In addition, an siRNA polynucleotide may be administered to a mammal, as may be a DNA sequence (e.g., a recombinant nucleic acid construct as provided herein) that supports transcription (and optionally appropriate processing steps) such that a desired siRNA is generated in vivo.

In one embodiment, an siRNA polynucleotide, wherein the siRNA polynucleotide is capable of interfering with expression of a target polypeptide can be used to generate a silenced cell. Any siRNA polynucleotide that, when contacted with a biological source for a period of time, results in a significant decrease in the expression of the target polypeptide is included in the invention. Preferably the decrease is greater than about 10%, more preferably greater than about 20%, more preferably greater than about 30%, more preferably greater than about 40%, about 50%, about 60%, about 70%, about 75%, about 80%, about 85%, about 90%, about 95% or about 98% relative to the expression level of the target polypeptide detected in the absence of the siRNA. Preferably, the presence of the siRNA polynucleotide in a cell does not result in or cause any undesired toxic effects, for example, apoptosis or death of a cell in which apoptosis is not a desired effect of RNA interference.

In another embodiment, the siRNA polynucleotide that, when contacted with a biological source for a period of time, results in a significant decrease in the expression of the target polypeptide. Preferably the decrease is about 10%-20%, more preferably about 20%-30%, more preferably about 30%-40%, more preferably about 40%-50%, more preferably about 50%-60%, more preferably about 60%-70%, more preferably about 70%-80%, more preferably about 80%-90%, more preferably about 90%-95%, more preferably about 95%-98% relative to the expression level of the target polypeptide detected in the absence of the siRNA. Preferably, the presence of the siRNA polynucleotide in a cell does not result in or cause any undesired toxic effects.

In yet another embodiment, the siRNA polynucleotide that, when contacted with a biological source for a period of time, results in a significant decrease in the expression of the target polypeptide. Preferably the decrease is about 10% or more, more preferably about 20% or more, more preferably about 30% or more, more preferably about 40% or more, more preferably about 50% or more, more preferably about 60% or more, more preferably about 70% or more, more preferably about 80% or more, more preferably about 90% or more, more preferably about 95% or more, more preferably about 98% or more relative to the expression level of the target polypeptide detected in the absence of the siRNA. Preferably, the presence of the siRNA polynucleotide in a cell does not result in or cause any undesired toxic effects.

Any polynucleotide of the invention may be further modified to increase its stability in vivo. Possible modifications include, but are not limited to, the addition of flanking sequences at the 5' and/or 3' ends; the use of phosphorothioate or 2' O-methyl rather than phosphodiester linkages in the backbone; and/or the inclusion of nontraditional bases such as inosine, queosine, and wybutosine and the like, as well as acetyl-methyl-, thio- and other modified forms of adenine, cytidine, guanine, thymine, and uridine.

Genetic Modification

In other related aspects, the invention includes an isolated nucleic acid encoding a modulator of the invention, wherein the nucleic acid is operably linked to a promoter/regulatory sequence such that the nucleic acid is preferably capable of directing expression of the protein encoded by the nucleic acid. Thus, the invention encompasses expression vectors and methods for the introduction of exogenous DNA into cells with concomitant expression of the exogenous DNA in the cells such as those described, for example, in Sambrook et al. (2001, Molecular Cloning: A Laboratory Manual, Cold Spring Harbor Laboratory, New York), and in Ausubel et al. (1997, Current Protocols in Molecular Biology, John Wiley & Sons, New York).

The desired polynucleotide can be cloned into a number of types of vectors. However, the present invention should not be construed to be limited to any particular vector. Instead, the present invention should be construed to encompass a wide plethora of vectors which are readily available and/or well-known in the art. For example, a desired polynucleotide of the invention can be cloned into a vector including, but not limited to a plasmid, a phagemid, a phage derivative, an animal virus, and a cosmid. Vectors of particular interest include expression vectors, replication vectors, probe generation vectors, and sequencing vectors.

In specific embodiments, the expression vector is selected from the group consisting of a viral vector, a bacterial vector and a mammalian cell vector. Numerous expression vector systems exist that comprise at least a part or all of the compositions discussed above. Prokaryote- and/or eukaryote-vector based systems can be employed for use with the present invention to produce polynucleotides, or their cognate polypeptides. Many such systems are commercially and widely available.

Further, the expression vector may be provided to a cell in the form of a viral vector. Viral vector technology is well known in the art and is described, for example, in Sambrook et al. (2001), and in Ausubel et al. (1997), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. (See, e.g., WO 01/96584; WO 01/29058; and U.S. Pat. No. 6,326,193.

For expression of the desired polynucleotide, at least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 genes, a discrete element overlying the start site itself helps to fix the place of initiation.

Additional promoter elements, i.e., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either co-operatively or independently to activate transcription.

A promoter may be one naturally associated with a gene or polynucleotide sequence, as may be obtained by isolating the 5' non-coding sequences located upstream of the coding segment and/or exon. Such a promoter can be referred to as "endogenous." Similarly, an enhancer may be one naturally associated with a polynucleotide sequence, located either downstream or upstream of that sequence. Alternatively, certain advantages will be gained by positioning the coding polynucleotide segment under the control of a recombinant or heterologous promoter, which refers to a promoter that is not normally associated with a polynucleotide sequence in its natural environment. A recombinant or heterologous enhancer refers also to an enhancer not normally associated with a polynucleotide sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (U.S. Pat. No. 4,683,202, U.S. Pat. No. 5,928,906). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. Those of skill in the art of molecular biology generally know how to use promoters, enhancers, and cell type combinations for protein expression, for example, see Sambrook et al. (2001). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

A promoter sequence exemplified in the experimental examples presented herein is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, Moloney virus promoter, the avian leukemia virus promoter, Epstein-Barr virus immediate early promoter, Rous sarcoma virus promoter, as well as human gene promoters such as, but not limited to, the actin promoter, the myosin promoter, the hemoglobin promoter, and the muscle creatine promoter. Further, the invention should not be limited to the use of constitutive promoters. Inducible promoters are also contemplated as part of the invention. The use of an inducible promoter in the invention provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter. Further, the invention includes the use of a tissue specific promoter, which promoter is active only in a desired tissue. Tissue specific promoters are well known in the art and include, but are not limited to, the HER-2 promoter and the PSA associated promoter sequences.

In order to assess the expression of the modulator, the expression vector to be introduced into a cell can also contain either a selectable marker gene or a reporter gene or both to facilitate identification and selection of expressing cells from the population of cells sought to be transfected or infected through viral vectors. In other embodiments, the selectable marker may be carried on a separate piece of DNA and used in a co-transfection procedure. Both selectable markers and reporter genes may be flanked with appropriate regulatory sequences to enable expression in the host cells. Useful selectable markers are known in the art and include, for example, antibiotic-resistance genes, such as neo and the like.

Reporter genes are used for identifying potentially transfected cells and for evaluating the functionality of regulatory sequences. Reporter genes that encode for easily assayable proteins are well known in the art. In general, a reporter gene is a gene that is not present in or expressed by the recipient organism or tissue and that encodes a protein whose expression is manifested by some easily detectable property, e.g., enzymatic activity. Expression of the reporter gene is assayed at a suitable time after the DNA has been introduced into the recipient cells.

Suitable reporter genes may include genes encoding luciferase, beta-galactosidase, chloramphenicol acetyl transferase, secreted alkaline phosphatase, or the green fluorescent protein gene (see, e.g., Ui-Tei et al., 2000 FEBS Lett. 479:79-82). Suitable expression systems are well known and may be prepared using well known techniques or obtained commercially. Internal deletion constructs may be generated using unique internal restriction sites or by partial digestion of non-unique restriction sites. Constructs may then be transfected into cells that display high levels of modulator polynucleotide and/or polypeptide expression. In general, the construct with the minimal 5' flanking region showing the highest level of expression of reporter gene is identified as the promoter. Such promoter regions may be linked to a reporter gene and used to evaluate agents for the ability to modulate promoter-driven transcription.

In the context of an expression vector, the vector can be readily introduced into a host cell, e.g., mammalian, bacterial, yeast or insect cell by any method in the art. For example, the expression vector can be transferred into a host cell by physical, chemical or biological means. It is readily understood that the introduction of the expression vector comprising the polynucleotide of the invention yields a silenced cell with respect to a regulator.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York), and in Ausubel et al. (1997, Current Protocols in Molecular Biology, John Wiley & Sons, New York).

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

Regardless of the method used to introduce exogenous nucleic acids into a host cell or otherwise expose a cell to the inhibitor of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

Any DNA vector or delivery vehicle can be utilized to transfer the desired polynucleotide to a cell in vitro or in vivo. In the case where a non-viral delivery system is utilized, a preferred delivery vehicle is a liposome. The above-mentioned delivery systems and protocols therefore can be found in Gene Targeting Protocols, 2ed., pp 1-35 (2002) and Gene Transfer and Expression Protocols, Vol. 7, Murray ed., pp 81-89 (1991).

"Liposome" is a generic term encompassing a variety of single and multilamellar lipid vehicles formed by the generation of enclosed lipid bilayers or aggregates. Liposomes may be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). However, the present invention also encompasses compositions that have different structures in solution than the normal vesicular structure. For example, the lipids may assume a micellar structure or merely exist as nonuniform aggregates of lipid molecules. Also contemplated are lipofectamine-nucleic acid complexes.

Cell Populations

T helper cells (also known as effector T cells or Th cells) are a sub-group of lymphocytes (a type of white blood cell or leukocyte) that plays an important role in establishing and maximizing the capabilities of the immune system and in particular in activating and directing other immune cells. Different types of Th cells have been identified that originate in outcome of a differentiation process and are associated with a specific phenotype. Following T cell development, matured, naive (meaning they have never been exposed to the antigen to which they can respond) T cells leave the *thymus* and begin to spread throughout the body. Naive T cells can differentiate into a T-helper 1 (Th1), T-helper 2 (Th2), T-helper 17 (Th17) or regulatory T cell (Treg) phenotype.

Each of these Th cell types secretes cytokines, proteins or peptides that stimulate or interact with other leukocytes, including Th cells. However, each cell type has a peculiar phenotype and activity that interferes and often conflict with the other.

Th1, Th2, and Th17 (inflammatory T-helper or inflammatory Th), promote inflammation responses trough secretion of pro-inflammatory cytokines, such as IL-1, IL-6, TNF-α, IL-17, IL21, IL23, and/or through activation and/or inhibition of other T cell including other Th cells (for example Th1 cell suppresses Th2 and Th17, Th2 suppresses Th1 and Th17). Tregs instead, are a component of the immune system that suppresses biological activities of other cells associated to an immune response. In particular, Tregs can secrete immunosuppressive cytokines TGF-β and Interleukin 10, and are known to be able to limit or suppress inflammation.

The present invention is based on the discovery of the important role of CCR10 in a positive feedback circuit of immune homeostatic regulation in the skin where CCR10 maintains balanced presence and function of resident regulatory T (Treg) vs. effector T (Teff) cells, which in turn help to establish a homeostatic environment important for maintenance of the CCR10+ resident T cells.

Therapeutic Application

The present invention includes a modulator of CCR10 or any component of the signal transduction pathway associated with CCR10 or a functional equivalent thereof. The present invention includes a method of enhancing the immune response in a mammal comprising administering the mammal in need thereof with an inhibitor of CCR10 or any component of the signal transduction pathway associated with CCR10 or a functional equivalent thereof. In one embodiment, the present invention includes a method of inhibiting the immune response in a mammal comprising administering the mammal in need thereof with an activator of CCR10 or any component of the signal transduction pathway associated with CCR10 or a functional equivalent thereof.

In one embodiment, the invention provides compositions and methods for treating an autoimmune disease. In one embodiment, the autoimmune disease is psoriasis. In another embodiment, the autoimmune disease is autoimmune intestinal inflammation. Therefore the present invention includes a therapeutic benefit of inhibiting the immune response in a subject by activating one or more of CCR10, CCR10/ligand axis, and their functional equivalents.

In one embodiment, the mammal has a type of skin disease. In one embodiment, the skin disease is associated with an inappropriate level of immune response that is unable to alleviate the skin disease. Therefore, the invention can be used to increase the immune response in mammals that are in need of an enhancement of their immune response. Thus, treatment of the skin disease is accomplished by inducing an enhanced immune response using an inhibitor of CCR10 or any component of the signal transduction pathway associated with CCR10 or a functional equivalent thereof of the invention.

Accordingly, the invention provides compositions and methods for targeting one or more of CCR10, CCR10/ligand axis, and their functional equivalents for enhancing an immune response in a subject. That is, the invention is based on the novel discovery that CCR10 plays a role in regulating balanced maintenance and function of the skin-resident Treg and Teff cells to prevent overactive immune responses. Therefore, by inhibiting one or more of CCR10, CCR10/ligand axis, and their functional equivalents, an immune response can be enhanced in a subject to treat diseases and disorders that would be suppressed by the enhanced immune response, including but not limited to skin-specific infections by parasites (e.g., protozoan and metazoan pathogens such as *Leishmania* species, *Schistosoma* species, *Trypanosoma* species), bacteria (e.g., *Staphylococcus aureus*, MRSA-methicillin resistant staph *aureus, Streptococcus pyogenes, Pseudomonas* Aeruginosas, Corynebacteria, Mycobacteria), virus (e.g. Herpes simplex virus type 1, herpes simplex virus type 2, Human Herpes Viruses, varicella-zoster virus, human papillomavirus, Coxsackie virus A16, Hepatitis B virus, Epstein Barr virus), fungi (e.g., *Candida* species, *Trichophyton, epidermophyton, microsporum, Sporothrix schenckii, Blastomycosis dermatitidis*), and other microorganisms and associated symptoms such as *Cutaneous leishmaniasis* (Aleppo boil, Baghdad boil, Bay sore, Biskra button, Chiclero ulcer, Delhi boil, Kandahar sore, Lahore sore, *Leishmaniasis tropica*, Oriental sore, *Pian bois*, Uta), Dracunculiasis (*Dracontiasis*, Guinea worm disease, Medina worm), *Elephantiasis tropica* (*Elephantiasis arabum*), Elephant skin, Human trypanosomiasis, Gnathostomiasis, *Loa loa* filariasis, Mucocutaneous *leishmaniasis* (Espundia, *Leishmaniasis americana*), Post-kala-azar dermal *leishmaniasis* (Post-kala-azar dermatosis), Swimmer's itch (Cercarial dermatitis, Schistosome cercarial dermatitis), Impetigo, Ecthyma, Abscess, Furuncles, and Carbuncles, Staphyloccocal Scalded Skin Syndrome, Toxic Shock Syndrome, Cellulitis, Ecthyma, Erysipelas, Scarlet Fever, Necrotizing Fasciitis, Streptococcal Peri-anal Disease, Streptococcal Toxic Shock Syndrome, Leprosy, Skin Tuberculosis, Folliculitis, Cellulitis, Pyoderma, Rickettsial Disease, Spotted Fever, Lupus vulgaris, Scrofuloderma, Warty tuberculosis, Tuberculoid leprosy, Buruli ulcer, cold sores, genital herpes, Herpes zoster, *Molluscum contagiosum*, Warts, Hand, foot and mouth disease, papulovesicular acrodermatitis, Kaposi's sarcoma, *Candidiasis, Dermatophytoses, onychomycosis. Sporotrichosis, Blastomycosis*; and cancers such as Basal cell carcinoma, Squamous cell carcinoma, Kaposi's sarcoma, Merkel cell carcinoma Sebaceous gland carcinoma, Mycosis fungoides, *Cutaneous* lymphoma, Skin adnexal tumor, African Kaposi's sarcoma, Epidemic Kaposi's sarcoma.

As a non-limiting example, the mammal can have a skin disease associated with infection of a pathogenic organism. A pathogenic organism includes but is not limited to a virus, (e.g., single stranded RNA viruses, single stranded DNA viruses, double-stranded DNA viruses, HIV, hepatitis A, B, and C virus, HSV, CMV, EBV, HPV), a parasite (e.g., protozoan and metazoan pathogens such as Plasmodia species, *Leishmania* species, *Schistosoma* species, *Trypanosoma* species), bacteria (e.g., Mycobacteria, *Salmonella*, Streptococci, *E. coli*, Staphylococci), fungi (e.g., *Candida* species, *Aspergillus* species), *Pneumocystis carinii*, and the like.

Other types of infections include, but are not limited to, viral infections, bacterial infections, anthrax, parasitic infections, fungal infections and prion infection.

Viral infections include, but are not limited to, infections by hepatitis C, hepatitis B, influenza virus, herpes simplex virus (HSV), human immunodeficiency virus (HIV), respiratory syncytial virus (RSV), vesicular stomatitis virus (VSV), cytomegalovirus (CMV), poliovirus, encephalomyocarditis virus (EMCV), human papillomavirus (HPV) and smallpox virus. In one embodiment, the infection is an upper respiratory tract infection caused by viruses and/or bacteria, in particular, flu, more specifically, bird flu.

Bacterial infections include, but are not limited to, infections by streptococci, staphylococci, *E. Coli*, and *pseudomonas*. In one embodiment, the bacterial infection is an intracellular bacterial infection which is an infection by an intracellular bacterium such as mycobacteria (tuberculosis), *chlamydia, mycoplasma, listeria*, and a facultative intracelluar bacterium such as *staphylococcus aureus*.

Parasitic infections include, but are not limited to, worm infections, in particular, intestinal worm infection.

In one embodiment, the infection is a viral infection or an intracellular bacterial infection. In a more preferred embodiment, the infection is a viral infection by hepatitis C, hepatitis B, influenza virus, RSV, HPV, HSV1, HSV2, and CMV.

In one embodiment, the mammal has a type of cancer. In some instances, the cancer is a type of skin cancer where the level or type of immune response in the effect mammal is not adequate to alleviate the cancer. Therefore, the invention can be used to increase the immune response in mammals that are in need of an enhancement of their immune response. Thus, treatment of the cancer (e.g., skin cancer) is accomplished by inducing an enhanced immune response using an inhibitor of CCR10 or any component of the signal transduction pathway associated with CCR10 or a functional equivalent thereof of the invention.

In some instances, an inhibitor of CCR10 or any component of the signal transduction pathway associated with CCR10 or a functional equivalent thereof of the invention is administered in combination with an immunostimulatory protein to a patient in need thereof, resulting in an improved therapeutic outcome for the patient.

The disorder or disease can be treated by administration of an inhibitor of CCR10 or any component of the signal transduction pathway associated with CCR10 or a functional equivalent thereof of the invention optionally in combination with an antigen (e.g., vaccine) to a patient in need thereof. The present invention provides a means to increase an immune response in the patient in need thereof. In some instances, the enhancement of the immune response is specific to a desired antigen (e.g. vaccine) in the patient.

In another embodiment, the compounds of the present invention may be used in combination with existing therapeutic agents used to treat skin diseases or cancer. In some instances, the compounds of the invention may be used in combination these therapeutic agents to enhance the antitumor effect of the therapeutic agent.

In order to evaluate potential therapeutic efficacy of the compounds of the invention in combination with the antitumor therapeutics described elsewhere herein, these combinations may be tested for antitumor activity according to methods known in the art.

In one aspect, the present invention contemplates that the modulators of the invention may be used in combination with a therapeutic agent such as an anti-tumor agent including but not limited to a chemotherapeutic agent, an anti-cell proliferation agent or any combination thereof.

The invention should not be limited to any particular chemotherapeutic agent. Rather, any chemotherapeutic agent can be linked to the antibodies of the invention. For example, any conventional chemotherapeutic agents of the following non-limiting exemplary classes are included in the invention: alkylating agents; nitrosoureas; antimetabolites; antitumor antibiotics; plant alkyloids; taxanes; hormonal agents; and miscellaneous agents.

Alkylating agents are so named because of their ability to add alkyl groups to many electronegative groups under conditions present in cells, thereby interfering with DNA replication to prevent cancer cells from reproducing. Most alkylating agents are cell cycle non-specific. In specific aspects, they stop tumor growth by cross-linking guanine bases in DNA double-helix strands. Non-limiting examples include busulfan, carboplatin, chlorambucil, cisplatin, cyclophosphamide, dacarbazine, ifosfamide, mechlorethamine hydrochloride, melphalan, procarbazine, thiotepa, and uracil mustard.

Anti-metabolites prevent incorporation of bases into DNA during the synthesis (S) phase of the cell cycle, prohibiting normal development and division. Non-limiting examples of antimetabolites include drugs such as 5-fluorouracil, 6-mercaptopurine, capecitabine, cytosine arabinoside, floxuridine, fludarabine, gemcitabine, methotrexate, and thioguanine.

There are a variety of antitumor antibiotics that generally prevent cell division by interfering with enzymes needed for cell division or by altering the membranes that surround cells. Included in this class are the anthracyclines, such as doxorubicin, which act to prevent cell division by disrupting the structure of the DNA and terminate its function. These agents are cell cycle non-specific. Non-limiting examples of antitumor antibiotics include dactinomycin, daunorubicin, doxorubicin, idarubicin, mitomycin-C, and mitoxantrone.

Plant alkaloids inhibit or stop mitosis or inhibit enzymes that prevent cells from making proteins needed for cell growth. Frequently used plant alkaloids include vinblastine, vincristine, vindesine, and vinorelbine. However, the invention should not be construed as being limited solely to these plant alkaloids.

The taxanes affect cell structures called microtubules that are important in cellular functions. In normal cell growth, microtubules are formed when a cell starts dividing, but once the cell stops dividing, the microtubules are disassembled or destroyed. Taxanes prohibit the microtubules from breaking down such that the cancer cells become so clogged with microtubules that they cannot grow and divide. Non-limiting exemplary taxanes include paclitaxel and docetaxel.

Miscellaneous agents include chemotherapeutics such as bleomycin, hydroxyurea, L-asparaginase, and procarbazine that are also useful in the invention.

An anti-cell proliferation agent can further be defined as an apoptosis-inducing agent or a cytotoxic agent. The apoptosis-inducing agent may be a granzyme, a Bcl-2 family member, cytochrome C, a caspase, or a combination thereof. Exemplary granzymes include granzyme A, granzyme B, granzyme C, granzyme D, granzyme E, granzyme F, granzyme G, granzyme H, granzyme I, granzyme J, granzyme K, granzyme L, granzyme M, granzyme N, or a combination thereof. In other specific aspects, the Bcl-2 family member is, for example, Bax, Bak, Bcl-Xs, Bad, Bid, Bik, Hrk, Bok, or a combination thereof.

In additional aspects, the caspase is caspase-1, caspase-2, caspase-3, caspase-4, caspase-5, caspase-6, caspase-7, caspase-8, caspase-9, caspase-10, caspase-11, caspase-12, caspase-13, caspase-14, or a combination thereof. In specific aspects, the cytotoxic agent is TNF-α, gelonin, Prodigiosin, a ribosome-inhibiting protein (RIP), *Pseudomonas* exotoxin, *Clostridium difficile* Toxin B, *Helicobacter pylori* VacA, *Yersinia enterocolitica* YopT, Violacein, diethylenetriaminepentaacetic acid, irofulven, Diptheria Toxin, mitogillin, ricin, botulinum toxin, cholera toxin, saporin 6, or a combination thereof.

In some embodiments, an effective amount of a compound of the invention and a therapeutic agent is a synergistic amount. As used herein, a "synergistic combination" or a "synergistic amount" of a compound of the invention and a therapeutic agent is a combination or amount that is more effective in the therapeutic or prophylactic treatment of a disease than the incremental improvement in treatment outcome that could be predicted or expected from a merely additive combination of (i) the therapeutic or prophylactic benefit of the compound of the invention when administered at that same dosage as a monotherapy and (ii) the therapeutic or prophylactic benefit of the therapeutic agent when administered at the same dosage as a monotherapy.

Dosage and Formulation (Pharmaceutical Compositions)

Administration of the therapeutic composition in accordance with the present invention may be continuous or intermittent, depending, for example, upon the recipient's physiological condition, whether the purpose of the administration is therapeutic or prophylactic, and other factors known to skilled practitioners. The administration of the compositions of the invention may be essentially continuous over a preselected period of time or may be in a series of spaced doses. Both local and systemic administration is contemplated. The amount administered will vary depending on various factors including, but not limited to, the composition chosen, the particular disease, the weight, the physical condition, and the age of the mammal, and whether prevention or treatment is to be achieved. Such factors can be readily determined by the clinician employing animal models or other test systems which are well known to the art One or more suitable unit dosage forms having the therapeutic agent(s) of the invention, which, as discussed below, may optionally be formulated for sustained release (for example using microencapsulation, see WO 94/07529, and U.S. Pat. No. 4,962,091 the disclosures of which are incorporated by reference herein), can be administered by a variety of routes including parenteral, including by intravenous and intramuscular routes, as well as by direct injection into the diseased tissue. For example, the therapeutic agent may be directly injected into the tumor. The formulations may, where appropriate, be conveniently presented in discrete unit dosage forms and may be prepared by any of the methods well known to pharmacy. Such methods may include the step of bringing into association the therapeutic agent with liquid carriers, solid matrices, semi-solid carriers, finely divided solid carriers or combinations thereof, and then, if necessary, introducing or shaping the product into the desired delivery system.

When the therapeutic agents of the invention are prepared for administration, they are preferably combined with a pharmaceutically acceptable carrier, diluent or excipient to form a pharmaceutical formulation, or unit dosage form. The total active ingredients in such formulations include from 0.1 to 99.9% by weight of the formulation. A "pharmaceutically acceptable" is a carrier, diluent, excipient, and/or salt that is compatible with the other ingredients of the formulation, and not deleterious to the recipient thereof. The active ingredient for administration may be present as a powder or as granules; as a solution, a suspension or an emulsion.

Pharmaceutical formulations containing the therapeutic agents of the invention can be prepared by procedures known in the art using well known and readily available ingredients. The therapeutic agents of the invention can also be formulated as solutions appropriate for parenteral administration, for instance by intramuscular, subcutaneous or intravenous routes.

The pharmaceutical formulations of the therapeutic agents of the invention can also take the form of an aqueous or anhydrous solution or dispersion, or alternatively the form of an emulsion or suspension.

Thus, the therapeutic agent may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

It will be appreciated that the unit content of active ingredient or ingredients contained in an individual aerosol dose of each dosage form need not in itself constitute an effective amount for treating the particular indication or disease since the necessary effective amount can be reached by administration of a plurality of dosage units. Moreover, the effective amount may be achieved using less than the dose in the dosage form, either individually, or in a series of administrations.

The pharmaceutical formulations of the present invention may include, as optional ingredients, pharmaceutically acceptable carriers, diluents, solubilizing or emulsifying agents, and salts of the type that are well-known in the art. Specific non-limiting examples of the carriers and/or diluents that are useful in the pharmaceutical formulations of the present invention include water and physiologically acceptable buffered saline solutions, such as phosphate buffered saline solutions pH 7.0-8.0.

The expression vectors, transduced cells, polynucleotides and polypeptides (active ingredients) of this invention can be formulated and administered to treat a variety of disease states by any means that produces contact of the active ingredient with the agent's site of action in the body of the organism. They can be administered by any conventional means available for use in conjunction with pharmaceuticals, either as individual therapeutic active ingredients or in a combination of therapeutic active ingredients. They can be administered alone, but are generally administered with a pharmaceutical carrier selected on the basis of the chosen route of administration and standard pharmaceutical practice.

In general, water, suitable oil, saline, aqueous dextrose (glucose), and related sugar solutions and glycols such as propylene glycol or polyethylene glycols are suitable carriers for parenteral solutions. Solutions for parenteral administration contain the active ingredient, suitable stabilizing agents and, if necessary, buffer substances. Antioxidizing agents such as sodium bisulfate, sodium sulfite or ascorbic acid, either alone or combined, are suitable stabilizing agents. Also used are citric acid and its salts and sodium Ethylenediaminetetraacetic acid (EDTA). In addition, parenteral solutions can contain preservatives such as benzalkonium chloride, methyl- or propyl-paraben and chlorobutanol. Suitable pharmaceutical carriers are described in Remington's Pharmaceutical Sciences, a standard reference text in this field.

The active ingredients of the invention may be formulated to be suspended in a pharmaceutically acceptable composition suitable for use in mammals and in particular, in humans. Such formulations include the use of adjuvants such as muramyl dipeptide derivatives (MDP) or analogs that are described in U.S. Pat. Nos. 4,082,735; 4,082,736; 4,101,536; 4,185,089; 4,235,771; and 4,406,890. Other adjuvants, which are useful, include alum (Pierce Chemical Co.), lipid A, trehalose dimycolate and dimethyldioctadecylammonium bromide (DDA), Freund's adjuvant, and IL-12. Other components may include a polyoxypropylene-polyoxyethylene block polymer (Pluronic®), a non-ionic surfactant, and a metabolizable oil such as squalene (U.S. Pat. No. 4,606,918).

Additionally, standard pharmaceutical methods can be employed to control the duration of action. These are well known in the art and include control release preparations and can include appropriate macromolecules, for example polymers, polyesters, polyamino acids, polyvinyl, pyrolidone, ethylenevinylacetate, methyl cellulose, carboxymethyl cellulose or protamine sulfate. The concentration of macromolecules as well as the methods of incorporation can be adjusted in order to control release. Additionally, the agent can be incorporated into particles of polymeric materials such as polyesters, polyamino acids, hydrogels, poly(lactic acid) or ethylenevinylacetate copolymers. In addition to being incorporated, these agents can also be used to trap the compound in microcapsules.

Accordingly, the pharmaceutical composition of the present invention may be delivered via various routes and to various sites in a mammal body to achieve a particular effect (see, e.g., Rosenfeld et al., 1991; Rosenfeld et al., 1991a). One skilled in the art will recognize that although more than one route can be used for administration, a particular route can provide a more immediate and more effective reaction than another route. Local or systemic delivery can be accomplished by administration comprising application or instillation of the formulation into body cavities, inhalation or insufflation of an aerosol, or by parenteral introduction, comprising intramuscular, intravenous, peritoneal, subcutaneous, intradermal, as well as topical administration.

The active ingredients of the present invention can be provided in unit dosage form wherein each dosage unit, e.g., a teaspoonful, tablet, solution, or suppository, contains a predetermined amount of the composition, alone or in appropriate combination with other active agents. The term "unit dosage form" as used herein refers to physically discrete units suitable as unitary dosages for human and mammal subjects, each unit containing a predetermined quantity of the compositions of the present invention, alone or in combination with other active agents, calculated in an amount sufficient to produce the desired effect, in association with a pharmaceutically acceptable diluent, carrier, or vehicle, where appropriate. The specifications for the unit dosage forms of the present invention depend on the particular effect to be achieved and the particular pharmacodynamics associated with the pharmaceutical composition in the particular host.

These methods described herein are by no means all-inclusive, and further methods to suit the specific application will be apparent to the ordinary skilled artisan. Moreover, the effective amount of the compositions can be further approximated through analogy to compounds known to exert the desired effect.

The invention is now described with reference to the following Examples. These Examples are provided for the purpose of illustration only and the invention should in no way be construed as being limited to these Examples, but rather should be construed to encompass any and all variations which become evident as a result of the teaching provided herein.

EXAMPLES

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

Example 1: CCR10 Regulates Balanced Maintenance and Function of Resident Regulatory and Effector T Cells to Promote Immune Homeostasis in the Skin The results presented herein demonstrate that that CCR10 is a critical regulator of immune homeostasis in the skin. The results show that in CCR10-knockout/EGFP-knockin (CCR10$^{-/-}$) mice (Jin et al., 2010, J Immunol 185:5723-31; Hu et al., 2011, Proc Natl Acad Sci USA 108:E1035-44), imbalanced presence and dysregulated functions of memory-like resident regulatory and effector T cells (Treg and Teff) result in enhanced/prolonged innate and memory immune responses to the skin stimulation. CCR10 expression on the memory-like resident T cells is preferentially imprinted early on their progenitors during skin inflammation for their maintenance in homeostatic skin after resolution of inflammation but not on skin-infiltrating effector T cells for their migration during inflammation. Chronic inflammation due to absence of Foxp3$^+$ regulatory T cells prevents establishment of CCR10$^+$ resident effector T cells in the skin. In addition, the enhanced immune response due to CCR10-knockout helps better clearance of infection of *Leishmamia* parasites in the skin, suggesting clinical potentials of targeting the CCR10/ligand axis.

The materials and methods employed in the experiments disclosed herein are now described.

Material and Methods

Mouse Models and Human Bio-Samples

CCR10-knockout/EGFP-knockin (CCR10$^{-/-}$) mice were generated in the laboratory (Jin, Y., et al., 2010, *J Immunol* 185:5723-5731). Rag1$^{-/-}$, Scurfy and wild type (WT) CD45.1$^+$ congenic C57BL6 mice were from The Jackson Laboratory (Bar Harbor, Me.). CD45.1$^+$CD45.2$^+$ wild type C57BL6, CD45.1$^+$CD45.2$^+$ or CD45.1$^+$CD45.2$^-$ CCR10$^{+/-}$, CD45.1$^+$CD45.2$^+$ Rag1$^{-/-}$ mice were generated by proper crossing. Scurfy mice were also crossed to CCR10-knockout/EGFP-knockin mice to introduce a CCR10-knockout/EGFP-knockin allele for the EGFP reporter of CCR10 expression. All animal experiments were approved by The Pennsylvania State University Institutional Animal Care and Use Committee. The human healthy skin was from people undergoing the plastic surgery. Use of the bio-samples of humans was approved by the institutional review board of Anhui Medical University.

Chemical Reagents and Induction of Skin Inflammation

1-Fluoro-2,4-dinitrobenzene (DNFB), Phorbol 12-myristate 13-acetate (TPA) and Fluorescein 5(6)-isothiocyanate (Fitc) and chicken ovalbumin (OVA) were purchased from Sigma-Aldrich (St. Louis, Mo.). Cholera toxin was purchased from List Biological (Campbell, Calif.).

To induce classic contact hypersensitive (CHS) responses, mouse abdomen was shaved and sensitized with 100 µl 0.5% DNFB in 4:1 acetone/olive oil at day 0 and 1. At day 5, the baseline ear thicknesses of both right and left ears were measured by a micrometer gauge. Immediately following the ear measurement, each side of the ear was topically applied with 10 µl of 0.2% DNFB solution or control solvents (20 µl total). Ear thickness was measured at various days after the chemical challenge on the ear. The change in the ear thickness (ΔT) was calculated by subtracting the ear thickness before the chemical treatment from the ear thickness after the chemical application.

The memory CHS response was induced similarly as the classic CHS response except that ears were challenged with DNFB one month after the DNFB sensitization.

For DNFB, FITC or TPA-induced innate skin inflammation, each side of a ear was applied with 10 µl of the chemicals (0.5% DNFB in 4:1 acetone/olive oil, 0.5% FITC in 1:1 acetone/dibutylpthalate, or 100 µg/ml TPA in acetone) once. The ear thickness was measured at various days after the application.

The OVA-induced skin inflammation was performed as reported (Campbell, J. J., et al., 2007, *J Immunol* 178:3358-

3362), except that total OVA proteins instead of peptides were epicutaneously applied to the mouse skin.

Skin Cell Isolation

Skin cells were prepared similarly as previous described (Jin, Y., et al., 2010, *J Immunol* 185:5723-5731). Briefly, mouse hair was removed from the skin by hair clipper and Nair (Church & Dwight, Princeton, N.J.). Mouse skin was excised, trimmed of subcutaneous fat and minced, following by 2-hour digestion with 4 mg/ml Collagenase Type I (Worthington, Lakewood, N.J.), 2 mg/ml Collagenase Type IV (Worthington, Lakewood, N.J.), 2 mg/ml hyaluronidase type I-s (Sigma-Aldrich, St. Louis, Mo.) and 4% BSA (Sigma-Aldrich, St. Louis, Mo.) in DMEM. Thirty minutes before the end of digestion, 0.0001% DNase (Sigma-Aldrich, St. Louis, Mo.) was added into the digest buffer. Mononucleocytes were enriched from the cell preparations using Percoll gradients (40%/80%). The similarly isolated human skin cells were let recovered in the culture medium overnight before flow cytometric analysis.

Bone Marrow Cell Reconstitution

Cell sorter-purified EGFP$^-$ BM cells of CCR10$^{+/-}$ (CD45.1$^+$CD45.2$^-$) and CCD10$^{-/-}$ (CD45.1$^-$ CD45.2$^+$) mice were 1:1 mixed and injected intravenously into lethally irradiated (950 Rad) WT C57BL6 or CCR10$^{+/-}$ (CD45.1$^+$ D45.2$^+$) mice (total 10$^6$ cells per mouse). The recipients were analyzed 7 to 8 wk after the transfer.

Skin *Leishmania major* Infection

*L. major* NIH Friedlin V1 strain (MHOM/IL/80/FN) was grown in M199 medium supplemented with 25 mM HEPES and 20% FCS until a stationary phase. Mice were injected subcutaneously with 1×10$^6$ stationary-phase promastigotes in the ear dermis. Infected ears were collected at various time points and total genomic DNA was extracted with DNeasy Tissue Kit (Qiagen, Valencia, Calif.). Tissue *Leishmania* genomic DNA levels were quantified by qPCR with primers (JW11: CCTATTTTACACCAAC CCCCAGT (SEQ ID NO: 1); JW12: GGGTAGGGGCGTTCTGC GAAA (SEQ ID NO: 2)) specific to *L. major* 16S rDNA and normalized on levels of mouse genomic β-actin as previously described (Nicolas, L., et al., 2000, *Infect Immun* 68:6561-6566).

In Vivo T Cell Transfer

EGFP$^-$ CD3$^+$ T cells were sorter-purified from splenocytes of CCR10$^{+/-}$ or CCR10$^{-/-}$ mice. 4×10$^5$ splenic EGFP$^-$ CD3$^+$ T cells of CCR10$^{+/-}$ or CCR10$^{-/-}$ mice were intraperitoneally injected into Rag1$^{-/-}$ mice separately, which were then tested for the DNFB-induced classic or memory CHS responses after the cell transfer. For adoptive transfer of OVA-specific T cells, about 0.5×10$^6$ purified splenic transgenic T cells of CCR10$^{+/-}$ or CCR10$^{-/-}$ OTI or OT-II mice were intraperitoneally injected into WT mice with different CD45 polymorphism (indicated in the relevant figure), which were then epicutaneously challenged with Ova proteins (Campbell, J. J., et al., 2007, *J Immunol* 178:3358-3362).

Naïve T Cell Transfer-Induced Skin Inflammation

EGFP$^-$ naive T cells (CD3$^+$CD4$^+$CD25–CD45RB$^{high}$, CD45.1$^+$) and Treg cells (CD3$^+$CD4$^+$CD25$^+$CD45RB$^-$, CD45.2$^+$) were sorted from splenocytes of CCR10$^{+/-}$ mice. 4×10$^5$ naive T cells alone, or 2×10$^5$ naive along with 2×10$^5$ Treg cells, were intravenously injected into Rag1$^{-/-}$ mice (CD45.1$^+$CD45.2$^+$). The recipients were analyzed 7 to 8 wk after the transfer.

Real-Time RT-PCR Analysis of Cytokine Transcripts

Total RNA of mouse ears were isolated and reverse-transcribed to cDNA, which were then subject to the Sybr green real-time PCR with following primers. TNF-α Forward: TTCTATGGCCCAGACCC (SEQ ID NO: 3), Reverse: GGCACCACTAGTTGGTTGTC (SEQ ID NO:4); IL-1β: Forward: TCTCGCAGCAGCACATCA (SEQ ID NO: 5), Reverse: CACACCAGCAGGTTATCATCAT (SEQ ID NO: 6); IL-10 Forward: ACCAAAGCCACAAAGCAGCC (SEQ ID NO: 7), Reverse: CCGACTGGGAAGTGGGTGC (SEQ ID NO: 8); β-actin Forward: CCCATCTACGAGGGCTAT (SEQ ID NO: 9), Reverse: TGTCACGCACGATTTCC (SEQ ID NO: 10). Relative levels of transcripts were calculated with the delta delta CT method.

Antibodies and Flow Cytometry

The antibodies used for the flow cytometry and staining and analyzing strategies were detailed in the supplementary methods. Cells stained with proper combination of antibodies were analyzed on a flow cytometer with appropriate cell gating (indicated in the figures).

PE- or PeCy7-anti-mouse CD62L (MEL-14, 1:200 dilution), PE-, PeCy5- or PeCy7-anti-mouse CD44 (IM7, 1:400), PE-, Biotin- or PeCy7-anti-mouse CD4 (GK1.5, 1:200), PE-, PeCy5- or Biotin-anti-mouse CD8α (53-6.7, 1:100), PE- or Biotin-anti-mouse TCRγδ (GL3, 1:100), Alexa Fluor 647-anti-mouse/rat Foxp3 (FJK-16s, 1:50) and PE-anti-mouse TCRβ (H57-597, 1:100) were purchased from eBioscience (San Diego, Calif.). Alexa Fluor 647-anti-mouse IL-17A (TC11-18H10.1, 1:250), PeCy7- or Pacific Blue anti-mouse CD45.1 (A20, 1:200), Alexa Fluor 647- or Alexa Fluor 700-anti-mouse CD45.2 (104, 1:100), Alexa Fluor 647-anti-mouse CD127 (A7R34, 1:100), PE- or PeCy7- or Biotin-anti-mouse CD3ε (145-2C11, 1:100), PE-CD25 (PC61, 1:100) and PE-KLRG1 (2F1/KLRG1, 1:100) were from Biolegend (San Diego, Calif.). APC-anti-mouse IL-10 (JES5-16E3, 1:100), FITC-anti-human CD3 (UCHT1, 1:50), PeCy7-anti-human CD4 (SK3, 1:50) and Streptavidin-PE-Texas Red (1:200) were from BD Biosciences (San Jose, Calif.). PE-anti-human CCR10 (314305, 1:10) was from R&D Systems (Minneapolis, Minn.). PE-Alexa Fluor 610-anti-mouse CD4 (RM4-5, 1:100) and PE-Alexa Fluor 610-anti-mouse CD8α (5H10, 1:100) were from Invitrogen (Camarillo, Calif.). Foxp3/Transcription Factor Staining Buffer Set was from eBioscience (San Diego, Calif.). Cells stained with proper combination of antibodies and analyzed on flow cytometer FC500 (Beckman Coulter) or BD Fortessa LSRII (San Jose, Calif.). Cells stained with a single individual antibody were used to calibrate the signal output and compensation. Staining with the isotype control antibodies was included to confirm the specific signal for their corresponding antigen-specific antibody staining Flow data were analyzed with Flowjo (Ashland, Oreg.).

In Vitro T Cell Stimulation

Skin EGFP$^+$CD4$^+$CD25$^-$ T cells purified from CCR$^{+/-}$ and CCR10$^{-/-}$ mice were cultured in the presence of IL-2 and coated anti-CD28/anti-TCRβ antibodies for 2 days. The culture media were collected and analyzed by the mouse IL-17A ELISA Ready-SET-Go!® Set (eBioscience, San Diego, Calif.).

Statistical Analyses

Data are expressed as means±standard errors (SEM) and analyzed by two-tailed student T test or Fisher test to determine statistical significance for two-group comparison. The ANOVA test with Tukey adjustment was used for multiple group comparison. $P<0.05$ is considered significant.

The results of the experiments presented in this Example are now described.

Figure 8:
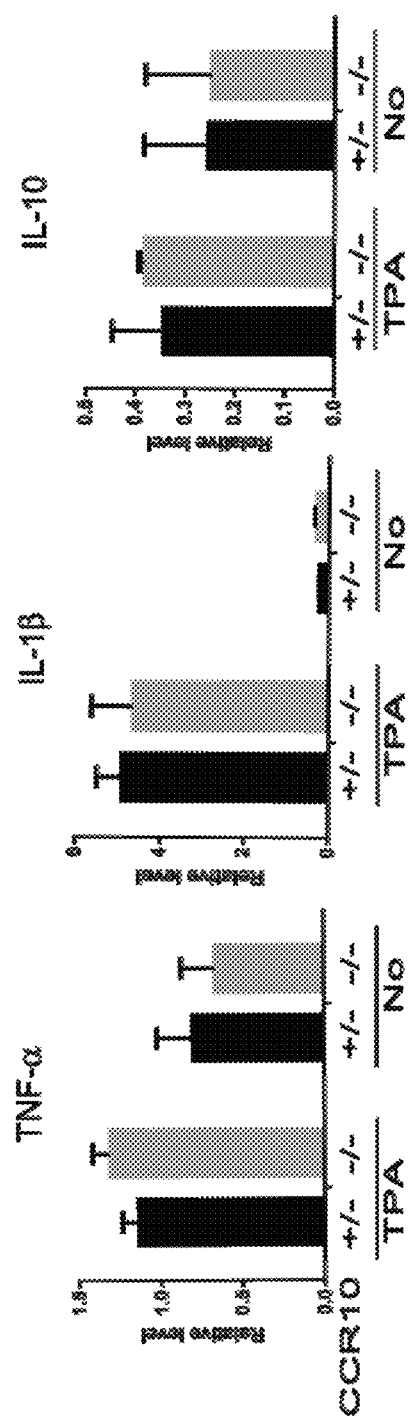
FIG. 8 is an image showing quantitative real-time RT-PCR analysis of RNA isolated from treated ears 3 days after the one-time TPA application for TNF-α, IL-1β and IL-10. "No" indicates untreated skin samples. The values are relative levels normalized on β-actin. N=4 CCR10$^{+/-}$ and 5 CCR10$^{-/-}$ mice.

Over-Reactive Innate Immune Response to Allergen Stimulation in Skin of CCR10$^{-/-}$ Mice To assess roles of CCR10 in the skin inflammation, experiments were performed to test CCR10-/- mice in several models. In a DNFB-induced CHS assay, CCR10$^{-/-}$ and CCR10$^{+/-}$ mice had similar ear thickness increases (FIG. 1A), indicating that CCR10 is not critical for the T-cell mediated CHS response and consistent with the report that CCR10-knockout does not affect the T cell migration (Tubo, N. J., et al., 2011, *Am J Pathol* 178:2496-2503). Surprisingly, CCR10$^{-/-}$ mice had significantly larger ear thickness increases than CCR10$^{+/-}$ mice early after the one-time DNFB application (FIG. 1B), suggesting an enhanced innate response. Supporting this, the treated ears of CCR10$^{-/-}$ mice exhibited much higher levels of gene expression of TNF-α and lower IL-10 than CCR10$^{+/-}$ controls (FIG. 1C). CCR10$^{-/-}$ mice also had an enhanced innate response to one-time treatment of another irritant/allergen FITC (FIG. 1D-1E). On the other hand, CCR10$^{-/-}$ and CCR10$^{+/-}$ mice had similar responses to topical application of TPA, a strong mitogen that activates both keratinocytes and immune cells (FIG. 1F and FIG. 8). Considering the one-time DNFB or FITC treatments are weaker stimulators than TPA or repeated DNFB treatments of the CHS assay, these results reveal that CCR10$^{-/-}$ mice have a reduced activation threshold to the weak stimulation but still mount full-scale responses once the threshold is overcome by strong stimulators, suggesting a defect in immune regulatory system in the skin.

Figures 2A, 2B, 2C, 2D, 2E, 2F:
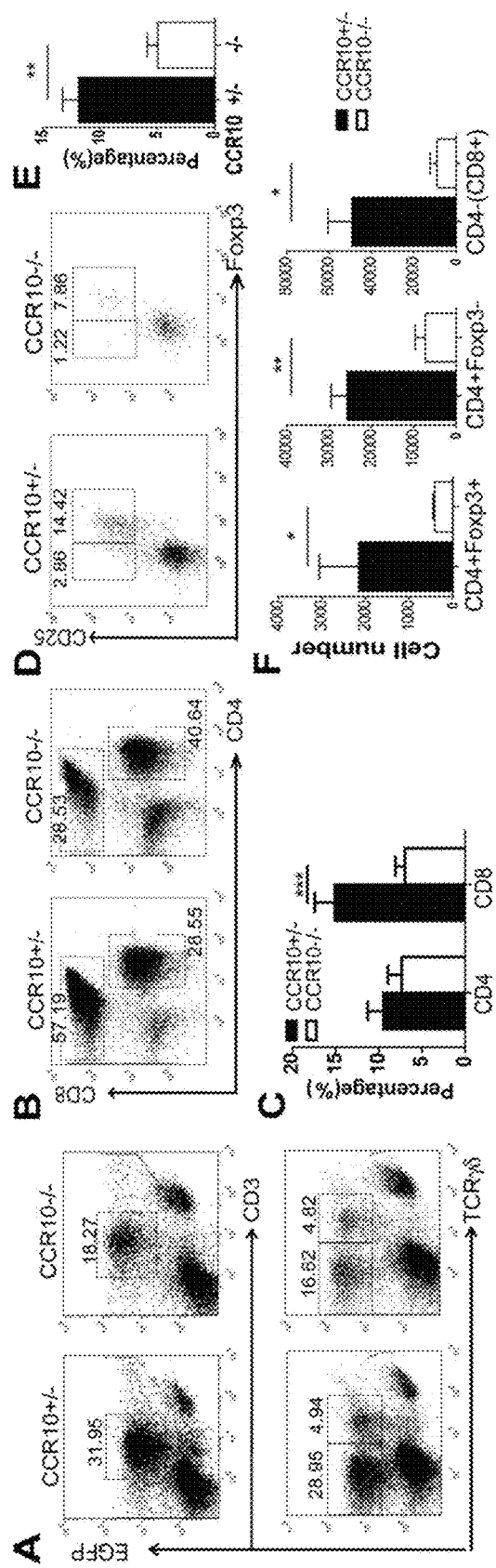
FIGS. 2A through 2K, is a series of images demonstrating imbalanced maintenance and dysregulated functions of Treg and Teff cells in the skin of CCR10$^{-/-}$ mice.
Figure 9:
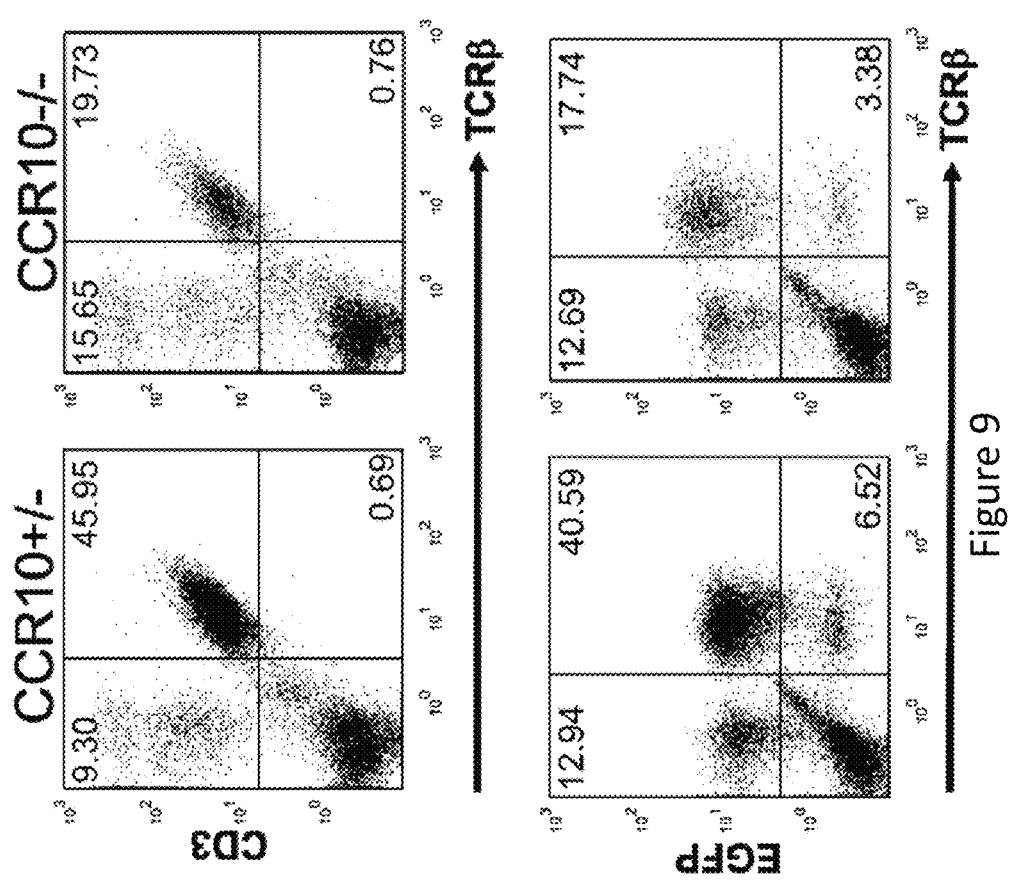
FIG. 9 is an image of a representative flow cytometric analysis of gated lymphocytes isolated from the skin of CCR10$^{+/-}$ and CCR10$^{-/-}$ mice for CD3$^+$TCRβ$^+$ T cells and their expression of EGFP (CCR10).
Figure 10:
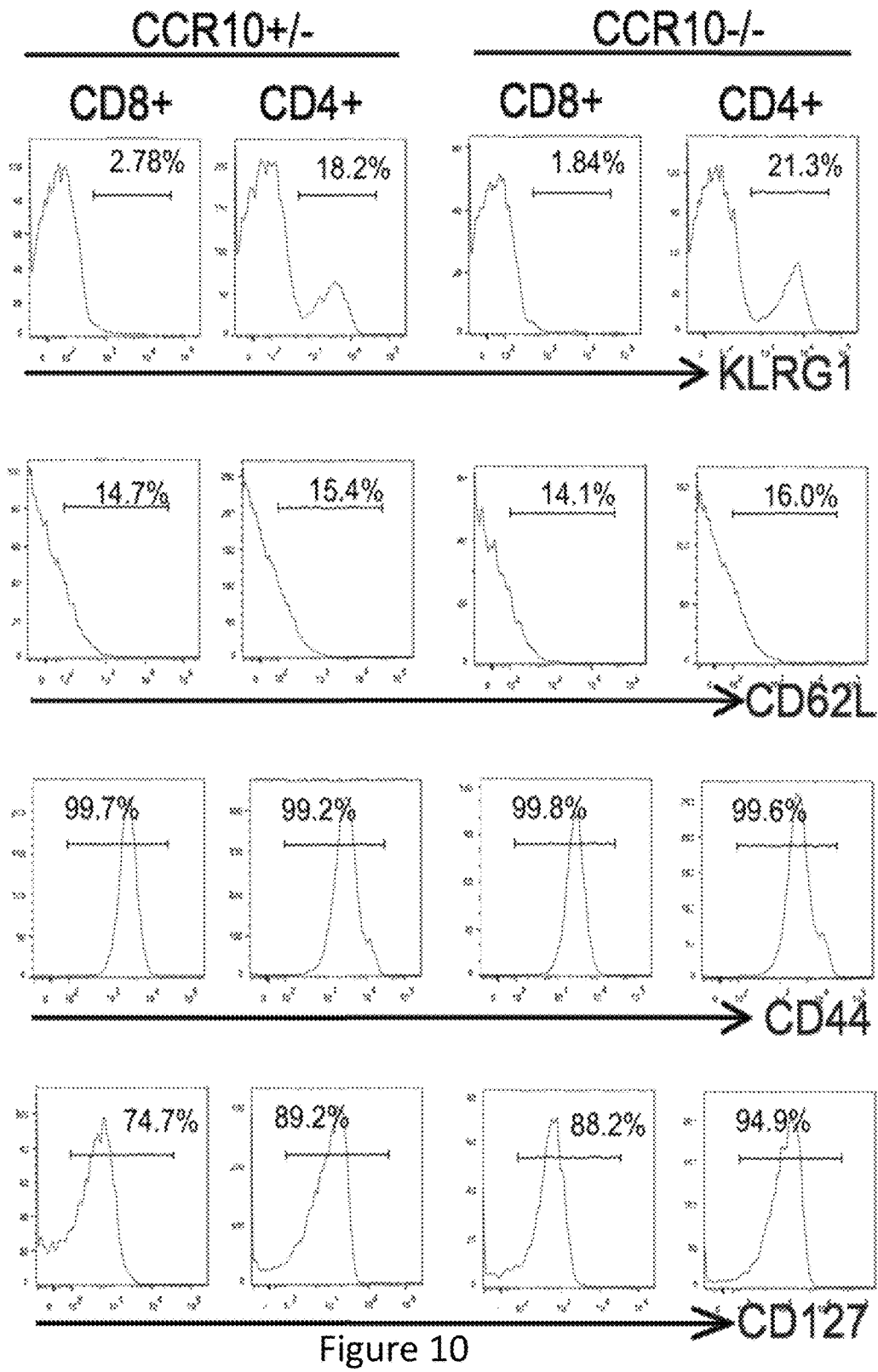
FIG. 10 is an image of a representative flow cytometric analysis of gated EGFP$^+$ CD4$^+$ and CD8$^+$ T cells isolated from the skin of CCR10$^{+/-}$ and CCR10$^{-/-}$ mice for molecular markers associated with the T cell memory.

Imbalanced Maintenance of Skin-Resident Treg and Teff Cells in CCR10$^{-/-}$ Mice The next experiment was performed to analyze how CCR10-knockout affected the skin-resident T cells, including Treg cells that are critical in the immune regulation. Based on the EGFP reporter for CCR10 in CCR10$^{+/-}$ mice (Jin, Y., et al., 2010, *J Immunol* 185:5723-5731 and Hu, S., et al., 2011, *Proc Natl Acad Sci USA* 108:E1035-1044), the majority of skin-resident αβT cells highly expressed CCR10 (EGFP) (FIG. 2A and FIG. 9) and memory T cell markers (KLRG1$^-$CD62L$^-$ CD44$^{high}$CD127$^+$ for CD8$^+$ and KLRG1$^\pm$CD62L$^-$CD44$^{high}$CD127$^+$ for CD4$^+$ cells) (FIG. 10) (Jin, Y., et al., 2010, *J Immunol* 185:5723-5731 and Kalia, V., et al., 2010, *Immunity* 32:91-103). Compared to CCR10$^{+/-}$ mice, CCR10$^{-/-}$ mice had fewer skin αβT (CD3$^+$ γδTCR$^-$) cells (FIG. 2A), of which CD8$^+$ subset was impaired more profoundly than CD4$^+$ subset (FIG. 2B-2C). The CCR10$^{low}$ CD3$^{high}$ population of T cells were Vγ3$^+$ γδT cells that were increased in the dermis of CCR10$^{-/-}$ mice due to dysregulated localization (FIG. 2A), as previously reported (Jin, Y., et al., 2010, *J Immunol* 185:5723-5731). Notably, CCR10$^{-/-}$ mice had significantly fewer Foxp3$^+$ Treg cells within the skin CD4$^+$ population than CCR10$^{+/-}$ mice (FIG. 2D-2E). When total cell yields are considered, numbers of Treg, CD4$^+$ and CD8$^+$(CD4$^-$) Teff cells isolated from skin of CCR10$^{-/-}$ mice were all less than those of corresponding CCR10$^{+/-}$ cells (FIG. 2F). In contrast to the skin, very few EGFP$^+$ T cells were found in internal lymphoid organs such as spleens and their numbers were even higher in CCR10$^{-/-}$ than in CCR10$^{+/-}$ mice (FIG. 11), suggesting that defective maintenance of T cells in the skin results in their abnormal accumulation in the internal sites.

Impaired Immune Homeostasis in the Skin of CCR10$^{-/-}$ Mice

Figures 2G, 2H, 2I, 2J, 2K:
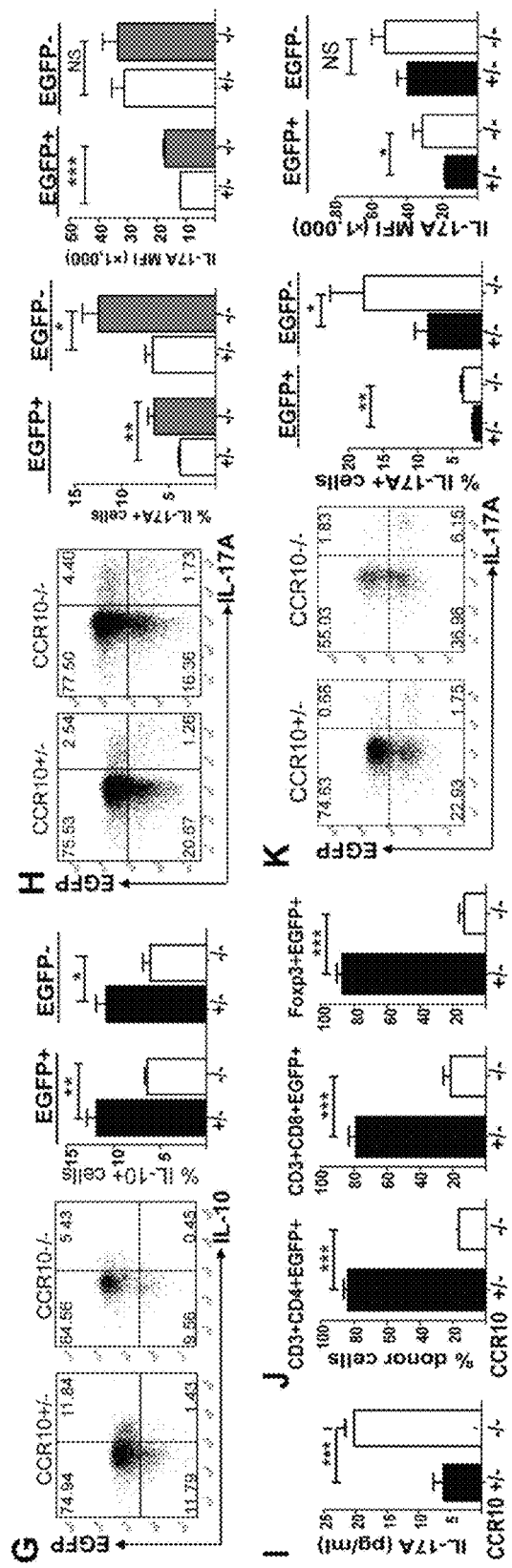

The imbalanced presence of resident Treg vs. Teff cells could impair skin immune homeostasis in CCR10$^{-/-}$ mice. Indeed, skin CD4$^+$ T cells of CCR10$^{-/-}$ mice contained significantly lower percentages of IL-10$^+$ and higher IL-17A$^+$ (Th17) cells than CCR10$^{+/-}$ controls (FIG. 2G-2H). EGFP$^+$ Th17 cells of CCR10$^{-/-}$ mice also had markedly higher mean fluorescent intensity (MFI) for the IL-17A staining than EGFP$^+$ Th17 cells of CCR10$^{+/-}$ mice (FIG. 2H), suggesting that CCR10 regulates function of the resident CCR10$^+$ Th17 cells besides their maintenance. Supporting this conclusion, purified EGFP$^+$ skin CD4$^+$ Teff cells of CCR10$^{-/-}$ mice secreted much higher levels of IL-17A than the CCR10$^{+/-}$ controls in culture (FIG. 2I). Notably, EGFP (CCR10)$^-$ skin T cells of CCR10$^{+/-}$ mice contained higher percentage of Th17 cells with higher IL-17A production than EGFP (CCR10)$^+$ skin T cells of the same mice (FIG. 2H), also supporting the role of CCR10 in suppression of Th17 functions.

Figures 12A, 12B:
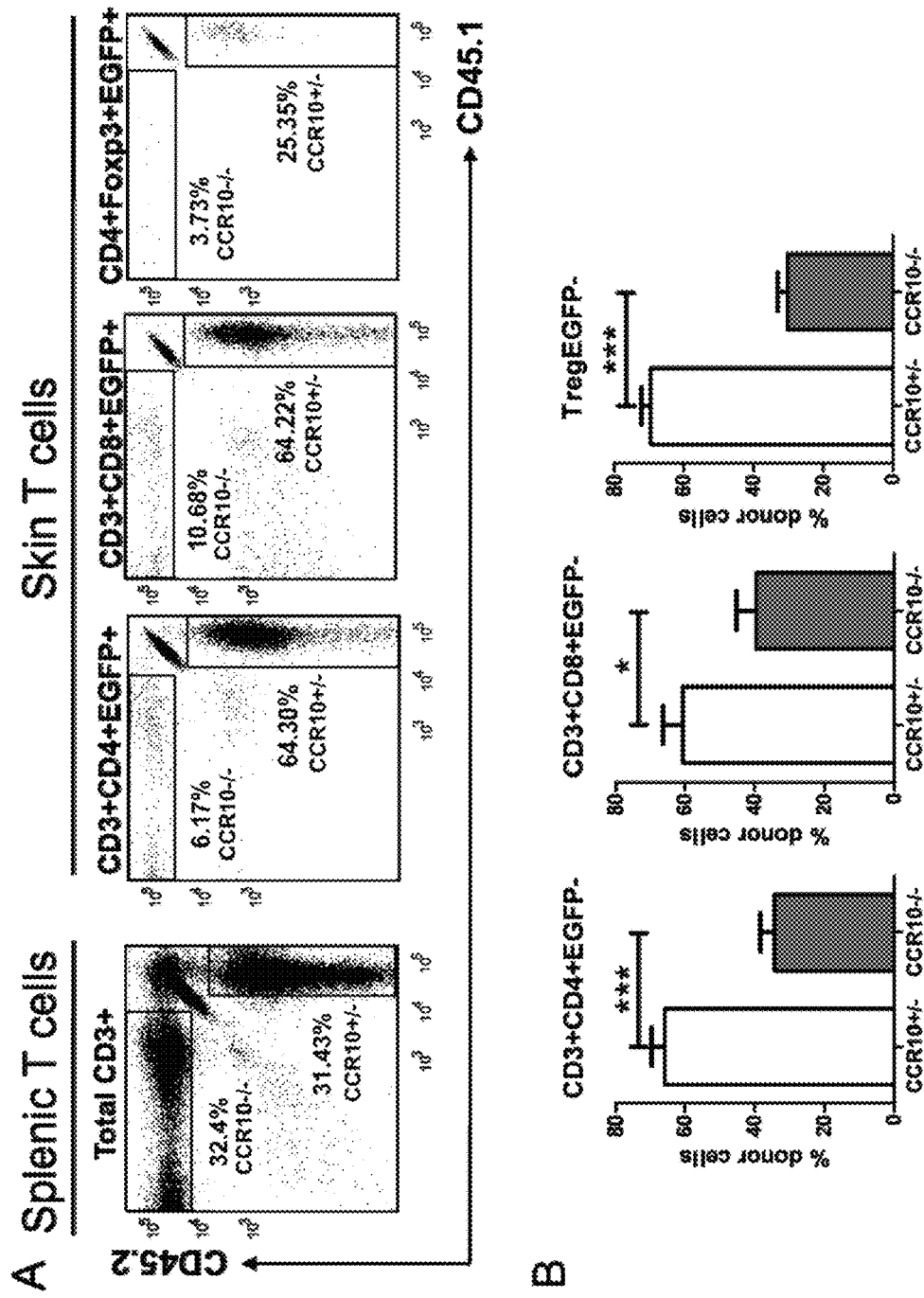
FIGS. 12A and 12B is a series of images showing Treg and Teff cells in the skin of CCR10$^{-/-}$ mice.

To determine whether CCR10 is directly involved in regulating the skin Treg and Teff subsets, competitive bone marrow (BM) co-transfer experiments were performed in which similar numbers of CCR10$^{-/-}$ and CCR10$^{+/-}$ BM cells were injected into irradiated WT mice. EGFP$^+$ CD8$^+$, CD4$^+$ and Foxp3$^+$ T cell subsets of the CCR10$^{-/-}$ donor were all greatly under-represented in the skin compared to corresponding populations of the CCR10$^{+/-}$ donor (FIG. 2J, FIG. 12A). In addition, EGFP$^-$ CD8$^+$, CD4$^+$ and Treg cell subsets of the CCR10$^{-/-}$ donor were also under-represented (to lesser extent than the EGFP$^+$ subsets) in the skin compared to corresponding populations of the CCR10$^{+/-}$ donor (FIG. 12B). Since EGFP$^-$ cells do not express CCR10, the effect of CCR10-KO on these cells is likely secondary to the effect of CCR10-KO on EGFP$^+$ cells. Furthermore, EGFP$^+$ skin CD4$^+$ T cells of the CCR10$^{-/-}$ donor still had higher percentages of Th17 cells with higher IL17 MFI staining than those of the CCR10$^{+/-}$ donor (FIG. 2K), demonstrating an intrinsic regulatory role of CCR10 in maintenance and function of the skin-resident T cells.

Figures 3A, 3B, 3C, 3D:
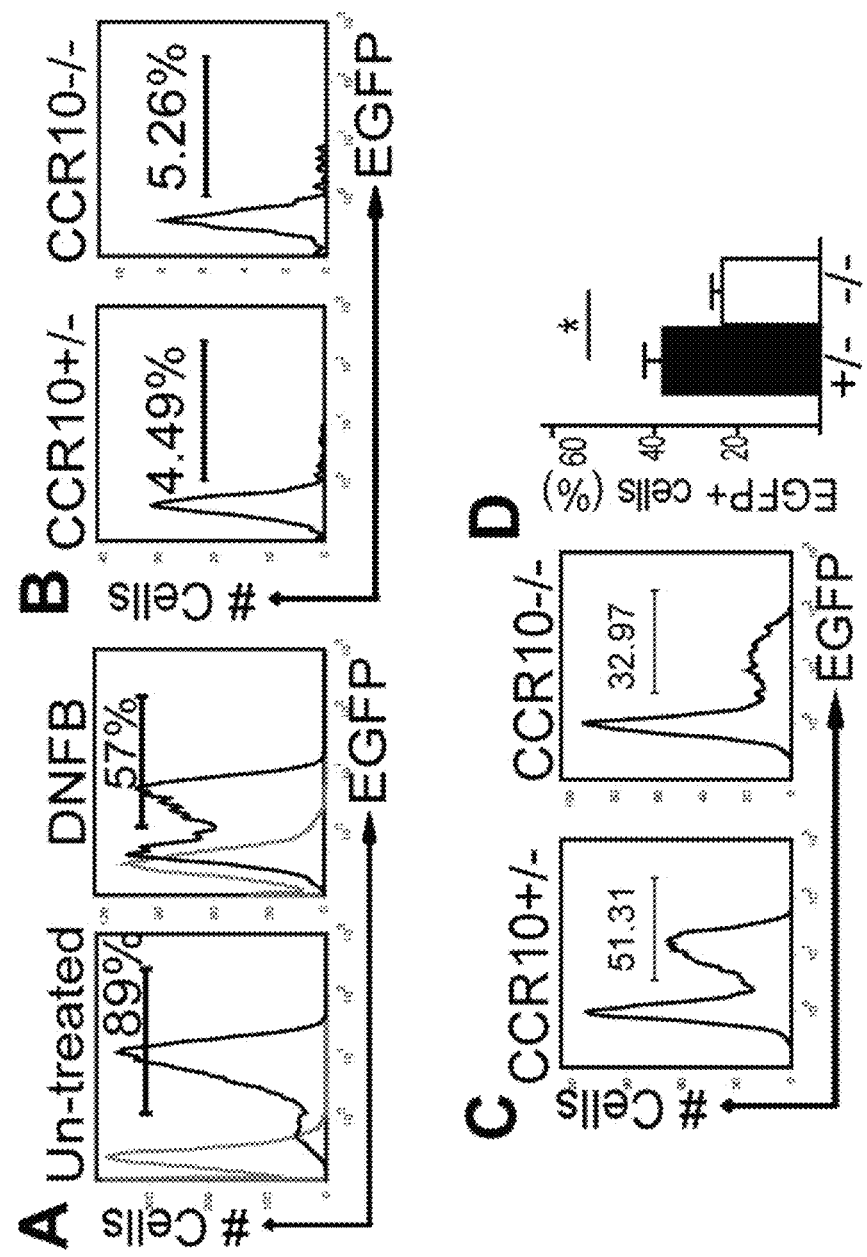
FIGS. 3A through 3G, is a series of images demonstrating that Treg cells are critical for maintenance of CCR10$^+$ memory-like resident T cells in the skin.

Treg Cells-Regulated Immune Homeostasis is Critical for Maintenance of CCR10$^+$ Memory-Like Resident T Cells in the Skin While the imbalanced presence and dysregulated function of skin-resident Treg vs. Teff cells are consistent with the over-reactive innate response in CCR10$^{-/-}$ mice, the normal CHS response (FIG. 1A) suggests that CCR10 is not critical for migration of infiltrating effector T cells during the inflammation. It was noted that DNFB-inflamed skin of the CHS assay had significantly lower percentages of CCR10$^+$ T cells than untreated skin (FIG. 3A), which suggest that CCR10 is not expressed on many new infiltrating T cells and might explain the different effects of CCR10-knockout on skin-resident T cells under steady conditions vs. infiltrating T cells during inflammation. Dissecting this further, EGFP$^-$ splenic T cells of CCR10$^{+/-}$ or CCR10$^{-/-}$ mice were transferred into Rag1$^{-/-}$ mice and analyzed the skin-infiltrating donor T cells different time after induction of CHS. At the peak of inflammation (1 day after the DNFB challenge), only few skin-infiltrating T cells were EGFP$^+$ (FIG. 3B). In marked contrast, 1 month after the DNFB challenge when inflammation was resolved, about half of skin T cells of CCR10$^{+/-}$ donor were EGFP$^+$, and the percentage of EGFP$^+$ skin T cells of CCR10$^{-/-}$ donor was significantly lower than that of CCR10$^{+/-}$ donor (FIG. 3C-3D). Since the skin EGFP$^+$ T cells of the donor in Rag1$^{-/-}$ recipients had preferentially displayed memory phenotypes from early on even at the active phase of inflammation (FIG. 3E), these results suggest that CCR10 is preferentially imprinted on memory T cell progenitors for their maintenance in the skin after resolution of inflammation but not on effector T cells for their skin infiltration during inflammation.

Figures 3E, 3F, 3G:
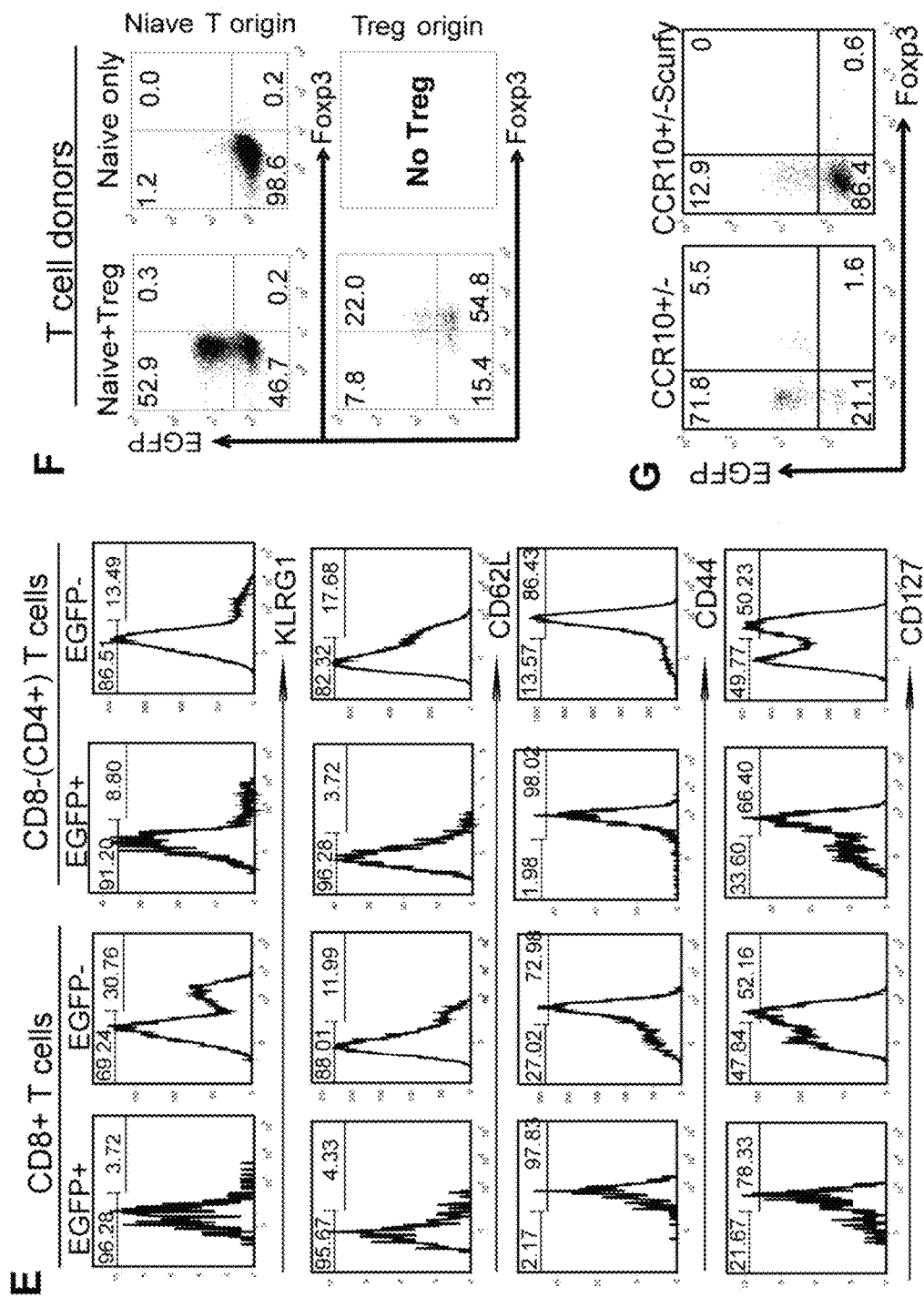

Experiments were designed to test this notion further using two chronic inflammation models. First, Treg-depleted splenic naïve CD4+ T cells were transferred into Rag1−/− mice, which induces the inflammation in the skin (and other tissues) due to absence of Treg cells (Hong, K., et al., 1999, *J Immunol* 162:7480-7491 and Ma, H. L., et al., 2008, *J Clin Invest* 118:597-607). Nearly no skin T cells of the donor expressed EGFP in the recipients two months after the transfer (FIG. 3F, right), while in Rag1−/− mice receiving splenic naïve CD4+ T and Treg cells, high percentages of skin T cells of both donor origins were EGFP+ (FIG. 3F, left), indicating that Treg-regulated immune homeostasis is critical for establishment and maintenance of CCR10+ T cells in skin. Consistent with this, only a few skin T cells were EGFP+ in Foxp3-deficient Scurfy mice, which lack Treg cells and develop the skin inflammation soon after the birth (FIG. 3G). Together, these results reveal an important role of CCR10 in a positive feedback circuit of immune homeostatic regulation in the skin where CCR10 maintains balanced presence and function of resident Treg vs. Teff cells, which in turn help to establish a homeostatic environment important for maintenance of the CCR10+ resident T cells.

CCR10 is Critical for Localization of CCR10+ T Cells into the Homeostatic Skin

A drawback with the DNFB/FITC model is difficulty to follow antigen-specific T cells. Therefore, CCR10−/− mice were crossed to OT-I or OT-II mice that carry CD8+ or CD4+ T cells expressing transgenic αβTCRs specific for OVA antigens respectively. Purified naïve splenic EGFP− CCR10+/− and CCR10−/− OT-I (or OT-II) T cells were transferred into WT mice, followed by epicutaneous immunization with OVA on the ear (twice with a week interval) (Campbell, J. J., et al., 2007, *J Immunol* 178:3358-3362). One week after the second immunization, the inflamed ear and un-inflamed torso skin were analyzed for the OVA-specific T cells.

Figures 4A, 4B, 4C:
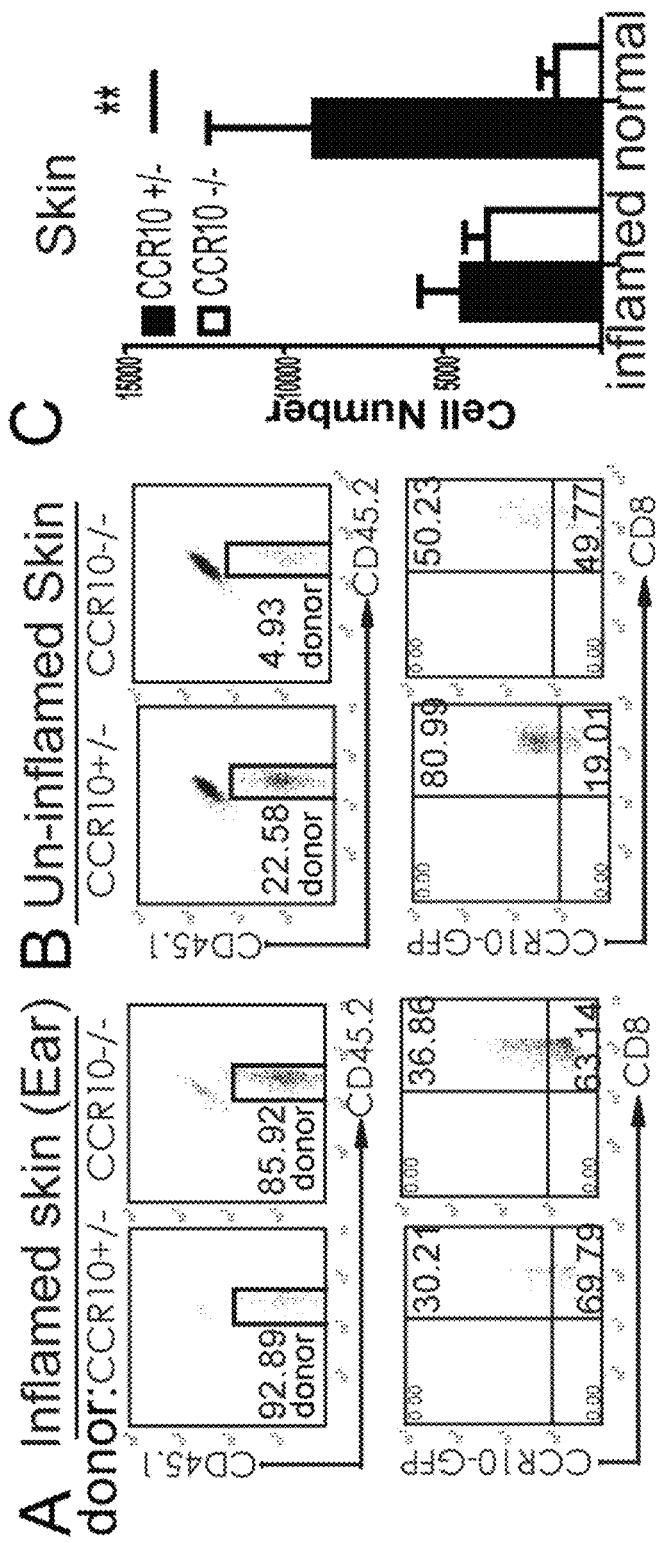
Figures 13A, 13B, 13C:
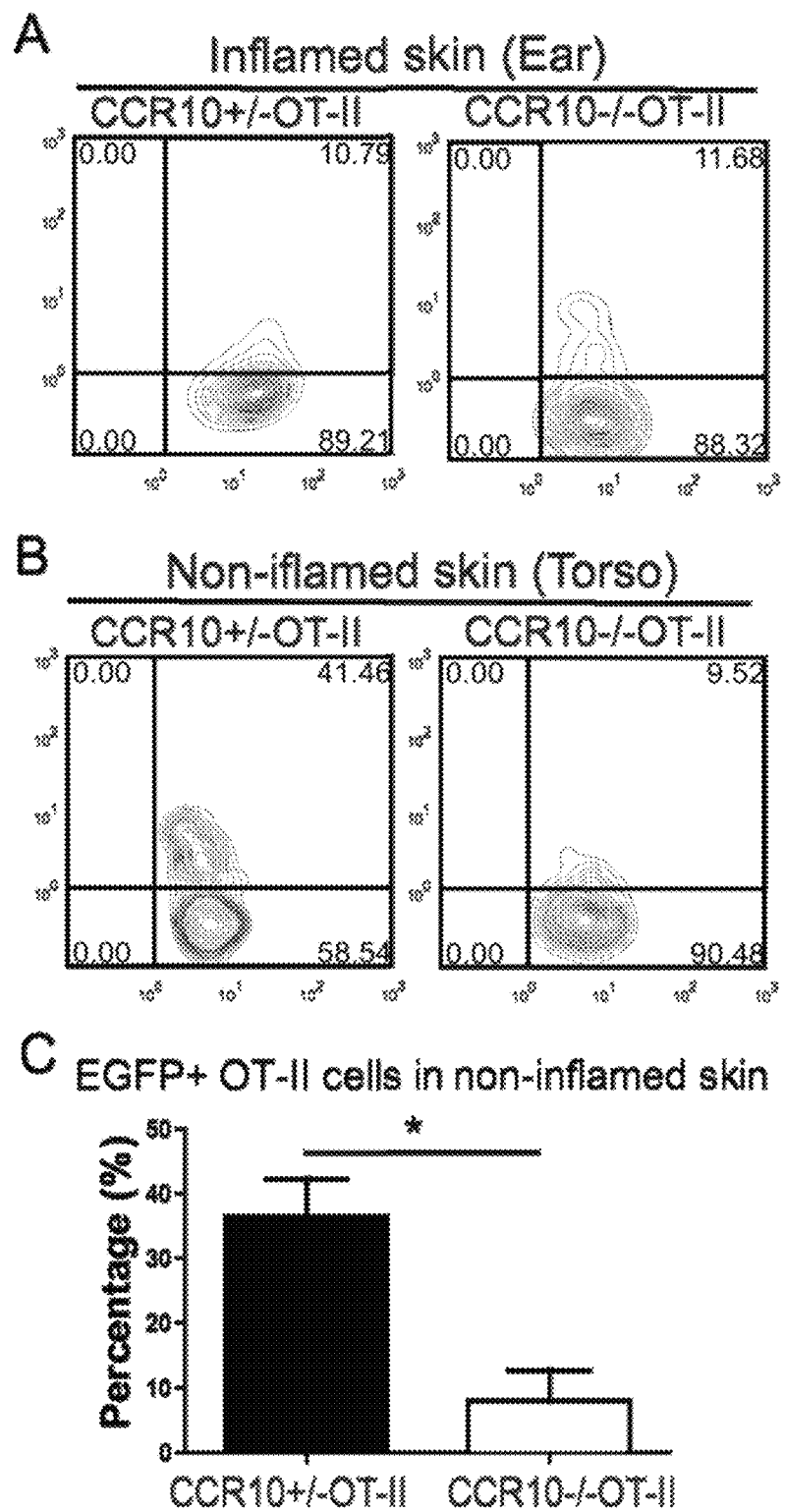
FIGS. 13A through 13C, is a series of images demonstrating that CCR10 is critical in localization of CCR10+ CD4+ OT-II T cells into homeostatic skin.

In the inflamed ear skin, the newly infiltrating OVA-specific CD8+ OT-I T cells accounted for the majority of total T cells (FIG. 4A). However, only a small portion of them was EGFP+ and CCR10-KO did not affect percentages of the EGFP+ OT-I T cells in the ear (FIGS. 4A and 4C). In striking contrast, much higher percentages of infiltrating OT-I T cells in the untreated (and un-inflamed) torso skin were EGFP+ and CCR10-KO significantly reduced the EGFP+ OT-I cells in the untreated skin (FIGS. 4B and 4C), revealing that CCR10 is critical for localization of the CCR10+ CD8+ T cells into un-inflamed but not inflamed skin even in the same mouse. Similarly, CCR10 is also required for localization of CCR10+ CD4+ OT-II T cells into the untreated skin but dispensable for their localization into inflamed skin stimulated by the Ova immunization (FIG. 13).

Defective Resolution of Immune Memory Responses in Skin of CCR10−/− Mice

Figures 5A, 5B, 5C, 5D:
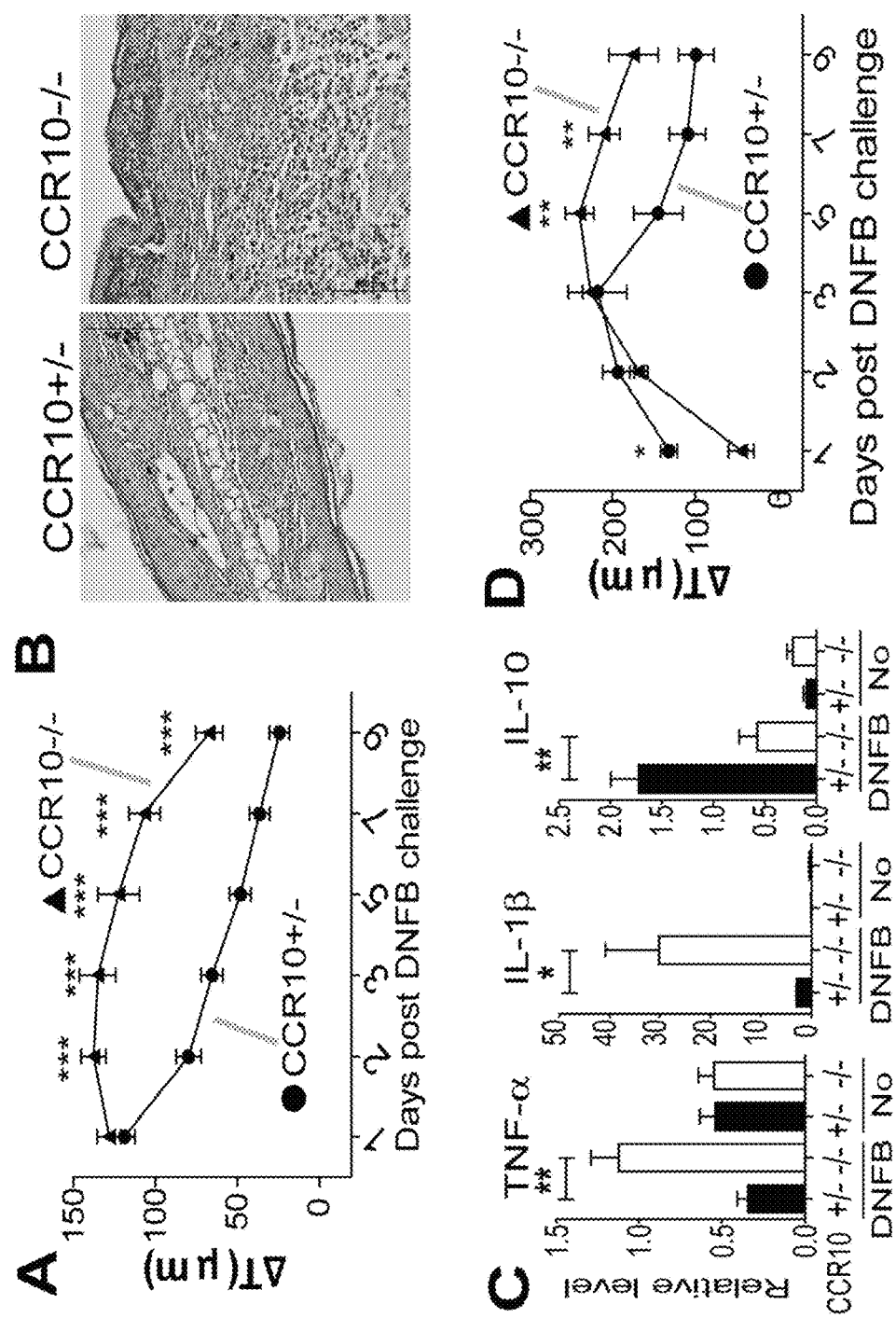
FIGS. 5A through 5D, is a series of images demonstrating defective resolution of immune memory responses in the skin of CCR10$^{-/-}$ mice.

Skin-resident memory T cells play important roles in memory responses (Clark, R. A., 2010, *J Invest Dermatol* 130:362-370, Gebhardt, T., et al., 2009, *Nat Immunol* 10:524-530, Jiang, X., et al., 2012, *Nature* 483:227-231 and Mackay, L. K., et al., 2012, *Proc Natl Acad Sci USA* 109:7037-7042). CCR10−/− mice were tested using a memory CHS assay, in which mice were challenged with DNFB one month (instead of five days in a classic CHS assay) after the initial DNFB sensitization. Compared to CCR10+/− mice, CCR10−/− mice had strikingly prolonged inflammation in the skin, associated with enhanced TNF-α and IL-1β and reduced IL-10 expression (FIG. 5A-5C), suggesting that the imbalanced maintenance and function of the resident Treg vs. Teff cells also causes defective resolution of memory responses. Further supporting this notion, memory CHS responses in Rag1−/− mice transferred with splenic CCR10−/− T cells, which had defective maintenance of the donor-derived EGFP+ memory-like T cells in the skin after resolution of inflammation in classic CHS (FIG. 3C-3D), were also prolonged compared to the recipients of CCR10+/− T cells (FIG. 5D). Notably, while there was no difference in the early memory response between immunized CCR10+/− and CCR10−/− mice the first day after re-application of DNFB (FIG. 5A), Rag1−/− mice receiving CCR10−/− T cells had slower memory responses than Rag1−/− mice receiving CCR10+/− T cells (FIG. 5D, Day 1). The different effects of CCR10-KO on the early response between the two models are likely because in direct comparison of CCR10−/− and CCR10+/− mice, the memory response could be affected by CCR10-regulated αβT as well as other cells while in Rag1−/− mice transferred with splenic T cells, some of the CCR10-regulated cells such as the epidermis-resident γδT cells are not reconstituted (Jin, Y., et al., 2010, *J Immunol* 185:5723-5731). The epidermis-resident γδT cells are known to impact the skin immune response (Girardi, M., et al., 2002, *J Exp Med* 195:855-867).

Figures 6A, 6B, 6C, 6D:
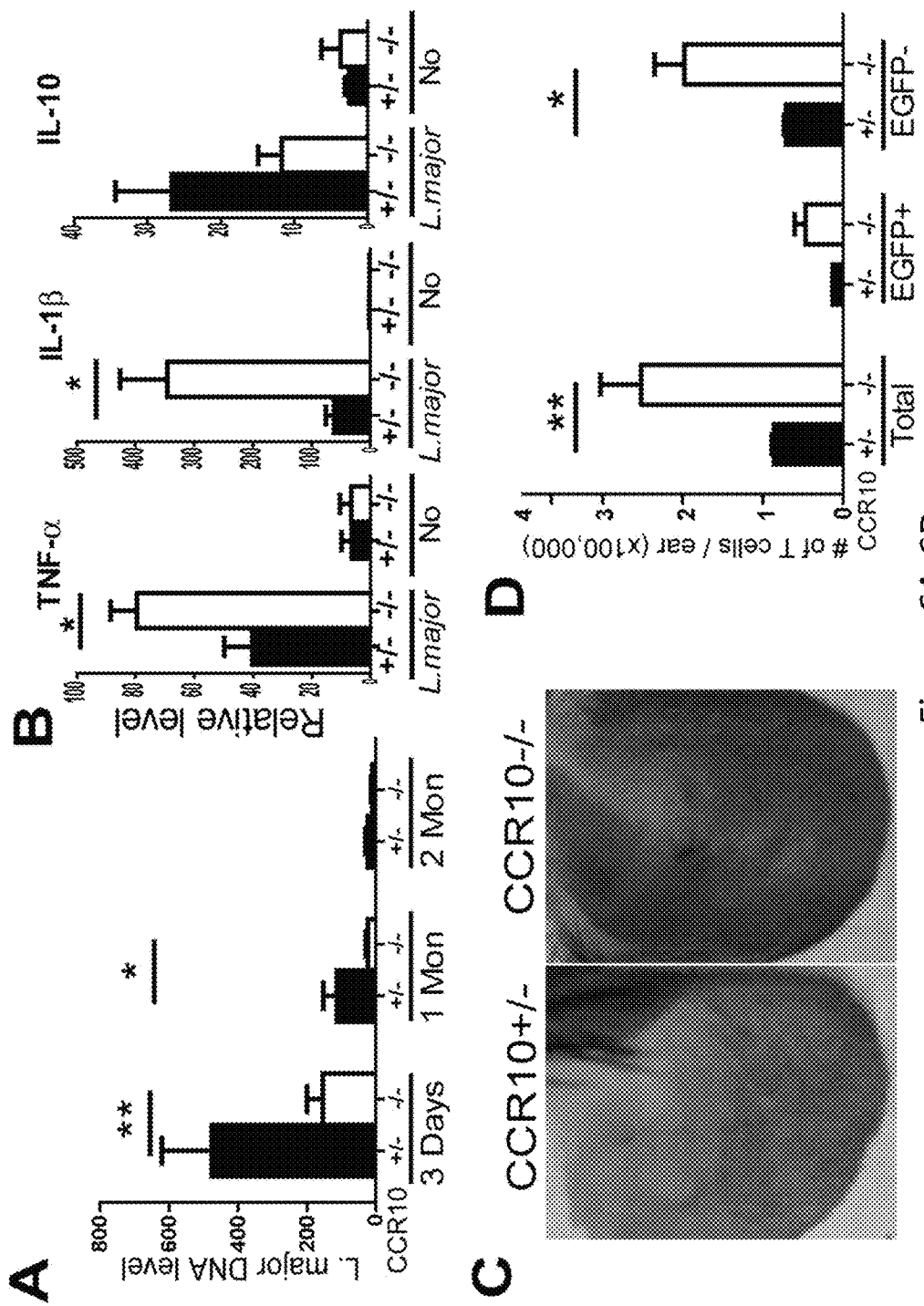
FIGS. 6A through 6D, is a series of images demonstrating enhanced immune responses to and accelerated clearance of Leishmania major infection in skin of CCR10$^{-/-}$ mice.
Figure 14:
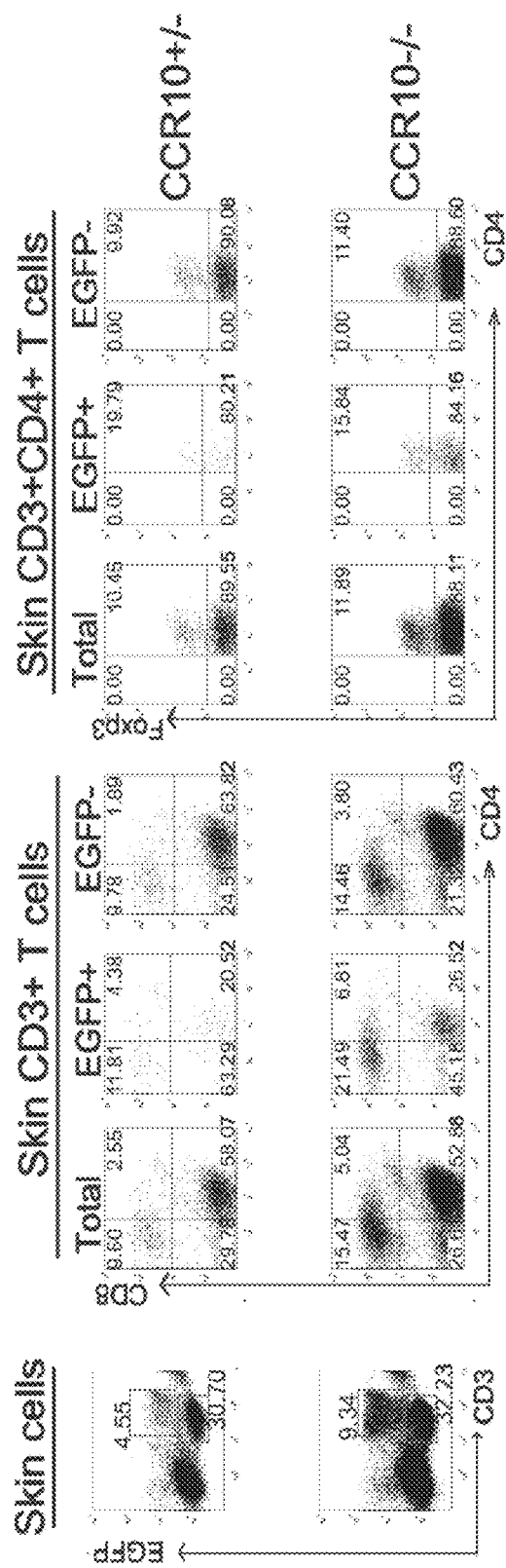
FIG. 14 is an image of a representative flow cytometric analysis of T cells isolated from *L. major*-infected ears of CCR10$^{-/-}$ vs. CCR10$^{+/-}$ mice for different T subsets and their expression of EGFP. The mice were analyzed one month after the infection.

Enhanced Immune Response to and Accelerated Clearance of *Leishmania major* Infection in the Skin of CCR10−/− Mice The finding of the important role of CCR10 in regulating the skin-resident Treg and Teff cells to prevent over-active immune responses predicts that targeting CCR10 might enhance immune responses against skin-specific infections and other diseases. As a test, CCR10−/− mice was infected with *Leishmania major*, a parasitic pathogen that could manipulate Treg cells to evade immune attack for its long-term survival in skin (Belkaid, Y., et al., 2002, *Nature* 420:502-507). Indeed, CCR10−/− mice cleared the parasite much faster than CCR10+/− mice (FIG. 6A). Consistent with an enhanced immune response, CCR10−/− mice had higher TNF-α and IL-1β production than CCR10+/− mice early post the infection (FIG. 6B), as in the case of chemical challenge (FIG. 1). In addition, 1 month post the infection, significantly higher percentages of CCR10−/− mice developed visible inflammation at infection sites than CCR10+/− mice did [76% (13/17) vs. 38% (8/21), P=0.025](FIG. 6C), and the infected ears of CCR10−/− mice had many more T cells, most of which were EGFP−, than the CCR10+/− controls (FIG. 6D; FIG. 14), demonstrating that absence of CCR10 increased effector T cell response for more efficient clearance of the infection in the skin.

Significant Percentages of T Cells in Healthy Human Skin Express CCR10

Figures 7A, 7B:
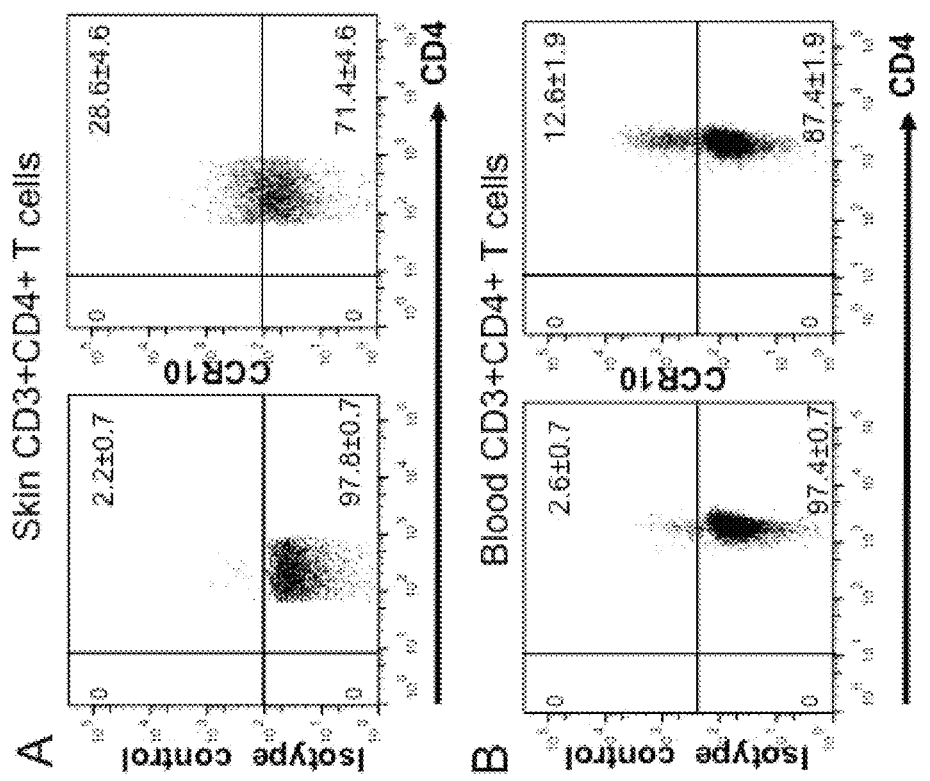
FIGS. 7A and 7B, is a series of images demonstrating preferential expression of CCR10 by T cells of the healthy human skin.
Figure 11:
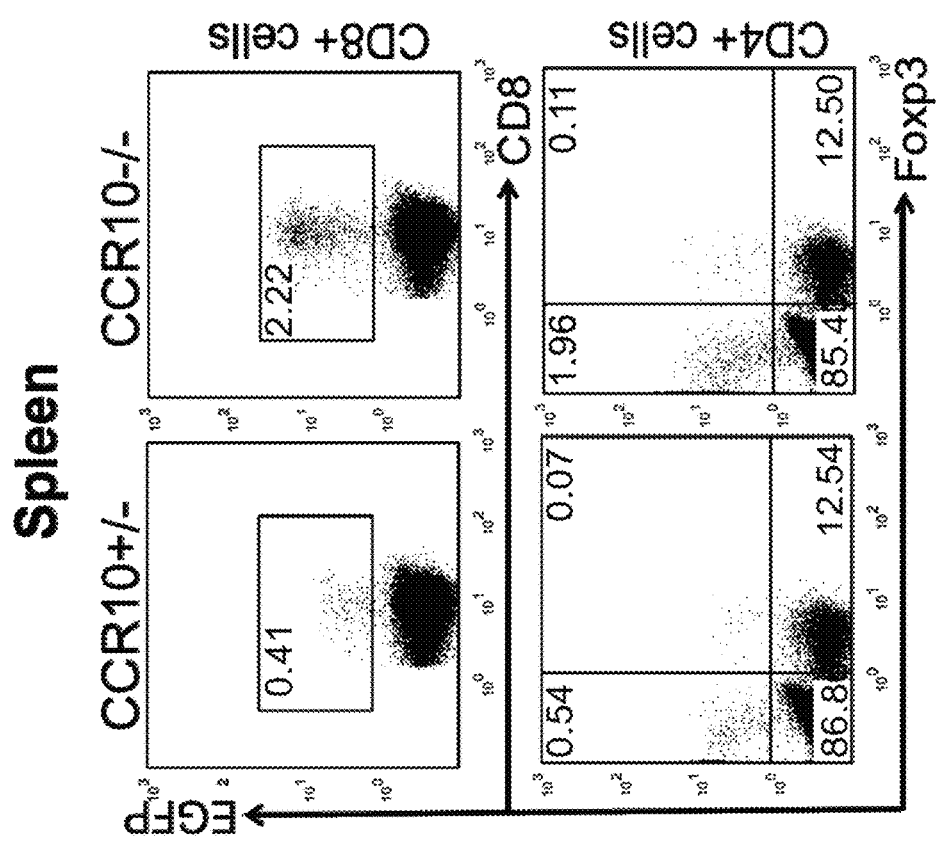
FIG. 11 is an image of a representative FACS analysis of gated splenic CD3+CD8+ (top) and CD3+CD4+ (bottom) T cells for EGFP+ subsets in CCR10$^{-/-}$ and CCR10$^{+/-}$ mice.

In humans, all blood CCR10+ T cells display memory cell markers (Morales, J., et al., 1999, *Proc Natl Acad Sci USA* 96:14470-14475 and Soler, D., et al., 2003, *Blood* 101:1677-1682). Therefore, CCR10/CCL27 might promote preferential maintenance of the CCR10+ memory-like T cells in the healthy skin. However, direct evidence of the enrichment of CCR10+ T cells in the skin is lacking Therefore, the T cells isolated from human healthy skin were analyzed for their expression of CCR10. Compared to T cells of blood, significantly higher percentages of T cells isolated from the normal human skin expressed CCR10 (FIG. 7), correlating with the different expression of CCR10 on circulating and skin-resident T cells in mice (FIG. 2 and FIG. 11). The similar expression pattern of CCR10 in the skin T cells of mice and humans suggests that CCR10 might function in the similar fashion in both human and mouse skin.

Figure 15:
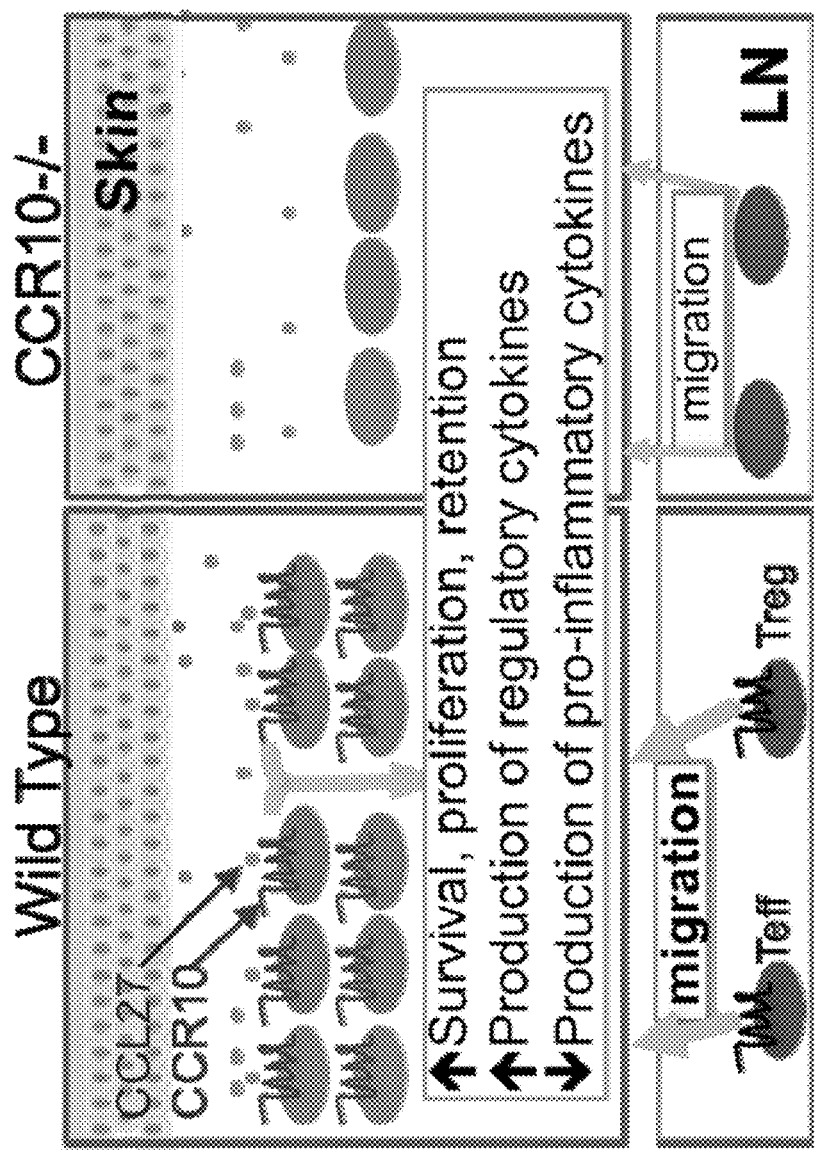
FIG. 15 is a schematic illustration of roles of CCR10 in regulation of skin Treg and Teff cells under homeostatic conditions.

CCR10 Regulates Balanced Maintenance and Function of Resident Regulatory and Effector T Cells to Promote Immune Homeostasis in Skin CCR10/CCL27 are implicated in various skin allergy and inflammatory diseases but the in vivo function of the pair has been elusive, hindering the effort in understanding their involvement in the disease development (Homey, B., et al., 2002, *Nat Med* 8:157-165). In this report, definite evidence that CCR10 is critical in the regulation of immune homeostasis and resolution of inflammation is provided, which is an advance from the current focus on the role of CCR10 as a homing molecule for infiltrating T cells to promote the immune response in the skin. Mechanistically, CCR10 could potentially function in several aspects to regulate the skin T cells (illustrated in FIG. 15). First, CCR10 is critical in migration of $CCR10^+$ memory (or memory-like) T cell precursors into the skin under homeostatic conditions while it is dispensable for infiltration of T cells into the inflamed skin. In addition, CCR10 expressed on the skin-resident Treg and Teff cells is important for their balanced maintenance in the skin under homeostatic conditions, potentially by regulating their retention, proliferation and survival in the skin. Furthermore, the results presented herein also suggest that CCR10 might signal to regulate functions of the $CCR10^+$ skin-resident T cells such as their production of inflammatory and regulatory cytokines. In absence of CCR10, the dysreguated maintenance and functions of resident Teff and Treg cells in the skin could result in the over-active immune response and impaired resolution of skin inflammation. In light of the finding of CCR10 as a critical regulator of skin immune homeostasis in mice, roles of the CCR10/CCL27 axis in the skin allergy and inflammatory diseases in patients need to be carefully investigated before targeting the axis for treatment of the diseases. It is possible that the upregulated expression of CCL27 in the inflamed skin is secondary to the inflammation for a purpose of inflammation regulation. Therefore, developing a strategy to increase the number and activity of the CCR10+ resident regulatory T cells might help to restore the immune homeostasis and treat inflammatory diseases in the skin.

Considering both resident Treg and Teff cells are reduced in the skin of CCR10-knockout mice, the over-active immune response to the skin stimulation is likely due to impaired presence and dysregulated function of both populations. Consistent with this, the results presented herein suggests that CCR10 has an intrinsic regulatory role in controlling function of Teff cells (Th17), which is in addition to potential regulatory effect of Treg cells on these effector T cells. Although mechanisms underlying the intrinsic regulatory functions of CCR10 in the Teff and Treg cells are not clear, the results presented herein is reminiscent of functions of some other T cell regulatory receptors such as PD-1 and CTLA-4 that inhibit Teff cell functions and enhances Treg cell functions (Francisco, L. M., et al., 2009, *J Exp Med* 206:3015-3029 and Krummel, M. F., et al., 1995, *J. Exp. Med.* 182:459-465). Considering the importance of balanced production of inflammatory and regulatory cytokines in immune homeostasis and inflammation, it would be important to figure out the mechanism of CCR10 in regulating T cell activation and inflammatory cytokine production in the future. In addition, addressing the origin of $CCR10^+$ memory (or memory-like) Teff and Treg cells is another important question to understand their functions.

CCR10-knockout affects the presence of CD8+ Teff and Treg subsets in the skin to a larger extent than CD4+ Teff cells, suggesting that the different resident T cell subsets are intrinsically different in their requirements of CCR10 for maintenance. While the underlying mechanism is not clear, it seems to be associated with the different mobility and expression of skin retention molecules of the different T cells subsets (Sather, B. D., et al., 2007, *J Exp Med* 204:1335-1347, Gebhardt, T., et al., 2011, *Nature* 477:216-219 and Sharma, R., et al., 2009, *J Immunol* 183:1065-1073). Of note, the skin-resident $CD8^+$ memory T cells do not move while the $CD4^+$ cells are highly mobile (Sather, B. D., et al., 2007, *J Exp Med* 204:1335-1347, Gebhardt, T., et al., 2011, *Nature* 477:216-219 and Sharma, R., et al., 2009, *J Immunol* 183:1065-1073). While mobility of skin-resident Treg cells is well studied, they express the skin adhesion molecules CD103 as the resident $CD8^+$ cells do while the resident $CD4^+$ Teff cells do not (Sather, B. D., et al., 2007, *J Exp Med* 204:1335-1347, Gebhardt, T., et al., 2011, *Nature* 477:216-219 and Sharma, R., et al., 2009, *J Immunol* 183:1065-1073).

While a predominantly net effect of CCR10-knockout on the skin immune response is the over-reactive and prolonged inflammation, CCR10 might be important for an efficient effector memory T cell response. $Rag1^{-/-}$ mice reconstituted with $CCR10^{-/-}$ T cells had a slower and prolonged memory response compared to those reconstituted with $CCR10^{+/-}$ T cells, suggesting that both effector and resolution phases of the memory response are impaired. Likely, the CCR10-dependent efficient and balanced maintenance of resident Teff and Treg memory T cells in the skin allows a rapid effector T response to a challenge as well as proper resolution of the effector response after clearance of the challenge. Such efficient effector and regulatory responses are important for preservation of the function of skin while dealing with harmful challenges of environments. Dysregulation of either phase of the response could result in skin diseases.

Example 2: CCR10-Regulated ILC in Prevention of Skin Inflammation

The set of experiments were designed to evaluate the role of CCR10 in preventing skin inflammation.

ILC Cells

ILC cells are a family of newly identified innate lymphocytes preferentially enriched in barrier tissues such as the intestine and skin and involved in the local tissue homeostasis and inflammation. ILCs do not express cell-surface markers associated with other immune cell lineages (lineage marker-negative or LIN–) but express the common hematopoietic lineage marker CD45 and surface molecules commonly associated with lymphocytes such as CD90 and CD127. Based on their developmental pathways and functional potentials in analog to the different T helper cell (Th) subsets, ILCs were divided into three major groups (ILC1-3). ILC1 comprises natural killer (NK) cells and other ILCs that produce IFN-γ. ILC2 cells predominantly express Th2-type cytokines such as IL-5 and IL-15, and ILC3 cells produce Th-17/22 type cytokines such as IL-17 and IL-22. Through the production of unique cytokines and direct cell-cell interaction, the different groups of ILCs have been reported to act on various other subsets of immune cells, such as T cells, mast cells, eosinophils and macrophages, and epithelial cells.

Function and Regulation of ILCs in the Skin Immune Activation and Homeostasis

ILCs were only recently found in the skin and involved in the skin inflammation as well as homeostatic regulation. One early study reported that IL-17 producing ILCs (belonging to the ILC3 group) could infiltrate the inflammatory skin of mice in an Imiquimod (Aldara) cream-induced psoriasis model to contribute to the disease development. More recently, several groups reported that ILC2 cells were involved in mediating the skin inflammation in atopic dermatitis. In addition, ILC2 cells were found to reside in the healthy skin where they interact with mast cells, implicating them in regulation of other skin-immune cells for the homeostatic maintenance. However, mechanisms regulating the skin-specific localization of ILCs and their various functions are not clear.

CCR10 is Expressed on Most ILCs of Homeostatic Skin and Important for the Skin Immune Homeostasis A strain of CCR10-knockout/EGFP-knockin mice in which the CCR10 coding region was replaced with a DNA sequence coding for enhanced green fluorescent protein (EGFP) as a reporter for CCR10 was generated. Using heterozygous and homozygous CCR10-knockout/EGFP-knockin (CCR10$^{+/EGFP}$ and CCR10$^{EGFP/EGFP}$, or CCR10$^{+/-}$ and CCR10$^{-/-}$ for simplicity) mice, expression of CCR10 and its roles in skin immune cells were assessed. It was found that the CCR10+ ILCs are generated under homeostatic conditions only in the skin-draining lymph nodes (sLN), and dependent on CCR10 as well as CCR6 for localization in the skin. The CCR10+ ILCs were capable of producing more IL-17 as well as IL-5 than their CCR10− counterparts, and most of them expressed high levels of MHCII, suggesting their role in regulation of CD4+ T cells. Supporting this, it was found that CCR10+ sILCs were important in homeostatic maintenance of skin regulatory T (Treg) cells to prevent effector T (Teff) cells-induced skin inflammation. Reciprocally, the generation and localization of CCR10+ sILCs required Treg cell-regulated homeostatic environments and were suppressed under inflammatory conditions, indicating a cross regulation of CCR10+ ILC and T cells in the immune homeostatic maintenance in the skin.

CCR10+ ILCs are the Dominantly Active Population of Skin-Specific ILCs Under Homeostatic Conditions Based on the EGFP reporter of CCR10 expression in CCR10$^{+/EGFP}$ (or CCR10$^{+/-}$ for simplicity) mice, the majority of CD3−Lin−CD127+CD90+ ILC cells within the CD45+ population of the skin expressed CCR10 (EGFP+) but those of mucosal tissues such as intestines and lungs did not (FIG. 16a-b). CCR10+ and CCR10− skin_ILCs expressed other common epithelial tissue-homing and adhesion molecules CCR6, CD103 and CD69 (FIG. 16c), indicating that they were all resident ILCs.

CCR10+ and CCR10− skin_ILCs also both expressed the lymphocyte activation marker CD44 (FIG. 16d). However, significantly higher percentages of CCR10+ skin_ILCs were Ki-67+ than CCR10− skin_ILCs (FIG. 16d), suggesting that CCR10+ skin_ILCs were more activating cells. Consistent with this notion, CCR10+ skin_ILCs had higher percentages of IL-17+ (ILC3-like) and IL-5+ (ILC2-like) cells (FIG. 16e). Few CCR10+ or CCR10− skin_ILCs produced IFN-γ or IL-10 (FIG. 16e).

Previous studies with intestinal ILCs found that a fraction of intestinal ILC3 cells expressed high levels of MHCII with regulatory antigen-presenting cell (APC) capacities {Hepworth, 2013 #171}. We analyzed CCR10+ and CCR10− skin_ILCs for their expression of MHCII and other co-stimulatory and co-inhibitory molecules. Markedly, most CCR10+ skin_ILCs expressed high levels of MHCII while CCR10− skin_ILCs expressed no or lower levels of MHCII (FIG. 16f). In addition, most CCR10+ skin_ILCs expressed the co-inhibitory molecule PD-L1 while they expressed no or low levels of other co-stimulatory or co-inhibitory molecules CD80, CD86, PD-L2, B7x, B7h, B7H3, OX40L and CD40 (FIG. 16g), suggesting their potentials as regulatory APCs.

CCR10+ ILCs are Active ILCs Found in Skin-Draining Lymph Nodes but not Other Secondary Lymphoid Organs To understand the process for the preferential establishment of CCR10+ ILCs in the skin, we searched for CCR10+ ILCs in skin-draining LNs (sLNs) and other lymphoid organs. Strikingly, most ILCs of sLNs (sLN_ILCs) expressed high levels of CCR10 while ILCs of BM, spleens or intestine-draining mesenteric lymph nodes (mLNs) were CCR10− (FIG. 16h-i). Similar to CCR10+ skin_ILCs, the vast majority of CCR10+ sLN_ILCs expressed CCR6 and CD103 and most of them expressed CD69 (FIG. 16j).

The similarity of CCR10+ skin_ILCs and sLN_ILCs supports the idea that skin-specific CCR10+ ILCs might be selectively programmed in sLNs. Consistent with this, CCR10+ sLN_ILCs uniformly expressed high levels of CD44 (FIG. 16k), suggesting that they were activated cells. Confirming this, significantly high percentages of CCR10+ sLN_ILCs were at the proliferating phase based on their expression of Ki-67 (FIG. 16k). In addition, CCR10+ sLN_ILCs expressed high levels of IL-17 and IL-5 but no IFN-γ or IL-10 (FIG. 16l). Like CCR10+ skin_ILCs, the vast majority of CCR10+ sLN_ILCs expressed high levels of MHCII (FIG. 16m). Together, these results suggest that in sLNs, activated ILCs are predominantly programmed to acquire high expression of CCR10 and other skin-homing molecules for their migration into the skin to replenish the local ILC pool.

CCR10 and CCR6 are Critical for Localization of CCR10+ sILCs in(to) the Skin

Figures 17A, 17B, 17C:
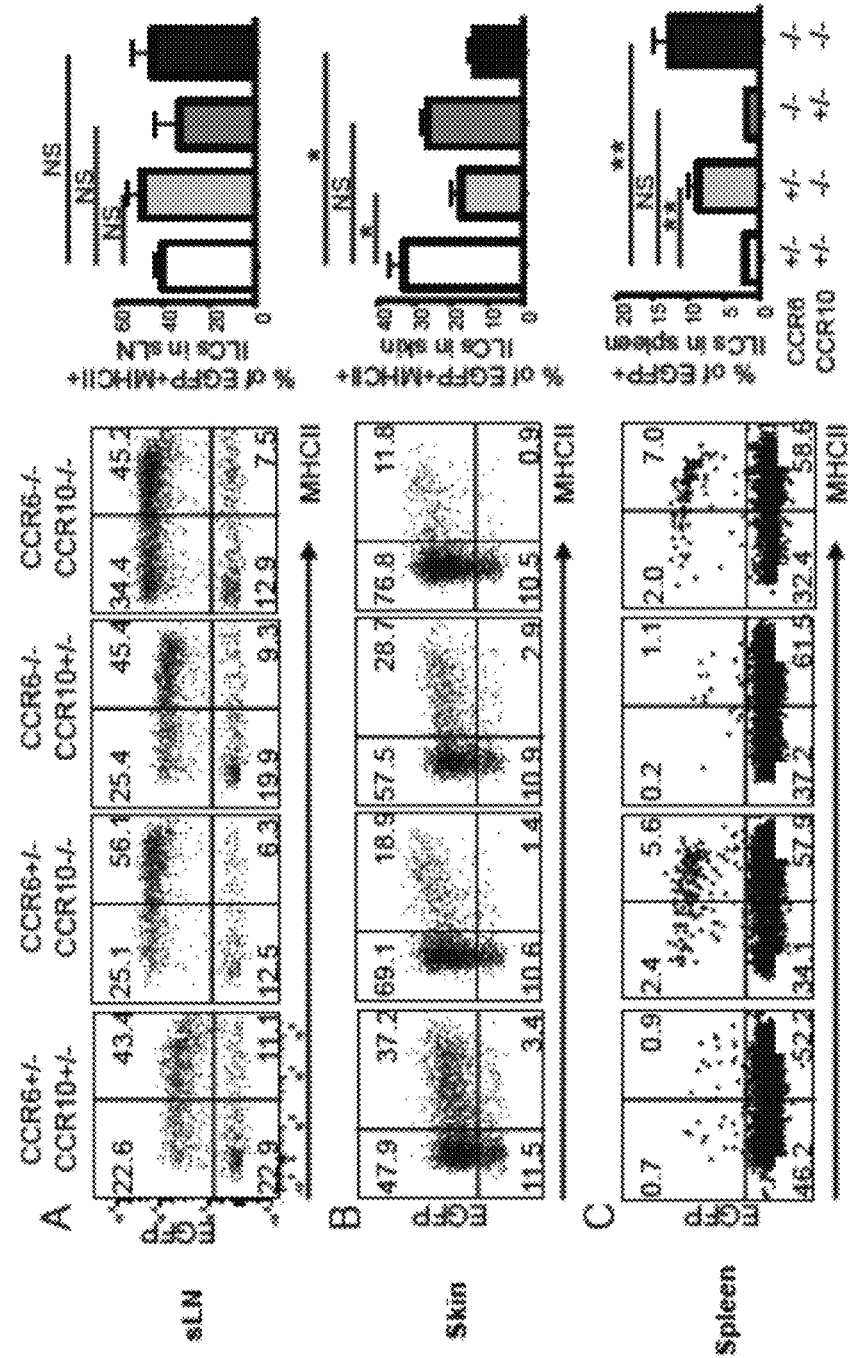
FIGS. 17A through 17C, is a series of images comparing CCR10 (GFP)+ ILCs in sLN (FIG. 17A), skin (FIG. 17B) and spleens (FIG. 17C) of CCR10$^{-/-}$, CCR10$^{+/-}$CCR6$^{-/-}$, CCR10$^{-/-}$CCR6$^{-/-}$ and control CCR10$^{+/-}$ littermate mice. Using the mice carrying CCR10$^{+/-}$ alleles is to visualize CCR10 expression with the EGFP reporter. Representatives of flow cytometry of ILCs (CD45+CD3−Lin−) of the different strains were shown on the left. Bar graphs show percentages of EGFP+MHCII+ cells among ILCs in sLN (N=3) and skin (N=3), as well as percentages of EGFP+ cells among ILCs in spleens (N=5). *P<0.05, **P<0.005.

Experiments were designed to compare CCR10$^{EGFP/EGFP}$ and CCR10$^{+/EGFP}$ littermates for EGFP+ ILCs in sLNs, skin and spleens to determine roles of CCR10 in specific migration and establishment of CCR10+ ILCs in(to) the skin. EGFP+ ILCs in CCR10$^{EGFP/EGFP}$ mice are "CCR10+ wannabe" ILCs that do not express CCR10 proteins. Compared to CCR10$^{+/EGFP}$ littermates, CCR10$^{EGFP/EGFP}$ mice had similar, if not higher, percentages and numbers of EGFP+ MHCII+ ILCs in sLNs (FIG. 17A). In contrast, there was a specific decrease of EGFP+MHCII+ ILCs in the skin of CCR10$^{EGFP/EGFP}$ mice while other subsets (EGFP+MHCII− or EGFP− ILCs) increased or did not change significantly compared to their corresponding controls in CCR10$^{+/EGFP}$ mice (FIG. 17B). These results suggest that CCR10 is required for the specific localization of ILCs into the skin but increased maintenance of other subsets of ILCs might compensate for the impaired migration and localization of EGFP+MHCII+ ILCs in absence of CCR10. Compared to CCR10$^{+/EGFP}$ controls, there were significantly increased percentages of EGFP+ ILCs in spleens of CCR10$^{EGFP/EGFP}$ mice (FIG. 17C). These results suggest that in absence of CCR10 expression, the impaired migration of EGFP+ ILCs into the skin is associated with their abnormal accumulation in lymphoid organs that do not express ligands for CCR10, indicating a critical role of CCR10 in the skin-specific localization of CCR10+ ILCs.

CCR6 is expressed on the vast majority of CCR10+ and CCR10− ILCs of sLNs and the skin (FIG. 16). Compared to CCR6-sufficient littermate controls, CCR6$^{-/-}$ mice had no significant change in percentages of CCR10+MHCII+ ILCs in the skin (FIG. 17B). Unlike CCR10$^{EGFP/EGFP}$ mice, CCR6$^{-/-}$ mice did not have abnormally increased accumulation of EGFP+ ILCs in spleens (FIG. 17C). These results suggest that CCR6-knockout itself does not significantly affect localization of CCR10+ ILCs into the skin.

Experiments were also designed to test whether CCR6 coordinated with CCR10 in regulating homeostatic presence of CCR10$^+$ ILCs in the skin using CCR10$^{EGFP/EGFP}$CCR6$^{-/-}$ mice. Compared to CCR10$^{+/EGFP}$ mice, CCR10$^{EGFP/EGFP}$CCR6$^{-/-}$ mice had even fewer EGFP$^+$ MHCII$^+$ ILCs in the skin than CCR10$^{EGFP/EGFP}$ mice (FIG. 17B). Associated with this, there was further increased accumulation of EGFP$^+$ ILCs in spleens of CCR10$^{EGFP/EGFP}$CCR6$^{-/-}$ mice than of CCR10$^{EGFP/EGFP}$ mice (FIG. 17C). There was no significant change of EGFP$^+$ or EGFP$^+$MHCII$^+$ ILCs in sLNs of CCR10$^{EGFP/EGFP}$CCR6$^{-/-}$ mice (FIG. 17A). Together, these results demonstrate that CCR10 and CCR6 coordinately regulate the specific localization and maintenance of CCR10$^+$ and CCR10$^-$ ILCs in the skin.

Figures 18A, 18B, 18C, 18D, 18E, 18F, 18G, 18H:
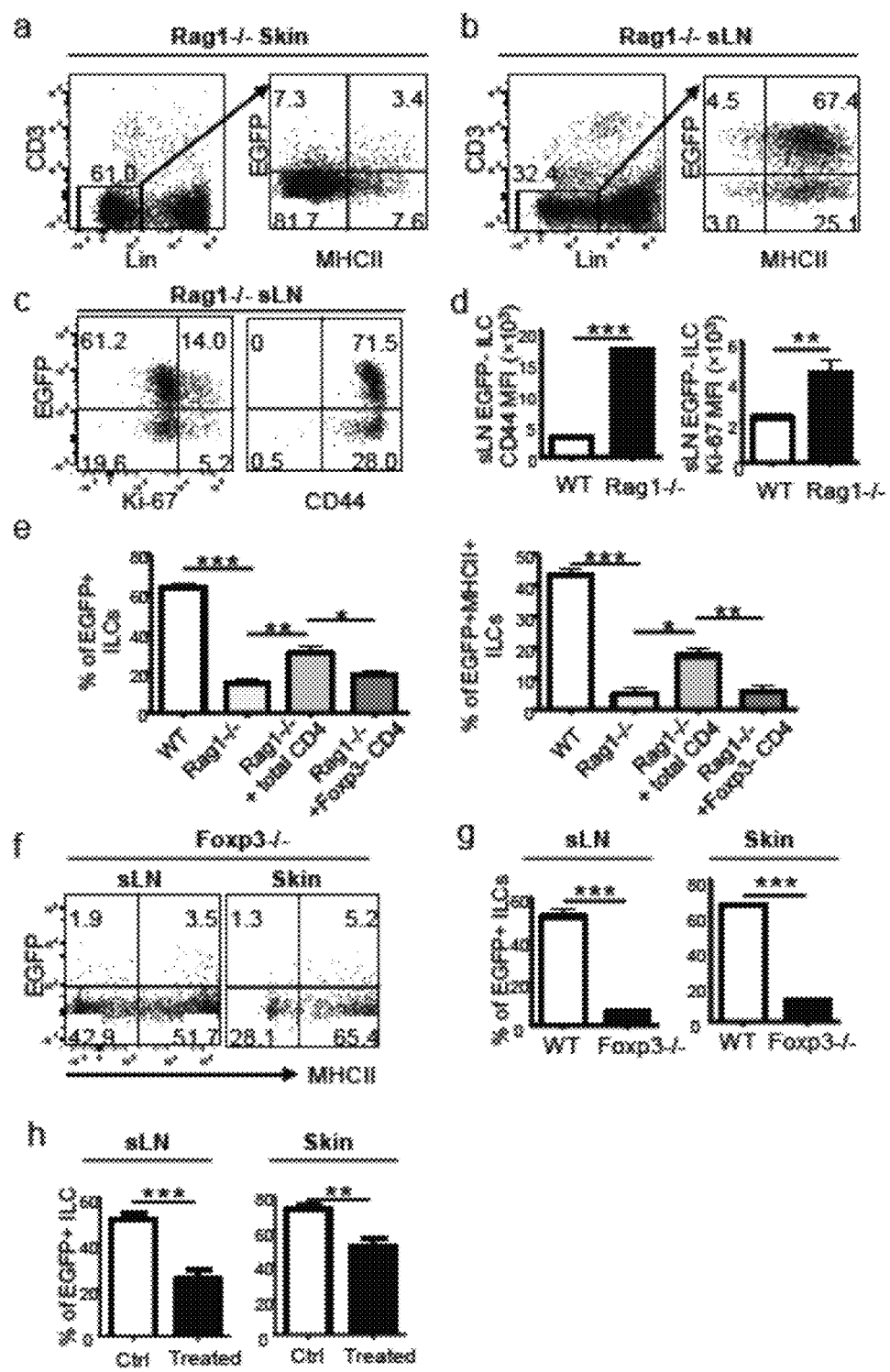
FIGS. 18A through 18H, is a series of images demonstrating that Treg cells are critical for the generation and maintenance of CCR10+ sILC cells.

Dysregulated Activation of ILCs in Skin-Draining Lymph Nodes and Absence of CCR10$^+$ ILCs in the Skin of Rag1$^{-/-}$ Mice Since CCR10 is also involved in localization of resident T cells in the homeostatic skin, we crossed CCR10$^{EGFP/EGFP}$ mice onto Rag1$^{-/-}$ background with intention to study how CCR10$^+$ ILCs were regulated and functioned without T cells. Surprisingly, in Rag1$^{-/-}$CCR10$^{+/EGFP}$ mice, the vast majority of skin_ILCs were CCR10(EGFP)$^-$ and had no expression of MHCII (FIG. 18a), indicating that they were differently activated ILCs. The reduced CCR10$^+$ skin_ILCs in Rag1$^{-/-}$CCR10$^{+/EGFP}$ mice was not due to the reduced generation of CCR10$^+$ ILCs in sLNs. There were high percentages of CCR10$^+$MHCII$^+$ ILCs in sLNs of Rag1$^{-/-}$CCR10$^{+/EGFP}$ mice (FIG. 18b). Interestingly, CCR10$^-$ ILCs in sLNs of Rag1$^{-/-}$CCR10$^{+/EGFP}$ mice also displayed activated phenotypes, as indicated by their uniform expression of high levels of CD44 and similar percentages of Ki-67$^+$ population as CCR10$^+$ ILCs (FIG. 18c), which were higher than CCR10$^-$ sLN_ILCs of WT mice (FIG. 18d). These results suggest that the preferential activation/generation of CCR10$^+$ ILCs in sLNs and their homeostatic presence in the skin are critically dependent on adaptive immune cells.

Treg Cells-Regulated Homeostatic Conditions are Critically Required for Generation and Establishment of CCR10$^+$ ILCs in Skin-Draining Lymph Nodes and the Skin Skin-resident CD4$^+$ T cells are critically involved in the skin homeostasis. Experiments were designed to test whether transfer of CD4$^+$ T cells would help re-establishment of homeostatic presence of CCR10$^+$ ILCs in the skin of Rag1$^{-/-}$ CCR10$^{+/EGFP}$ mice. Indeed, adoptive transfer of CD4$^+$ splenic T cells of WT mice significantly increased percentages of CCR10$^+$ and CCR10$^+$MHCII$^+$ ILCs in the skin of Rag1$^{-/-}$CCR10$^{+/EGFP}$ mice (FIG. 18e).

Treg cells are a major subset of CD4$^+$ T cells critically involved in immune homeostasis. Experiments were therefore designed to test whether Treg cells were required for the CD4$^+$ T cell-rescued CCR10$^+$ ILC homeostasis in the skin. Indeed, transfer of Treg-depleted splenic CD4$^+$ T cells could not rescue the impaired CCR10$^+$ skin_ILC homeostasis in Rag1$^{-/-}$CCR10$^{+/EGFP}$ mice (FIG. 18e).

Experiments were also designed to test the requirement of Treg cells in generation and homeostatic presence of CCR10$^+$ ILCs in sLNs and the skin using Foxp3$^{-/-}$ mice, which lack all Treg cells and develop the skin (and systemic) inflammation. Very few ILCs of sLNs and the skin of Foxp3$^{-/-}$ mice expressed CCR10 (FIG. 18f-18g), demonstrating that Treg-dependent homeostatic conditions were critical for the preferential generation of CCR10$^+$ ILCs in sLNs and their establishment in the skin.

Skin Inflammation Suppresses Generation of CCR10$^+$ ILCs in Skin-Draining Lymph Nodes and their Presence in the Skin Dysregulated activated ILCs contribute to inflammation symptoms in the skin. The specific generation and presence of CCR10$^+$ ILCs in sLNs and the skin under only homeostatic conditions suggest that they are different from those mediating the skin inflammation. To further define how inflammatory conditions affected the programming of CCR10$^+$ ILCs, we treated CCR10$^{+/EGFP}$ mice with topical application of calcipotriol, a synthetic vitamin D3 analog that induces atopic dermatitis-like skin inflammation mediated by ILC2 cells. The treatment resulted in significant reduction of CCR10$^+$ ILCs in sLNs and the skin (FIG. 18h), suggesting that generation and establishment of CCR10$^+$ ILCs in sLNs and the skin was suppressed under these inflammatory conditions.

CCR10$^+$ ILCs Regulates Homeostasis of Resident Treg Cells in the Skin

The predominance of CCR10$^+$ ILCs in the healthy skin suggests that they contribute to immune homeostatic regulation. Consistent with this idea, CCR10$^+$ ILCs have molecular potentials as regulatory APCs for Th cells with their high levels of expression of MHCII and the co-inhibitory molecule PD-L1 but low levels of expression of co-stimulatory molecules (FIG. 16), raising the possibility that CCR10$^+$ ILCs regulate homeostasis of CD4$^+$ Th cells, particularly Treg cells, in the skin.

Figures 18C, 19A:
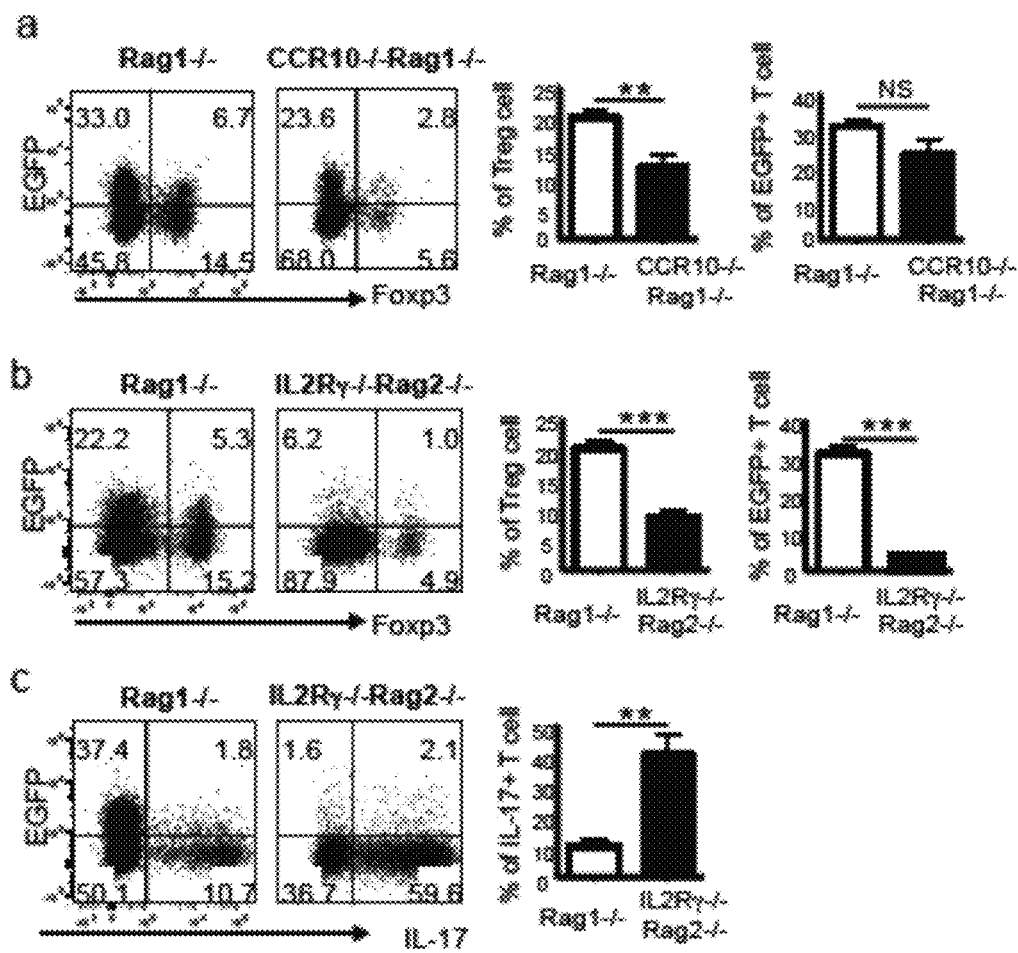

To address specifically the role of CCR10$^+$ ILCs in homeostasis of Th cells in the skin, we tested whether transferred CD4$^+$ splenic T cells could be able to establish homeostasis in the skin of CCR10$^{EGFP/EGFP}$Rag1$^{-/-}$ recipient mice as efficiently as in CCR10-sufficient Rag1$^{-/-}$ recipient mice. Compared to donor CD4$^+$ T cells in the skin of Rag1$^{-/-}$ recipients, donor CD4$^+$ T cells in the skin of CR10$^{EGFP/EGFP}$Rag1$^{-/-}$ recipients had significantly reduced percentages of Treg cells (FIG. 19a), indicating that CCR10$^+$ skin_ILCs were important for homeostatic establishment of skin Treg cells. To further determine the role of ILC in homeostatic establishment of skin-resident T cells, we transferred CD4$^+$ splenic T cells into IL2Rγ$^{-/-}$Rag2$^{-/-}$ mice, which lack all ILCs. There were more severely reduced Treg cells of the donor origin in the skin of IL2Rγ$^{-/-}$Rag2$^{-/-}$ recipients than of CCR10$^{EGFP/EGFP}$Rag1$^{-/-}$ recipients (FIG. 19b). In addition, in contrast to donor T cells in the skin of Rag1$^{-/-}$ or CCR10$^{EGFP/EGFP}$Rag1$^{-/-}$ recipients, nearly all donor T cells in the skin of IL2Rγ$^{-/-}$Rag2$^{-/-}$ recipients were CCR10$^-$ (FIG. 19b), indicating that the transferred CD4+ T cells could not establish homeostasis in the skin of IL2Rγ$^{-/-}$Rag2$^{-/-}$ recipients. Consistent with this, markedly higher percentages of donor T cells in the skin of IL2Rγ$^{-/-}$Rag2$^{-/-}$ recipients expressed IL-17A than those of Rag1$^{-/-}$ recipients (FIG. 17c). Together, these results demonstrate that CCR10$^+$ skin_ILCs are critical in homeostatic regulation of skin-resident T cells.

The results presented herein demonstrate identification of a novel population of skin-resident CCR10+ ILCs that are generated in the skin dLNs and involved in regulation of the CD4+ cells to promote the *cutaneous* immune homeostasis. Reciprocally, the generation of CCR10+ ILCs in the skin dLNs and their localization/maintenance in the skin are dependent on immune homeostatic conditions regulated by T cells, particularly Tregs. These findings demonstrate that skin CCR10+ sILC and T cells inter-depend on each other to maintain the immune homeostasis and prevent the autoimmune inflammation in skin.

Example 3: CCR10 in the Prevention of Psoriasis-Like Skin Inflammation

Figures 20A, 20B, 20C, 20D:
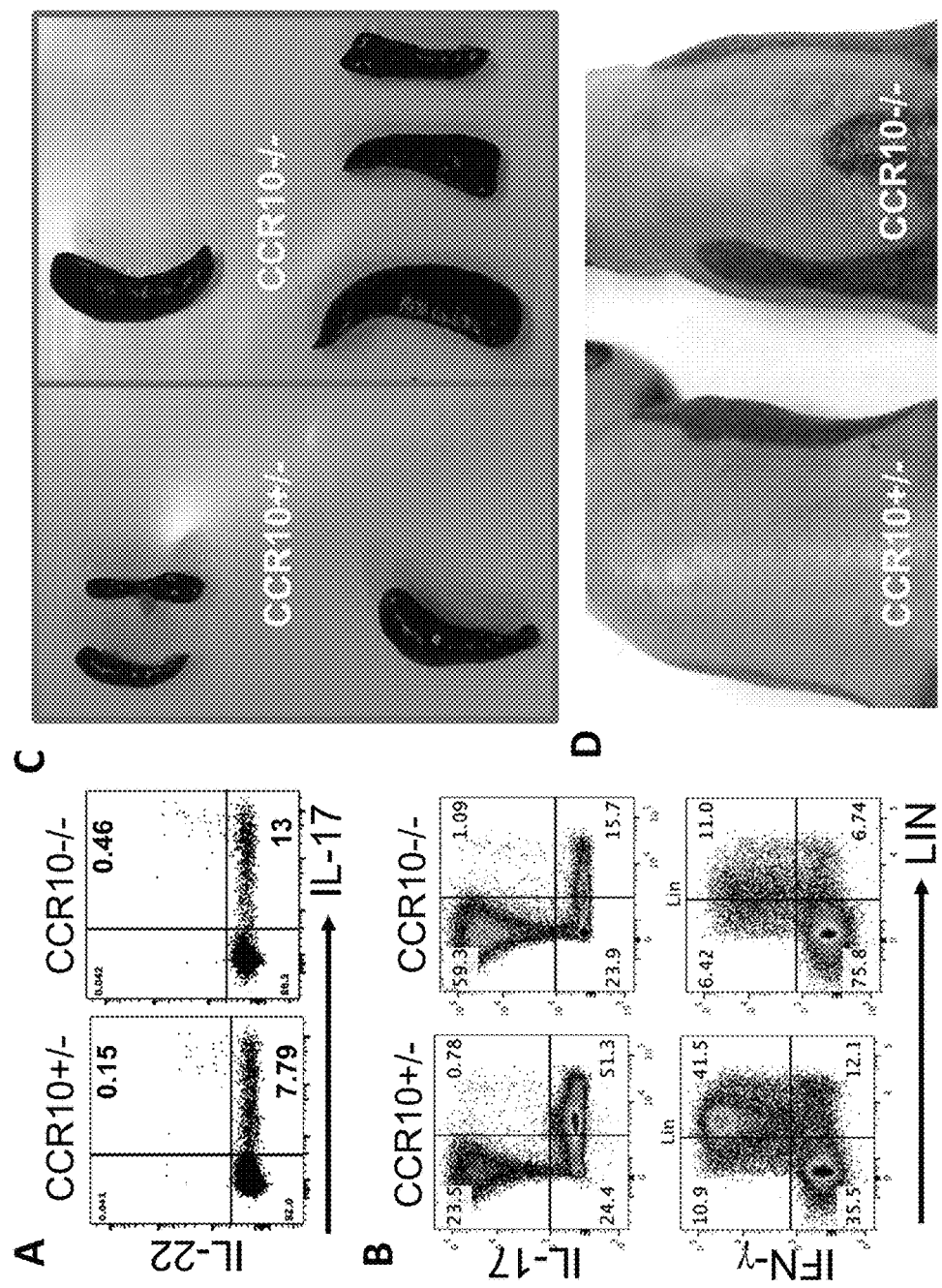
FIGS. 20A through 20D, is a series of images demonstrating that CCR10$^{-/-}$ mice have increased percentages of IL-22/IL-17-producing cells in the skin and are prone to develop psoriasis-like skin inflammation symptoms compared to CCR10$^{+/-}$ mice.

Increased expression of IL-17 by skin immune cells of CCR10$^{-/-}$ mice suggests that CCR10-mediated signals regulate proper expression of IL-17 (FIGS. 20A and 2), an important pro-inflammatory cytokine involved in the development of psoriasis, to suppress the disease development. The increased expression of IL-17 in CCR10$^{-/-}$ skin T cells is more drastic in old mice (FIG. 20B) while the expression of IFN-γ is further decreased in old CCR10$^{-/-}$ mice (FIG. 20B). CCR10 is also important to prevent over-expression of IL-22 since CCR10$^{-/-}$ skin lymphocytes expressed higher levels of IL-22 (FIG. 20A), another cytokine involved in the psoriasis. Together, these results demonstrate that without CCR10, the increased expression of IL-17/IL-22 might cause increased incidence of inflammation, especially in aged mice. Consistent with this idea, old CCR10$^{-/-}$ mice had enlarged spleens compared to CCR10$^{+/-}$ control mice (FIG. 20C). To test directly whether CCR10 is important in prevention of psoriasis, we treated CCR10$^{-/-}$ and CCR10$^{+/-}$ mice with the topical application of imiquimod, a chemical that induces psoriasis-like skin inflammatory symptoms. Indeed, compared to CCR10$^{+/-}$ mice, CCR10$^{-/-}$ mice had much more severe psoriasis-like skin inflammation after imiquimod treatment (FIG. 20D). These results demonstrate that promoting CCR10 signals could alleviate or treat the psoriasis.

Example 4: CCR10 in the Prevention of Intestinal Inflammation

CCR10 also regulates the immune homeostasis in the mucosal sites such as the intestines where another of its ligand, CCL28, is highly expressed. Experiments were designed to compare CCR10$^{-/-}$ and CCR10$^{+/-}$ mice to test the role of CCR10 as a regulator of intestinal homeostasis, which has important clinic relevance to inflammatory bowel diseases (IBD).

Figures 21A, 21B, 21C, 21D, 21E:
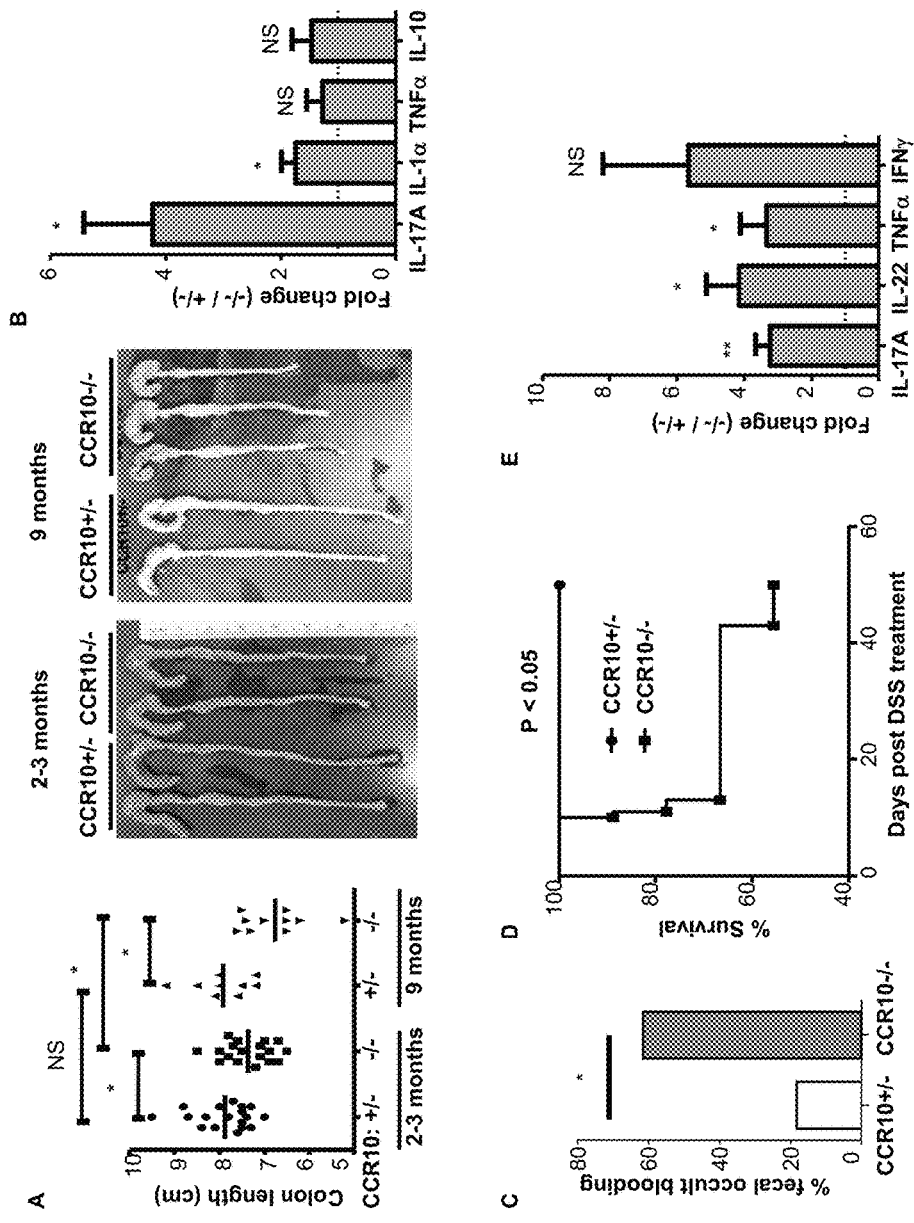
FIGS. 21A through 21E, is a series of images demonstrating that development of spontaneous inflammatory symptoms in colons and impaired recovery from DSS-induced colitis in CCR10$^{-/-}$ mice.

Development of Spontaneous Inflammatory Symptoms in Colons and Impaired Recovery from DSS-Induced Colitis in CCR10$^{-/-}$ Mice Compared to CCR10$^{+/-}$ mice, aging CCR10$^{-/-}$ mice have shorter colons associated with higher gene expression of IL-17 and IFN-γ, indicating spontaneous development of intestinal inflammation (FIGS. 21A and 21B). Furthermore, upon treatment with dioctyl sodium sulfosuccinate (DSS), CCR10$^{-/-}$ mice had significantly higher frequency of fecal occult blooding than CCR10$^{+/-}$ mice (FIG. 21C), and had increased incidence of death (FIG. 21D). Levels of TNF-α, IL-17 and IL-22 were all higher in colons of DSS-treated CCR10$^{-/-}$ mice than CCR10$^{+/-}$ controls (FIG. 21E). Together, these results demonstrate that CCR10 is critical in the intestinal immune homeostasis.

Figures 22A, 22B, 22C, 22D, 22E:
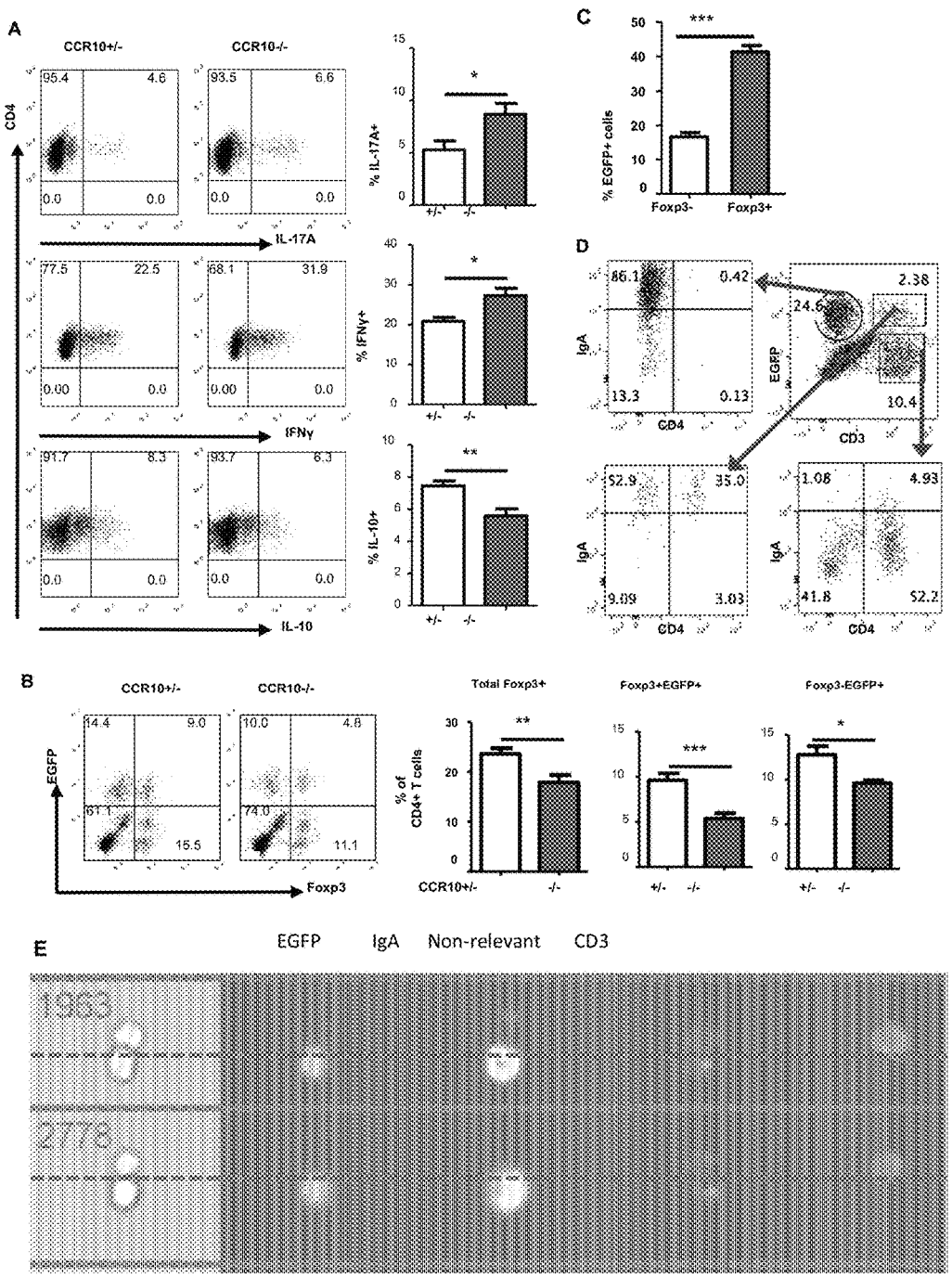
FIGS. 22A through 22E, is a series of images demonstrating that CCR10$^{-/-}$ mice have impaired Treg and Teff cells in the intestine.

CCR10 is Important for the Homeostasis of Treg and Teff Cells in the Intestines to Prevent Intestinal Inflammation The increased expression of the inflammatory cytokines such as IL-17 and IL-22 in the intestines of CCR10$^{-/-}$ mice could be due to dysregulated T cells. Compared to CCR10$^{+/-}$ controls, higher percentages of intestinal CD4+ T cells of CCR10$^{-/-}$ mice expressed IL-17A as well as IFN-γ (FIG. 22A). In contrast, total CD4$^+$ intestinal T cells had reduced percentages of regulatory IL-10$^+$ T cells due to reduced numbers of Treg cells (FIGS. 22A and 22B). Notably, EGFP+ Foxp3+ CD4+ Treg cells were reduced more significantly than EGFP+ Foxp3− CD4+ Teff cells in intestines of CCR10$^{-/-}$ mice (FIG. 22B), suggesting that CCR10 is important in the balanced presence of Treg and Teff cells in the intestine. The more severe reduction of the EGFP+ intestinal Treg cells (FIG. 22B) in CCR10$^{-/-}$ mice correlates with the finding that higher percentages of intestinal Treg cells stain positive for EGFP (CCR10) (FIG. 22C). However, CCR10 is not directly involved in the regulation of T cell homeostasis since intestinal T cells themselves do not express CCR10 (FIGS. 22D and 22E). Instead, intestinal T cells form conjugates with CCR10 (EGFP)+ IgA+ cells (FIGS. 22D and 22E), supporting a notion that CCR10+ IgA+ cells interact with intestinal T cells to promote their homeostasis and prevent the intestinal inflammation. Therefore promoting the CCR10/ligand signals could potentially reduce intestinal inflammation in IBD diseases.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of inhibiting an immune response in a mammal suffering from psoriasis, the method comprising administering to the mammal in need thereof an effect amount of a composition comprising an activator of CCR10, wherein the activator is CCL27.

* * * * *